United States Patent [19]
Coffman et al.

[11] Patent Number: 5,906,747
[45] Date of Patent: *May 25, 1999

[54] SEPARATION OF MOLECULES FROM DILUTE SOLUTIONS USING COMPOSITE CHROMATOGRAPHY MEDIA HAVING HIGH DYNAMIC SORPTIVE CAPACITY AT HIGH FLOW RATES

[75] Inventors: Jonathan L. Coffman, Marlborough, Mass.; Pierre Girot, Paris; Egisto Boschetti, Croissy sur Seine, both of France

[73] Assignee: Biosepra Inc., Marlborough, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/556,313

[22] Filed: Nov. 13, 1995

[51] Int. Cl.⁶ .................................................. B01D 15/08
[52] U.S. Cl. ...................... 210/635; 210/656; 210/198.2; 530/413; 530/417
[58] Field of Search ................ 210/635, 656, 210/198.2, 502.1; 502/402; 530/413, 417

[56] References Cited

U.S. PATENT DOCUMENTS

| | | | |
|---|---|---|---|
| 4,045,353 | 8/1977 | Kosaka | 210/198.2 |
| 4,140,653 | 2/1979 | Imura | 210/198.2 |
| 4,189,370 | 2/1980 | Boschetti | 210/198.2 |
| 4,229,536 | 10/1980 | DeFilippi | 435/176 |
| 4,254,129 | 3/1981 | Carr et al. | 424/267 |
| 4,335,017 | 6/1982 | Miles | 210/635 |
| 4,352,884 | 10/1982 | Nakashima et al. | 435/180 |
| 4,385,991 | 5/1983 | Rosevear | 210/635 |
| 4,415,631 | 11/1983 | Schutijser | 428/405 |
| 4,443,339 | 4/1984 | Rosevear | 210/635 |
| 4,452,916 | 6/1984 | Boschetti | 521/38 |
| 4,460,625 | 7/1984 | Emmons et al. | 427/136 |

(List continued on next page.)

FOREIGN PATENT DOCUMENTS

| | | | |
|---|---|---|---|
| 2 453 854 | 11/1980 | France | 210/198.2 |
| 2 541 593 | 2/1983 | France | 210/198.2 |
| 50-115298 | 9/1975 | Japan | 210/198.2 |
| 51-074694 | 6/1976 | Japan | 210/198.2 |
| 52-054496 | 5/1977 | Japan | 210/198.2 |
| 61-074644 | 4/1986 | Japan | 210/198.2 |
| 62-286533 | 12/1987 | Japan | 210/198.2 |
| 747513 | 7/1980 | U.S.S.R. | 210/198.2 |
| WO 88/09656 | 12/1988 | WIPO | 210/198.2 |
| WO 90/06796 | 6/1990 | WIPO | 210/198.2 |
| WO94/03170 | 2/1994 | WIPO | 210/198.2 |
| 95/26977 | 9/1995 | WIPO | 530/42 |

OTHER PUBLICATIONS

J. Horvath, et al., *High–performance protein separations with novel strong ion exchangers*, Journal of Chromatography A, 679/11–22 (1994).

E. Boschetti, et al., *Preparative high–performance liquid chromatographic separation of protein with HyperD ion–exchange supports*, Journal of Chromatography B, 664/225–231 (1995).

Akagi et al., 1987, "Antiallergic effects of terfenadine on immediate type hypersensitivity reactions", Immunopharmacol. Immunotoxicol. 9:259–279.

(List continued on next page.)

Primary Examiner—Ernest G. Therkorn
Attorney, Agent, or Firm—Pennie & Edmonds LLP

[57] ABSTRACT

This invention relates generally to modified porous solid chromatographic media and processes for the preparation and use of same. In particular, chromatographic media of porous mineral oxide, polymeric, or polymer-coated mineral oxide supports are disclosed which are characterized by a reversible high sorptive capacity and high intraparticle mass transfer rates. In order to prevent non-specific adsorption of or interaction with biomolecules, these supports may be passivated by use of a passivation mixture comprising a main monomer, a passivating monomer, and a crosslinking agent, which mixture upon polymerization results in substantial elimination of the undesirable non-specific interaction with biomolecules.

15 Claims, 14 Drawing Sheets

U.S. PATENT DOCUMENTS

| | | | |
|---|---|---|---|
| 4,618,533 | 10/1986 | Steuck | 428/315.7 |
| 4,627,992 | 12/1986 | Badenhop | 210/500.38 |
| 4,673,734 | 6/1987 | Tayot et al. | 530/364 |
| 4,724,207 | 2/1988 | Hou | 435/180 |
| 4,729,834 | 3/1988 | Itoh | 210/670 |
| 4,761,232 | 8/1988 | Bright | 210/500.42 |
| 4,783,465 | 11/1988 | Sunshine et al. | 514/255 |
| 4,829,064 | 5/1989 | Sunshine et al. | 514/255 |
| 4,882,048 | 11/1989 | Blaschke et al. | 210/198.2 |
| 4,882,226 | 11/1989 | Schutyser | 210/198.2 |
| 4,917,793 | 4/1990 | Pitt et al. | 210/94 |
| 4,931,498 | 6/1990 | Pidgeon | 210/656 |
| 4,933,372 | 6/1990 | Feibush et al. | 521/91 |
| 4,957,620 | 9/1990 | Cussler | 210/635 |
| 4,965,289 | 10/1990 | Sherrington et al. | 521/53 |
| 5,015,373 | 5/1991 | Carr | 210/198.2 |
| 5,019,270 | 5/1991 | Afeyan et al. | 210/656 |
| 5,019,591 | 5/1991 | Gardner et al. | 514/461 |
| 5,030,352 | 7/1991 | Varady | 210/502.1 |
| 5,045,190 | 9/1991 | Carbonell | 210/198.2 |
| 5,047,438 | 9/1991 | Feibush et al. | 521/61 |
| 5,053,135 | 10/1991 | Boschetti | 210/635 |
| 5,066,398 | 11/1991 | Soria | 210/500.27 |
| 5,085,779 | 2/1992 | Crane et al. | 210/635 |
| 5,087,369 | 2/1992 | Tanimoto et al. | 210/635 |
| 5,091,433 | 2/1992 | Wulff | 210/635 |
| 5,104,729 | 4/1992 | Stedronsky | 428/304.4 |
| 5,114,577 | 5/1992 | Kusano | 210/635 |
| 5,135,650 | 8/1992 | Hjerten | 210/198.2 |
| 5,137,633 | 8/1992 | Wang | 210/490 |
| 5,160,627 | 11/1992 | Cussler | 210/635 |
| 5,182,016 | 1/1993 | Funkenbusch | 210/636 |
| 5,240,602 | 8/1993 | Hammen | 210/198.2 |
| 5,268,097 | 12/1993 | Girot et al. | 210/198.2 |
| 5,393,430 | 2/1995 | Girot et al. | 210/635 |
| 5,445,732 | 8/1995 | Girot et al. | 210/198.2 |
| 5,470,463 | 11/1995 | Girot et al. | 210/198.2 |

OTHER PUBLICATIONS

Akagi et al., "Inhibitory Effects of Terfenadine on a Variety of Actions Exerted by Leukotriene $D_4$ and Platelet Activating Factor", Oyo Yakuri 35(5):355–371 (1988) with English Abstract.

Ariëns, 1990, "Stereoselectivity in pharmacodynamics and pharmacokinetics", Schweiz. Med. Wochenschr. 120:131–134.

Ariëns, 1990, "Racemische therapeutica probleemmiddelen", Pharmaceutisch Weekblad 125:552–554.

Ariëns, 1991, "Racemic therapeutics—ethical and regulatory aspects", Eur. J. Clin. Pharmacol. 41:89–93.

Chan et al., 1990, "Lack of interconversion of the enatiomers of terfenadine in–vivo: the pharmackokinetics and disposition of the individual enantiomers in the male beagle dog", Pharma. Res. 7:S222, abs.PPDM8064.

Chan et al., "Direct Enantiomeric Separation of Terfenadine and Its Major Acid Metabolite by High–Performance Liquid Chromatography, and the Lack of Stereoselective Terfenadine Enantiomer Biotransformation in Man" J. Chromatog. 571:291–297(1991).

Chemical Abstracts 112 abstract 171943 (1990).

Chen et al., 1991, "Determination of the metabolites of terfenadine in human urine by thermospray liquid chromatography—mass spectrometry", J. Pharm. Biomed. Anal. 9:929–933.

Chen et al., "Antihistaminic Effect of Terfenadine: A New Piperidine–type Antihistamine" *Drug Dev. Res.* 2:181–196(1982).

Cohen et al., "Meclizine and Placebo in Treating Vertigo of Vestubular Origin, Relative Efficacy in a Double–Blind Study" Arch. Neurol. 27:129–135(1972).

Connell, J.T., "Pharmacology and Clinicial Efficacy of Terfenadine, a New $_1$–Receptor Antagonist", Pharmacotherapy 5(4):201–20(1985).

Coutant et al., 1991, "Determination of terfenadine and terfenadine acid metabolite in plasma using solid–phase extraction and high–performance liquid chromatography with fluorescence detection", J. Chromatography 570:139–148.

J. Hong, et al., "Isolation and Characterization of a Novel B Cell Activation Gene", The Journal of Immunology, vol. 150, 3895–3904, No. 9, May 1993.

Honig et al., 1992, "Changes in the pharmacokinetics and electrocardiographic pharmacodynamics of terfenadine with concomitant administration of erythromycin", Clin. Pharma. Ther. 52:231–238.

Garteiz et al., "Pharmacokinetics and Biotransformation Studies of Terfenadine in Man", Arzneim–Forsch./Drug Res. 32(11): 1185–1190(1982).

Graham et al., "Rate of Protein Absorption and Desorption on Cellulosic Ion Exchangers", *ChE Journal* (vol. 28, No. 2), Mar. 1982 p. 245.

W. Kopaciewicz et al., "Influence Of Pore and Particle Size On the Frontal Uptake Of Proteins", *Journal of Chromatography*, 409 (1987), 111–124.

Monahan et al., "Torsades de Pointes Occurring in Association With Terfenadine Use", Jama 264(21):2788–2790(1990).

Okerholm et al., "Bioavailability of Terfenadine in Man", Biopharm. Drug Dispos. 2:185–190(1981).

Physician's Desk Reference®, pp. 1313–1314, 45th Edition, Medical Economics Data Production Co., N.J., 1991.

Snyder, "Introduction to Modern Liquid Chromatorgraphy", John Wiley & Sons, Inc., NY (1979) pp. 488–489.

Tasaka et al., 1986, "Intracellular calcium release induced by histamine releasers and its inhibition by some antiallergic drugs", Ann Allergy 56:464–469.

Tasaka et al., 1988, "Antiallergic effects of terfenadine on immediate type hypersensitivity reactions and the mechanisms of those actions", Yakuri to Chiryo 16:2465–2480.

K. Tasaka et al., "Influence of the Optical Isomers of Terfenadine on EEG Spectral Powers in Conscious Rats", Yakuri Pharmacometrics 38(6) 489–493 (1989).

Testa et al., 1990, "Racemates verses enantiomers in drug development: dogmatism or pragmatism?", Chirality 2:129–133.

H. Tsou et al., Prediction of Adsorption and Desorption of Protein on Dextran Based Ion–Exchange Resin, ChE Journal (vol. 31, No. 12), Dec. 1995, pp. 1959.

Wood, C.D., "Antimotion Sickness and Antiemetic Drugs", Drugs 17:471–479(1979).

Woosley et al., 1993, "Mechanism of the cardiotoxic actions of terfenadine", JAMA 269:1532–1536.

H. Yoshida et al., "Analytical Solution Of The Breakthrough Curve For Rectangular Isotherm Systems", Chemical Engineering Science, Vo. 39, No. 10, pp. 1489–1497, 1984.

Zamani et al., Chemical Abstracts CA 116(17): 1656812, 1991.

Zamani et al., 1991, "Enantiomeric analysis of terfenadine in rat plasma by HPLC", Chirality 3:467–470.

SEPARATION OF MOLECULES FROM DILUTE SOLUTIONS USING COMPOSITE CHROMATOGRAPHY MEDIA HAVING HIGH DYNAMIC SORPTIVE CAPACITY AT HIGH FLOW RATES

FIELD OF THE INVENTION

This invention relates to chromatography media and their use. In particular, composite media are disclosed which are characterized by a reversible high sorptive capacity. These media may be passivated to prevent non-specific adsorption of or interaction with biomolecules such as proteins, oligopeptides, polysaccharides, and nucleotides. The composite media of the present invention exhibit characteristics that are highly desirable in chromatographic applications, such as high porosity, physical rigidity, high charge density, and chemical stability under a variety of extreme conditions, and may be used advantageously with especially dilute feed streams in high-flow, high-efficiency mass transfer chromatographic techniques that can be carried out in a fluidized-bed, packed-bed, or other mode of operation.

BACKGROUND OF THE INVENTION

Polyfunctional macromolecules, such as proteins, can be purified by a variety of techniques. One of these techniques is known as ion-exchange chromatography. In ion-exchange chromatography, proteins are separated on the basis of their net charge. For instance, if a protein has a net positive charge at pH 7 it will bind to a negatively charged ion-exchange resin packed in a chromatography column. The protein can be released, for example, by increasing the pH or adding cations that compete for binding to the column with the positively charged groups on the protein. Thus, proteins that have a low density of net positive charge, and thus a lower affinity for the negatively charged groups of the column, will tend to emerge first, followed by those having a higher charge density.

Generally, the ion-exchange resins which are used in these procedures are solids possessing ionizable chemical groups. Two types exist: cation-exchangers, which contain acidic functional groups such as sulfate, sulfonate, phosphate or carboxylate, and a second type, anion-exchangers, which contain functional groups such as tertiary and quaternary amines. These ionizable functional groups may be inherently present in the resin or they may be the result of the chemical modification of the organic or mineral substance comprising the particles.

Organic ionic-exchangers which are made from polysaccharide derivatives, e.g., derivatives of agarose, dextran, cellulose, etc., have been used for both laboratory and industrial scale ion-exchange chromatography. However, these ion-exchangers have many disadvantages. First, polysaccharide-derived ion-exchangers are not very mechanically stable and are not resistant to strong acids. This instability limits the length of the column and, also, limits the flow rate through the column.

Second, such ion-exchangers have limited sorption capacity due to the limited number of ionic or ionizable groups that can be attached to the polysaccharide.

Third, such ion-exchangers have a dynamic sorption capacity that remains the same or often decreases with decreasing concentration of the desired biological macromolecule of interest in the feedstream. Since biological macromolecules of interest are often produced in dilute feed streams, this decrease in dynamic sorption capacity is disadvantageous, limiting the users to slow column velocities.

Fourth, these polysaccharidic derivatives are poor adsorbents for use in rapid fluidized-bed separations because of the low density of the material. In a fluidized bed it is desirable to pass the fluid without simultaneously washing out the particles. Therefore, it is generally desirable to have as great a density difference as possible between the solid particles (e.g., silica) and the fluidizing medium.

The intrinsic high density of inorganic sorbents based on passivated mineral substrates facilitates packing and rapid decantation into chromatographic columns. Dense packing prevents formation of empty spaces and channeling when using packed beds. On the other hand, fluidization of dense particles in aqueous suspension is possible at high flow rates that, in turn, are very desirable when dealing with large scale applications. Operation of fluidized beds at high superficial flow velocities is generally not possible with low-density organic or polymeric sorbents, which can be eluted from fluidized beds at relatively low liquid flow rates.

On the other hand, synthetic polymers are mechanically more stable than inorganic media, and the former are more resistant to strong acidic conditions. However, they suffer disadvantages as well, such as limited capacity, limited solute diffusivity and thus, limited productivity. These synthetic polymers also suffer to some extent from the problem of non-specific adsorption of biomolecules, such as proteins. Untreated mineral media such as silica are also inadequate in many chromatographic protein separation applications because of such non-specific adsorption.

Non-specific adsorption is caused by the interaction of a protein with the surface of the solid particle—be it organic or inorganic in nature. For example, silica is an acidic compound, and the negatively charged silanol groups present at the solid/liquid interface tend to create a separate ionexchange interaction between the surface of silica and the protein. Non-specific adsorption is also caused by hydrogen bonding that takes place between, e.g., amino groups present in the amino acid residues of proteins and these same silanols present at the silica surface. Such non-specific interactions create separation problems during chromatography—e.g., poor protein recovery and/or inadequate resolution. An important objective in the design of a chromatographic separation is generally to ensure a "single-model" process of adsorption. However, the ion-exchange behavior associated with surface silanols can create a "mixed model" adsorption system which makes the separation of biomolecules much more difficult. Although the sorption capacity generated by ionic silanol groups is low, the intensity of the interaction between the silanol groups and proteins can be high. These interactions therefore have the potential to cause denaturation of certain proteins.

Finally, both polysaccharides and most hydroxyl-containing synthetic sorbents are sensitive to the cleaning solutions used in industrial settings, which often include strong oxidizing agents such as hypochlorite or peracetic acid and which may be characterized by extremes of pH.

Thus, there is an important need for the development of improved passivation methods for the treatment of the surfaces of both polymeric and inorganic chromatographic media in contact with protein-containing solutions, which method is capable of preventing or minimizing such non-specific interactions between proteins and the chromatographic media in order to improve the efficiency of chromatographic processes.

Several previous investigators have sought to passivate various microporous media including membranes and particulate chromatographic sorbents by applying thin surface coatings to inorganic or organic/polymeric substrates. For example, Steuck, in U.S. Pat. No. 4,618,533, discloses a porous polymeric membrane substrate fashioned from a thermoplastic organic polymer upon which a permanent coating is grafted and/or deposited on the entire membrane surface. The polymerization and crosslinking of the polymerizable monomer upon and within the porous membrane substrate is performed in such a way that a thin coating is deposited upon the entire surface of the porous membrane, including the inner pore walls. Significantly, the porous configurations of the coated, composite membrane structures claimed by Steuck are essentially identical to those of the corresponding uncoated porous membrane substrates, implying that the polymer of Steuck is applied as a thin surface layer or coating that does not interfere with the porosity or flow properties of his composite membranes. Moreover, Steuck does not disclose the concept of a "passivating layer" or the use of monomers capable of functioning as "passivating" monomers within the meaning of the present invention as discussed in more detail below.

Varady et al., in U.S. Pat. No. 5,030,352, disclose pellicular support materials useful as chromatography media which are obtained by applying various thin hydrophilic coatings to the surfaces of hydrophobic polymer substrates (e.g., polystyrene). Varady's surface coatings are applied by first exposing the surfaces of the hydrophobic substrate to a solution of a solute characterized by interspersed hydrophilic and hydrophobic domains; contact between surface and solute takes place under conditions that promote hydrophobic-hydrophobic interaction between solute and substrate, with the result that solute molecules are adsorbed onto the surface of the substrate as a thin coating that is ultimately crosslinked in place. Varady's coating materials may further comprise reactive groups capable of being derivatized to produce various materials useful in ion-exchange, affinity, and other types of chromatographic and adsorptive separations.

Significantly, however, the hydrophilic, functional coating of Varady's invention is limited to a thin adherent film on the surface of the hydrophobic particle. The morphology of this coating layer is a direct and unavoidable consequence of the stated method of its deposition—i.e., by the crosslinking of adjacent solute molecules adsorbed onto the surface of the hydrophobic substrate.

While Varady's coating method is at least partially effective in reducing the non-specific binding of proteins to the substrate, the sorption capacity of the chromatographic materials so produced is necessarily limited and inferior to those of the media produced by the process of the present invention. As discussed in considerably more detail below, the method of the present invention causes the formation of a crosslinked and functional gel that extends out into and substantially fills the pores of the support. As a consequence, the static and dynamic sorption capacities of the chromatographic media are not limited by the porous surface area of the substrate, as is the case with the pellicular materials of Varady's invention.

With regard to previous techniques for the passivation of inorganic or mineral media by surface coating treatments, U.S. Pat. No. 4,415,631 to Schutijser discloses a resin consisting of inorganic silanized particles onto which is bonded a crosslinked polymer comprised of copolymerized vinyl monomers and which contains amide groups. The invention specifies that the inorganic porous substrate, including silica, must be silanized prior to coating. The silanization treatment provides the inorganic porous substrate with reactive groups so that the copolymer can be covalently bonded to the silica surface.

Nakashima et al., in U.S. Pat. No. 4,352,884, also discloses the use of silica as a porous substrate. The silica is coated with a polymer made up of acrylate or methacrylate monomer and a copolymerizable unsaturated carboxylic acid or a copolymerizable unsaturated amine. Nakashima et al. use an already preformed polymer to coat the substrate. Furthermore, Nakashima et al., in a separate and distinct step, utilize a crosslinking agent in a subsequent curing process.

The above-mentioned inventions are not completely successful, partly because of the unstable chemical linkage between the silica and the coating. The products of these inventions have the further disadvantages of not only failing to totally suppress the initial non-specific adsorption but also of introducing additional modes of non-specific adsorption.

Tayot et al., in U.S. Pat. No. 4,673,734, disclose a porous mineral adsorbent that is impregnated with an aminated polysaccharide polymer that is said to cover the internal surface area of the substrate. However, since polysaccharides usually have very large molecular weights and their solutions are quite viscous, this process is not highly effective. Coverage of the entire internal surface of the silica substrate is problematic due to incomplete and uneven filling of the pores of the silica substrate by the large polysaccharide molecules.

The steric problems of Tayot's process result from the large size of the polysaccharides employed, the chains of which cannot penetrate completely within the pores of the substrate. This incomplete penetration results in the creation of a "soft" layer of polysaccharide on the surface of the pore that subsequently causes problems during chromatographic separation. Polysaccharides such as dextran can also spontaneously hydrolyze at low pH, rendering them incompatible with certain cleaning operations that require the column or bed of chromatographic media to be washed with acid, alkaline, or oxidizing agents.

Despite these and other problems associated with the use of inorganic chromatographic media, the use of mineral compounds such as silica as substrates for chromatographic adsorbents is still attractive, because as explained above, chromatographic separations can be performed with such materials at very high flow rates—for example, in very large-scale packed columns or in fluidized beds for industrial operations. What is needed are chromatographic media characterized by high static and dynamic sorption capacity which exhibit improved chemical stability at alkaline and basic conditions and reduced tendencies to cause non-specific protein adsorption. It is an object of the present invention to provide such adsorbent media.

SUMMARY OF THE INVENTION

The present invention provides a method for the separation of biological molecules by chromatography. The method of the invention comprises the steps of passing a sample containing a mixture of biological macromolecules including a biological macromolecule of interest through a column packed with a composite media and recovering the biological macromolecule of interest from the sample. The composite media which characterizes the present invention provides a larger dynamic capacity for a biological macromolecule at low initial feed concentrations, for example, those less than about 2 milligrams per milliliter, than the dynamic capacity provided by the same media for the same macromolecule at higher concentrations, for example, those higher than about 2 milligrams per milliliter. The media preferably provides a larger dynamic capacity for said macromolecule at initial feed concentration in the range of about 10 micrograms per milliliter to about 2 milligrams per milliliter than the dynamic capacity provided by the same media for the same macromolecule at initial feed concentrations in the range of about 2 milligrams per milliliter to about 100 milligrams per milliliter. In a preferred embodiment of the present invention, the sample to be subjected to the separation procedure may have an initial concentration of the biological macromolecule of interest of less than about 2 milligrams per milliliter.

In accordance with the present invention, the media may be a composite media that comprises a porous support comprising voids containing a polymeric network, wherein the composite media provides a value of the flux enhancement factor E greater than about 3, preferably greater than about 20, as determined by the equation $$E = \frac{D_s q_0}{\frac{D_f \varepsilon_p}{\tau} C_0}$$

in which $D_s$ is the experimentally measured effective intraparticle diffusivity of a molecule of interest, $q_0$ is the equilibrium concentration of said molecule within the media particles at equilibrium with $C_0$, $D_f$ is the diffusivity in free solution of said molecule, $\varepsilon_p$ is the fractional void volume of the porous support of the composite media, $\tau$ is the tortuosity of the porous support of the composite media, and $C_0$ is the concentration of said molecule in the feed solution, and is preferably at least about 1 microgram per milliliter, more preferably at least about 10 micrograms per milliliter.

The composite media may be selected to be a chromatographic media, more preferably, ion-exchange chromatography media, so that said biological macromolecules can be separated by (ion-exchange) chromatography. The chromatography media is preferably one that provides an intraparticle diffusional flux that is faster, for instance at least about 30% faster, than the diffusional flux of the biological macromolecules in solution.

The sample containing a mixture of biological macromolecules including a biological macromolecule of interest is generally passed through the column at a flow rate of at least about 50 cm/hr, preferably at least about 500 cm/hr, more preferably at least about 1000 cm/hr.

The recovery step according to the present invention generally comprises passing an eluent solution through the packed column to effect the separation of a preselected biological macromolecule from the mixture. The biological macromolecule will preferably be a protein, an oligopeptide, a carbohydrate, or a polynucleotide.

BRIEF DESCRIPTION OF THE DRAWINGS

FIG. 1.B is a graph which schematically represents the chromatographic separation of a protein mixture consisting of (1) ovalbumin, (2) beta-lactoglobulin, (3) cytochrome c, and (4) lysozyme on an anionic passivated porous support.

FIG. 2.B represents a comparison between the chromatographic separations of a protein mixture consisting of (1) ovalbumin, (2) beta-lactoglobulin, (3) cytochrome c, and (4) lysozyme using an anionic nonpassivated support.

FIG. 3.B shows a graph of productivity versus flow rate for the various porous supports shown in FIG. 3A.

FIG. 6.B shows graphs of the BSA concentration within a medium of the present invention (Q HyperD M) as a function of time during batch uptake experiments for two initial BSA concentrations. Shown also are the results of fitting the data with analytical concentration-vs.-time solutions.

FIG. 7.B shows graphs of the BSA concentration within a medium of the present invention (Q HyperD M) as a function of time during batch uptake experiments for several initial BSA concentrations. Shown also are the results of fitting the data with a numerical concentration-vs.-time solution.

DETAILED DESCRIPTION OF THE INVENTION

Figure 1A:
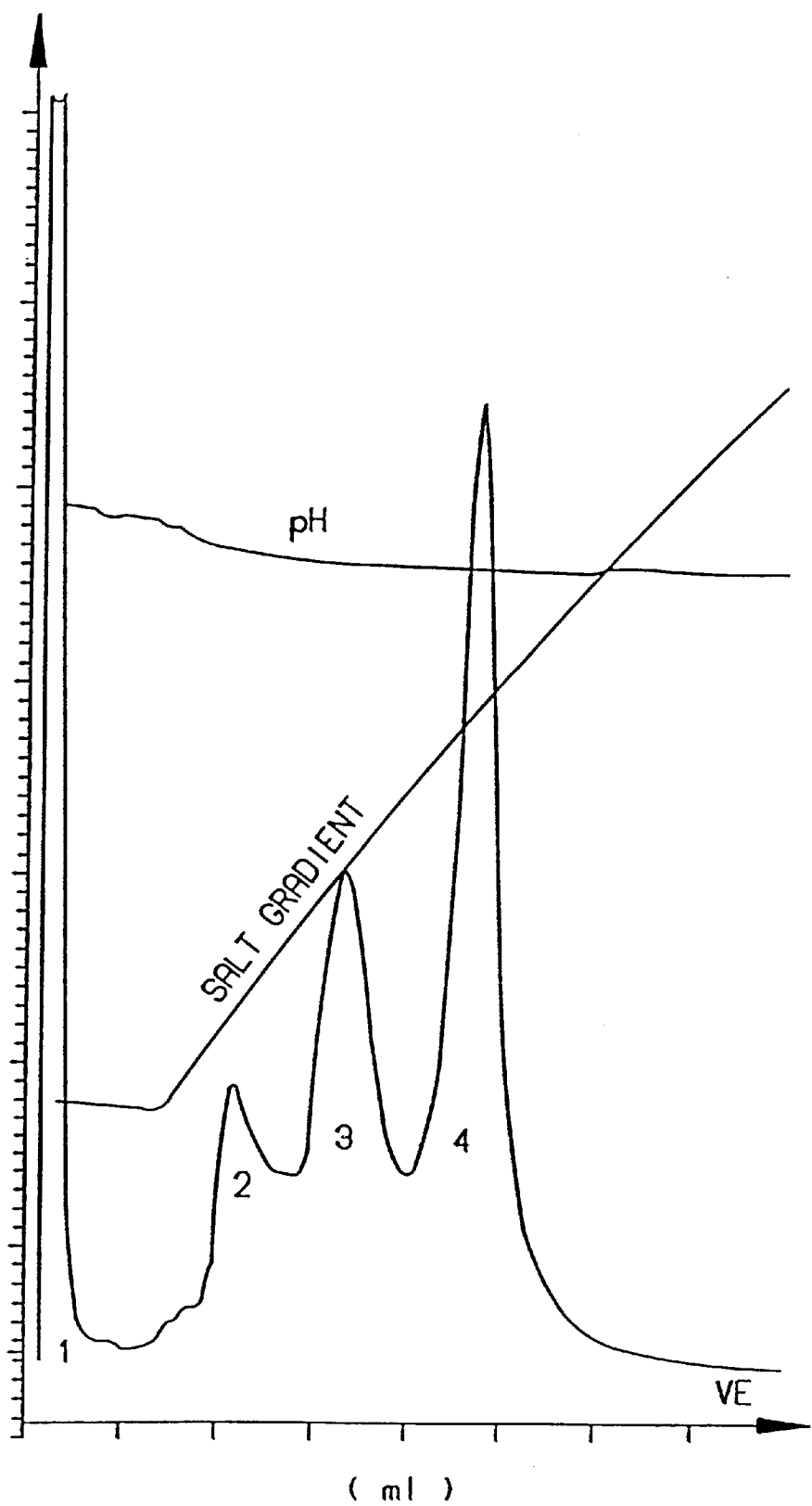
FIG. 1.A is a graph which schematically represents the chromatographic separation of a protein mixture consisting of (1) cytochrome, (2) bovine hemoglobin, (3) ovalbumin (ova), and (4) beta-lactoglobin (β-lac) on a cationic passivated porous support.

The present invention provides a composite media for the separation of biological molecules by chromatography, such as ion-exchange chromatography. As noted above, the media provides a flux enhancement factor E of greater than 3 wherein $$E = \frac{D_s q_0}{\frac{D_f \varepsilon_p}{\tau} C_0}$$

In a further refinement, the media provides a value for a second figure of merit or flux enhancement factor E* of greater than 3, wherein $$E^* = \frac{D_s q_0}{\frac{D_f \varepsilon_p^*}{\tau} C_0}$$

in which $D_s$ is the effective intraparticle diffusivity of the biological molecule of interest, $\tau$ is the tortuosity factor of the composite media, $D_f$ is the diffusivity in free solution of the biological molecule, and $\varepsilon_p^*$ is the species-dependent inclusion porosity of the composite media (Athalye, A. M. et al., *J. Chromatocraphy*, 589 (1992) 71–85).

The terminology "composite media" is intended to cover all combinations of physical (or support) structures or compounds, including mineral oxide matrices, mineral oxide matrices whose interior and exterior surfaces are substantially covered by a thin protective polymer surface coating, metal matrices, and polymeric matrices such as polystyrenes, with chromatographic resins such as those made from chemical substances known to be useful for the preparation of chromatographic separation adsorbents, including polymerized vinyl monomers that contain chromatographically active substituents. The constituents of the composite media can include structures and chromatographic resins made separately or formed together, such as in block copolymers.

An important figure of merit that facilitates understanding the present invention is the formula for flux enhancement factor $$E = \frac{D_s q_0}{\frac{D_f \varepsilon_p}{\tau} C_0}$$

wherein $D_s$ is the experimentally determined effective intraparticle diffusivity of the biological molecule to be separated, $\tau$ is the tortuosity factor of the porous chromatography support, $D_f$ is the diffusivity in free solution of the biological molecule, and $\varepsilon_p$ is the void volume of the composite support matrix measured in the absence of a polymeric gel filling the pores. $D_s$ is defined in such a way that the driving force for diffusion in the particle is the gradient in the total protein concentration at that point in the particle, not just the gradient in "free" or "unbound" protein concentration. Thus the flux enhancement factor E is determined by both the characteristics of the chromatography medium e.g. ($\tau$ and $\varepsilon_p$) and the characteristics of the biological molecule to be separated (e.g. $D_s$ and $D_f$). The variable $D_s$ depends upon the biological molecule as well as on the composite media. This flux enhancement factor E represents the ratio of (i) the intraparticle diffusional solute flux to (ii) the intraparticle flux of solute that would be expected to occur if the pores of the composite media support were devoid of the polymeric network.

The second flux enhancement factor E* takes account of the steric effects of the gel residing within the pores of the composite media. This flux enhancement factor E* is the ratio of (i) the intraparticle diffusional solute flux to (ii) the intraparticle flux of solute that would occur if the pores of the composite media support were filled with a polymeric network identical to that present in the composite media of the invention save for its being incapable of interacting electrostatically or chemically with the solute of interest. The steric effects of the gel decrease the effective area open for diffusion in the composite media. A decrease in effective area for diffusion would, in a conventional media, significantly inhibit diffusion in the gel. In the present invention, however, this steric effect of the gel is overcome by the favorable partitioning of solute into the gel; that is, the high intraparticle solute concentration gives rise to an increase in the total driving force for diffusion in the composite media and thus an increase in the total flux into the particle. It may be noted that E and E* account for the fact that the biological macromolecule must diffuse by a geometrically tortuous route in order to penetrate the particle. Thus, in comparing the enhancement of intraparticle flux with that in free solution, E and E* account for the longer diffusional distance with the tortuosity parameter $\tau$. Values for $\tau$ generally vary between 2 and 6. A value for tortuosity of 2 has been adopted for calculations of E and E* presented below, because such a value typical of many chromatographic media, and because adoption of a tortuosity value of 2 results in calculated E and E* values that are conservative.

The flux enhancement factors E and E* defined above are designed so as to capture the unexpectedly high mass transfer performance (e.g., intraparticle solute fluxes) of the composite media of the present intention. In particular, the first flux enhancement factor E is meant to compare the observed rate of intraparticle solute mass transfer with the rate of mass transfer that would be predicted were the solute to be diffusing into the "empty" (e.g., gel-free) porous support particle from which the composite media of the present invention is fashioned. One of ordinary skill might reasonably expect the solute to diffuse into the gel-containing composite particle no more rapidly than it would diffuse into the "empty" support particle; this expected rate of mass transfer would be proportional to the solution-phase solute concentration driving force $C_0$ and to an effective intraparticle solute diffusivity for such a gel-free particle given by the following expression:

$$\frac{D_f \varepsilon_p}{\tau}$$

Inasmuch as E is the ratio of a term proportional to the actual intraparticle flux (i.e., $D_s \cdot q_0$) to a comparable term proportional to the flux that would be predicted for a gel-free porous support particle, then —absent other considerations (i.e., steric exclusion by the gel)—the expected value of E would be of order unity or less. In contrast, the flux enhancement factor E achievable through the present invention can be substantially greater than unity—and significantly greater than the E values provided by prior-art media—as shown in more detail below.

The degree of flux enhancement achievable through the present invention is particularly unexpected when the steric exclusion of the polymer network or gel present within the pores of the composite media support is taken into account in the prediction of the expected intraparticle solute flux. In particular, the presence of the gel within the support particle's pores reduces the porous volume (or, alternatively, the effective area for diffusion) that is accessible to molecules diffusing within it. It is this steric effect of the gel in reducing this expected intraparticle flux which the second flux enhancement factor E* is designed to capture. In particular, one of ordinary skill would expect the solute to diffuse into the composite particle no more rapidly that it would diffuse into a support particle filled with a non-interactive gel; in this case, the expected rate of mass transfer would again be proportional to the solution-phase solute concentration driving force $C_0$—but the effective intraparticle diffusivity would be smaller, as given by the following expression:

$$\frac{D_f \varepsilon_p^*}{\tau}$$

where $\varepsilon_p^*$ is the species-dependent inclusion porosity. Inasmuch as E* is the ratio of a term proportional to the actual intraparticle flux (i.e., $D_s \cdot q_0$) to a term proportional to the predicted or expected intraparticle flux taking steric exclusion of solute by the gel into account, one of ordinary skill might reasonably anticipate that composite media would provide E* values of order unity or lower. However, the composite media of the present invention are characterized by much larger E* values that differentiate them from prior-art composite media.

Support-related factors

The parameter $\tau$ is the tortuosity factor characteristic of the skeletal matrix of the composite media support particle. The parameter $\tau$ is related to the additional distance that a solute has to diffuse in the tortuous pores of the support as compared to how far it would have to diffuse in "straight" pores or in free solution. Because the pore walls of the composite media of the support particle do not allow diffusion through them, the solute cannot diffuse directly from some point A to some point B; instead the solute has to move from point A somewhat away from a straight line to point B to point C—and only then to point B. In contrast, in free solution, the solute can diffuse directly from point A to point B. This tortuosity therefore decreases the effective concentration gradient and thus the speed at which the biological molecule to be separated diffuses into the particle skeleton, thus reducing the performance of the media. Values for the tortuosity parameter $\tau$ can be determined by first measuring solute mass transfer rates of a very small solute in a porous support particle and then extracting an effective intraparticle diffusivity from these rates, taking the support geometry and the solution-phase solute concentration driving force into proper account. Next, one measures the void fraction $\varepsilon_p$ of the porous support (e.g., by mercury porosimetry or other standard method as discussed further below). The tortuosity parameter $\tau$ is then obtained by dividing the product of the solution-phase solute diffusivity $D_f$ (see below) times the support particle porosity $\varepsilon_p$ by the effective intraparticle solute diffusivity. This tortuosity factor can be measured with a small diffusive probe, or by comparing the intraparticle diffusivity of a series of variously sized molecules. See Coffman, J. L., Ph.D. Thesis, University of Wisconsin, 1994. $\tau$ usually has a value of from about 2 to about 6 for many chromatographic materials (See Coffman, J. L., Ph.D. Thesis, University of Wisconsin, 1994). A conservative $\tau$ value of 2 has been assumed in E and E* calculations presented here.

$\varepsilon_p$ is the fractional void volume of the skeleton of the composite media, which also represents the effective area open for diffusion of the biological molecule of interest in the skeleton of the composite. It represents the fraction of the volume of the support particle occupied by pores before those pores are at least partially filled with the polymer network. This parameter $\varepsilon_p$ can be measured by mercury intrusion by those skilled in the art.

The parameter $\varepsilon_p^*$ is the species-dependent inclusion porosity or species-dependent void volume fraction of the composite media with the polymer network present within the pores. It measures the volume fraction of the composite particle (i.e., gel plus support particle) that is accessible to the solute and is related to the partition coefficient of the biological molecule under nonbinding conditions, that is, conditions under which the solute interacts with the polymer network or gel within the pores of the support exclusively via steric interactions. This factor, $\varepsilon_p^*$, also represents the effective area open for diffusion of the biological molecule of interest in the supported gel.

For composite media, $\varepsilon_p^*$ derives from two effects. One is the fact that the support or skeleton of the composite media takes up space in the media, leaving only the void volume $\varepsilon_p$ accessible to solute. Secondly, this porous volume contains gel in the composite media of the invention, and the polymer molecules of this gel can be arranged in such a way as to create a fine three-dimensional mesh or network. In the media of the present invention, this effective mesh size is very small, on the order of the size of biological molecules of interest. Since the mesh size is so small, many biological molecules of interest do not fit well into, and are thus at least partially excluded from, the effective pores or spaces between the polymer molecules comprising the mesh, which further and significantly reduces the solute accessible volume and thus makes $\varepsilon_p^*$ significantly smaller than the support void fraction $\varepsilon_p$. This steric exclusion by the polymeric network can be theoretically described by the so-called Ogston equation $$\frac{\varepsilon_p^*}{\varepsilon_p} = \exp\left[-\phi\left(1 + \frac{a}{a_f}\right)^2\right]$$

where $a$ is the Stokes radius of the biological molecule of interest, $a_f$ is the effective radius of a polymer strand, and $\phi$ is the volume fraction of the polymer forming the network. For the present invention, $\phi$ is the order of several percent (e.g. preferably, 0.03 to 0.20); $a_f$ is equal to 6.5 Å for polyacrylamide gels. The Stokes radius for globular proteins can be obtained from the correlation $$a_f = 0.875(MW)^{1/3}$$

where MW is the molecular weight of the globular protein of interest (Tyn and Guseck, Biotech. Bioeng., 35, pp. 327–338 (1990)).

Solute-related factors $D_s$ is the experimentally determined effective intraparticle diffusivity of the biological molecule to be separated from the mixture. More specifically, $D_s$ is the effective intraparticle diffusivity based on the gradient in total intraparticle macromolecule concentration as the driving force. $D_s$ represents the proportionality constant between the flux and the concentration gradient of sorbed protein at any point in the media.

The effective intraparticle diffusivity can be measured in several ways, including a batch uptake method, a shallow bed chromatography method, and by analyzing breakthrough curves on a long column as discussed further below. The parameter $q_0$ is the intraparticle concentration of the biological macromolecule of interest in the composite media at equilibrium with a solution-phase solute concentration of $C_o$.

$D_f$ is the diffusion coefficient in free solution of the biological molecule of interest. Df may be measured in a variety of ways, for instance, by light scattering, pulsed field gradient NMR, and diffusion cell methods. There are also published correlations available for this parameter, as described by Tyn and Guseck, *Biotech. Bioeng.*, 35, pp. 327–338 (1990).

Comparisons

Table I compares values of E determined for some embodiments of the present invention (first three entries) with values of E calculated for certain prior art composite media systems. Methods for the determination or estimation of the various parameters that comprise E are discussed in more detail in the Examples section below.

TABLE I

| PROTEIN/MEDIUM | TYPE OF DATA ANALYZED | REFERENCE | E |
|---|---|---|---|
| BSA/HyperD (present invention) | Uptake/shallow bed | experimental | 101 |
| Ova/HyperD (present invention) | Uptake/shallow bed | experimental | 76 |
| β-Lac/HyperD (present invention) | Uptake/shallow bed | experimental | 140 |
| BSA/DEAE-Spherodex | Breakthrough | Schanen[1] | 1.7 |
| Hb/DEAE-Spherodex | Breakthrough | Schanen[1] | 1.2 |

[1]V. Schanen, K. T. Chue, G. Grevillot, Proceedings of the 9th International Symposium on Preparative and Industrial Chromatography, Chair: M. Perrut, Societe Francaise de Chimie, 1992.

Since the original uptake data for the prior art reference in Table I were not available, we used the values of $D_s$ reported by the authors and obtained from analysis of breakthrough curves. The porous silica supports used in the manufacture of both Spherodex and HyperD are similar and made by the same manufacturers, and they have similar values of porosity $\epsilon_p$ (0.65) and tortuosity t (2.0).

The unexpectedly superior mass transfer performance of the present invention is better described by taking into account the expected steric effects of the gel present within the pores of the composite medium. This is done through the diffusional flux enhancement factor E*

$$E^* = \frac{D_s q_0}{\frac{D_f \varepsilon_p^*}{\tau} C_0}$$

where the effect of steric exclusion of the solute by the gel on the expected intraparticle solute flux is included in the species-dependent inclusion porosity $\epsilon_p^*$ as described above. E* quantitates the degree of flux enhancement through the area that is actually open for diffusion through the supported gel, as opposed to E, where the open area for diffusion is presumed to be the entire open area of the skeleton or porous support. In accordance with the present invention, E* is generally above about 3 and is preferably at least about 50 and most preferably at least about 300.

Table II compares values of E* determined for some embodiments of the present invention (first three entries) with values of E* calculated for certain prior art composite media systems.

TABLE II

| PROTEIN/MEDIUM | TYPE OF DATA ANALYZED | REFERENCE | E* |
|---|---|---|---|
| BSA/HyperD (present invention) | Uptake/shallow bed | experimental | 7600 |
| Ova/HyperD (present invention) | Uptake/shallow bed | experimental | 2600 |
| β-Lac/HyperD (present invention) | Uptake/shallow bed | experimental | 921 |
| BSA/DEAE-Spherodex | Breakthrough | Schanen[1] | 1.7 |
| Hb/DEAE-Spherodex | Breakthrough | Schanen[1] | 1.3 |

[1]V. Schanen, K. T. Chue, G. Grevillot, Proceedings of the 9th International Symposium on Preparative and Industrial Chromatography, Chair: M. Perrut, Societe Francaise de Chimie, 1992.

The composite media of the present invention are superior to prior-art composite media by virtue of their enhanced intraparticle mass transfer rates. That is, the values of E and E* determined for the HyperD media of the present invention are typically an order of magnitude or more higher than those of prior-art supported-gel composite media (see Tables I and II).

The composite media of the present invention are also superior to prior-art non-composite media (e.g., unsupported gels, porous silica, etc.) not only by virtue of their high mass transfer efficiency but also by virtue of their improved rigidity and other mechanical properties which enable their use in high-speed chromatographic operations. Table III.A shows the values of the flux enhancement factor E computed for non-composite media, while Table III.B shows the calculated values of the second flux enhancement factor E* for the same prior art media.

TABLE III.A

| PROTEIN/MEDIUM | METHOD | REFERENCE | E |
|---|---|---|---|
| Ova/Sephacel | Breakthrough | [1]Shiosaki | 9 |
| Myo/Sephacel | Breakthrough | [1]Shiosaki | 8 |
| BSA/Sephadex A-50 | Uptake | [2]Tsou | 7 |
| BSA/Sephadex A-50 | Breakthrough | [3]Pinto | 2 |
| BSA/Chitosan | Uptake | [4]Yoshida | 2 |
| BSA/Q-Spherosil | Uptake | [5]vanderWiel | 0.1 |
| BSA/Q-Spherosil | Breakthrough | [6]Schanen | 0.3 |
| Hb/Q-Spherosil | Breakthrough | [6]Schanen | 0.2 |
| BSA/Cellulose | Uptake | [7]Graham | <0.1 |

[1]A. Shiosaki, M. Goto, T. Hirose, J. Chromatography, 679, p1–9, 1994.
[2]H. S. Tsou, E. E. Graham, AIChE J. 35, p1959, 1985.
[3]N. G. Pinto, E. E. Graham, Reactive Polymers, 5, p49–53, 1987.
[4]H. Yoshida, M. Yoshikawa, T. Kataoka, AIChE J. 40, p2034–2944, 1994.
[5]J. P. van der Weil, Ph.D. Thesis, Academish Boekin, Centrum Delft, Nederlands, 1989.
[6]V. Schanen, K. T. Chue, G. Grevillot, Proceedings of the 9th International Symposium on Preparative and Industrial Chromatography, Chair: M. Perrut, Societe Francaise de Chimie, 1992.
[7]E. E. Graham, C. F. Fook, AIChE J., 28, p245, 1982.

TABLE III.B

| PROTEIN/MEDIUM | TYPE OF DATA ANALYZED | REFERENCE | E* |
|---|---|---|---|
| Ova/Sephacel | Breakthrough | [1]Shiosaki | 35 |
| Myo/Sephacel | Breakthrough | [1]Shiosaki | 33 |
| BSA/Sephadex A-50 | Uptake | [2]Tsou | 208 |
| BSA/Sephadex A-50 | Breakthrough | [3]Pinto | 67 |
| BSA/Chitosan | Uptake | [4]Yoshida | 2 |
| BSA/Q-Spherosil | Uptake | [5]vanderWiel | 0.1 |
| BSA/Q-Spherosil | Breakthrough | [6]Schanen | 0.3 |

TABLE III.B-continued

| PROTEIN/MEDIUM | TYPE OF DATA ANALYZED | REFERENCE | E* |
|---|---|---|---|
| Hb/Q-Spherosil | Breakthrough | [6]Schanen | 0.2 |
| BSA/Cellulose | Uptake | [7]Graham | <0.1 |

[1]A. Shiosaki, M. Goto, T. Hirose, J. Chromatography, 679, p1–9, 1994.
[2]H. S. Tsou, E. E. Graham, AIChE J. 35, p1959, 1985.
[3]N. G. Pinto, E. E. Graham, Reactive Polymers, 5, p49–53, 1987.
[4]H. Yoshida, M. Yoshikawa, T. Kataoka, AIChE J. 40, p2034–2944, 1994.
[5]J. P. van der Weil, Ph.D. Thesis, Academish Boekin, Centrum Delft, Nederlands, 1989.
[6]V. Schanen, K. T. Chue, G. Grevillot, Proceedings of the 9th International Symposium on Preparative and Industrial Chromatography, Chair: M. Perrut, Societe Francaise de Chimie, 1992.
[7]E. E. Graham, C. F. Fook, AIChE J., 28, p245, 1982.

The values of E and E* in Tables III.A and III.B were calculated from values of $D_s$ and from $D_e$ values reported in the literature cited. Methods for the determination or estimation of the various parameters that comprise E and E* are discussed in more detail in the Examples section below. More particularly, methods for the estimation of E and E* based on published effective diffusivities $D_e$ (i.e., reduced data as opposed to raw uptake or breakthrough data) for various prior-art media are presented in the Examples that follow.

Without wishing to be limited by theory, it is currently believed that the media of the present invention provide large values for E and E* compared to prior conventional media because of enhanced mobility of the biological molecules of interest inside the media. This enhanced mobility results, it is believed, from the fact that when the biological molecule of interest interacts with and/or adsorbs or binds to the media of the present invention, the biological molecule remains appreciably mobile. Moreover, because the binding capacity $q_0$ is high, the concentration of bound but mobile protein (or other biological on non-biological solute) can be high—leading to large and steep intraparticle concentration gradients that give rise to large intraparticle diffusional fluxes. In many conventional media, when the biological molecule of interest adsorbs or binds to the media, the biological molecule for the most part ceases to move and remains essentially stationary. This decreases the total flux of biological molecules into conventional sorbents as compared to the flux of molecules into the composite media described herein.

Under strong adsorption conditions, it may be that only one molecule out of one or several thousands of molecules will be unbound or unadsorbed in both conventional media and in the composite media described herein. This means that under strong binding conditions favorable for separating biological molecules, perhaps only about one of a thousand solute molecules are appreciably mobile in conventional media, the rest being bound or adsorbed to the matrix in a relatively immobile or stationary condition. Under similar binding conditions, however, a majority if not nearly all of the solute molecules within the media of the present invention are mobile, whether or not they are interacting with the polymeric network. The consequence of this is that in the media of the present invention, the driving force for intraparticle diffusion is much larger, as large as a thousand or more times larger, than is the driving force for intraparticle diffusion in conventional media. In fact, the driving force for diffusion in the media of the present invention can approach the gradient in the total intraparticle solute concentration. The driving force for most conventional media, on the other hand, is limited to the unbound solute concentration, which is significantly smaller. Since the driving force for diffusion in the media of the present invention is so much higher, the flux is significantly greater into the present media than into conventional media. That the (biological) solute molecule of interest can remain mobile while interacting with and/or adsorbed or bound to the chromatographic media of the present invention to the extent described herein was entirely unexpected.

The total protein concentration in the supported-gel media, the gradient of which is the driving force for mass transfer in the present invention, is a function of the static capacity of the media for the particular solute of interest. This static capacity depends on, among other factors, the salt concentration, the pH, the properties of the gel, and the solute species. When the static sorption capacity is significantly higher than the free solution concentration, then the rate of intraparticle mass transfer in the above-mentioned composite particle will be largely independent of the external solution concentration. One consequence of this is that the flux enhancement factors E and E* characteristic of the invention get progressively higher as the external solution concentration decreases. This is due to the fact that the flux enhancement factors E and E* compare the rate of intraparticle diffusion within the gel-containing composite particle of the present invention with the rates of diffusional mass transfer within, respectively, (i) the porous support particle devoid of gel or (ii) the porous support particle containing gel that interacts only sterically with the solute of interest. Since the driving force decreases with decreasing external solution concentration in the latter instances, whereas in the present media the driving force remains relatively independent of the external solution concentration, E and E* increase with decreasing $C_o$. This effect makes the composite media of the present invention valuable for efficiently adsorbing biological macromolecules from dilute solutions of the biological macromolecule of interest. Dilute solutions of biological macromolecules dominate the biotechnology industry, as fermentation, for instance, produces relatively low concentrations of the biological macromolecule of interest. Solute concentrations vary widely from application to application, but $C_0$ values are generally at least 1 $\mu$g/mL, more typically are or order 10 $\mu$g/mL or greater, and preferably are or 100 $\mu$g/mL and larger. Similar considerations apply to the use of the composite media in recovery of valuable metals from dilute solutions and in the capture of environmental pollutants, and other applications.

Without wishing to be limited by theory, it is believed that the high capacity of the present composite media and the high mass transfer rates in that media are aided by the flexibility of the gel polymer network incorporated into the rigid porous support. The flexibility of the gel allows for the solute to penetrate the gel by either the solute pushing aside the polymeric network gel in order to get by, or by the gel molecules spontaneously moving to form a hole into which the solute can move. This is particularly important where the effective diameter of the solute is large in comparison with the characteristic length between the polymer chains that form the three-dimensional polymeric gel network—e.g., where the solute is a biological macromolecule like a protein, a polysaccharide, a polynucleotide or others. It is further believed that the three-dimensional nature of the gel and the small mesh size of the gel contribute to the high capacity of the media and to the ability of large solutes (e.g., biological macromolecules) to move even while interacting with the active portions, e.g., ion exchange sites or affinity sites, of the gel. The fineness of the polymeric network mesh also means that these sites are in close proximity, such that molecules can move from site to site quickly, without having to desorb and/or move very far between sites.

Without wishing to be limited by theory, one can speculate that the confinement of the polymeric gel network of the present invention within the pores of the rigid porous support matrix may also be important to the operation of the invention—in particular, to the features of high binding capacity and high intraparticle diffusive mass transfer rates. If the polymeric gel network of the present invention were "free" or unconfined—as opposed to being confined within the porous volume of the support matrix of the present composite media, then the as polymerized gel swells or increases in volume several-fold when exposed to dilute aqueous solutions of the sort normally encountered in biochromatography; this swelling results from, e.g., in ion-exchange gel media or in affinity media where the affinity to the biological macromolecule of interest is to some extent ionic (such as heparin affinity or lysine affinity for example), the repulsion of fixed charges of like sign on the polymeric network. This swelling effectively "dilutes" the binding sites (thus reducing binding capacity), and, under certain circumstances, may make it necessary for a solute to disassociate from one binding site before diffusing to and interacting with another. In contrast, with the confined gel of the present invention, the polymeric network cannot swell, despite the strong interaction of the fixed ionic charges. As a consequence, binding capacity remains high. Moreover, the regions of ionic interaction overlap, and a solute of opposite charge (such as a biological macromolecule) can move freely within the entire polymer network while interacting electrostatically with more than one ionic group or affinity site of the three dimensional polymeric network. That is, a sorbed solute molecule may not have to dissociate from one binding "site" before diffusing to and interacting with another, since the binding "sites" are not necessarily discrete in the polymeric network contained within the composite media of the present invention. This has clearly unexpected advantages in terms of enhanced intraparticle mass transfer rates.

Passivated supports

In a preferred embodiment, the present invention provides a passivated composite sorbent particle comprising a porous solid matrix having interior and exterior surfaces and innate (i.e., inherently present) groups that render the matrix susceptible to undesirable non-specific interaction with biological molecules, and a polymer network derived from a passivation mixture comprising effective amounts of a main monomer, a passivating monomer different from the main monomer, and a crosslinking agent, the mixture having been allowed to come into intimate contact with the surfaces of the matrix for a sufficient period of time such that on polymerization of the mixture the innate groups of the matrix become deactivated, resulting in the minimization or substantial elimination of the above-mentioned undesirable non-specific interactions.

The passivated composite media of the present invention are further characterized by reversible high sorptive capacity and high intraparticle diffusive mass transfer rates for biological molecules including proteins. Furthermore, the passivated composite media of the present invention enjoy exceptional chemical stability on exposure to strongly acidic or alkaline media and/or strong oxidizing solutions such as those that are frequently utilized during cleaning of industrial manufacturing equipment.

A wide variety of non-passivated porous solid matrices are amenable to passivation by the general method of the present invention. These porous matrices include, but are not limited to, (i) mineral oxide supports, (ii) "stabilized" mineral oxide supports rendered chemically resistant to leaching by the application of thin protective coatings of alkali-stable metal oxides or hydrophobic polymers to their surfaces, and (iii) porous matrices comprised solely of organic/polymeric materials, in particular hydrophobic polymers.

Polymeric supports

Where porous matrices comprised of hydrophobic polymer substrates (as opposed to mineral oxide matrices) are concerned, it is a further object of the present invention to reduce the non-specific binding associated with exposure of such hydrophobic polymer surfaces to proteinaceous solutions.

The passivating monomers of the present invention adsorb upon (and consequently cover) the hydrophobic groups on the surface by virtue of their containing long-chain saturated hydrocarbons, olefinic hydrocarbon groups, aromatic groups, or like hydrophobic domains that interact with and become appreciably bound to their hydrophobic counterparts on the matrix surface as a consequence of the hydrophobic-hydrophobic interaction between them.

Coated particles

The methods of the present invention can be advantageously applied to the passivation of chromatographic media comprised of porous mineral oxide particles (e.g., silica and alumina), the interior and exterior surfaces of which have previously been coated with a thin, protective layer of a coating polymer. This protective polymer coating is applied for the purpose of improving the chemical stability of the underlying mineral oxide material (e.g., against leaching or other chemical decomposition at alkaline, acidic, or strongly oxidizing conditions). For example, strongly alkaline aqueous media (e.g., 0.5M sodium hydroxide solutions) are commonly used to clean chromatographic media, and conventional silica media can suffer significant weight loss (of order 50%) associated with leaching of the material over repeated cleaning cycles (e.g., 100 cycles).

The leaching of such unprotected mineral oxide media gives rise to a number of problems, not the least of which is loss of mechanical integrity of the particle and a consequent increase in the back pressure exhibited by columns packed with particles of the material. The problem of leaching can be addressed to some extent by using porous matrices characterized by lower surface areas (e.g., 5–10 $m^2/g$), but this is generally undesirable insofar as sorption capacity is often reduced by a corresponding amount.

The approach to substrate stabilization taken in one embodiment of the present invention involves coating the alkaline-sensitive porous mineral oxide substrate matrix with a soluble polymer that substantially encapsulates the mineral oxide matrix and thereby minimizes or prevents contact between the mineral oxide substrate and potentially destructive chemical cleaning solutions (e.g., caustic). The protective polymer coating is applied in the form of a thin surface layer upon the pore wall surfaces in order to avoid significantly decreasing the porous volume or blocking the mouths of pores. The protective polymer coating layer is readily applied, for example, by (i) first dissolving the protective polymer (e.g., polystyrene) in a suitable organic solvent to form a coating solution, (ii) subsequently impregnating the porous mineral oxide matrix with the solution, and then (iii) finally evaporating or otherwise removing the organic solvent.

While it has been discovered that this process of depositing protective polymer coatings upon the porous surfaces of mineral oxide (and particularly silica) matrices can significantly stabilize these materials by sharply reducing their rates of chemical leaching, the approach has the important disadvantage of rendering the porous surfaces of the coated and protected matrices hydrophobic and thus prone to cause excessive non-specific binding of proteins by adsorption. (This is precisely the same problem noted above in connection with entirely polymeric porous support matrices.) However, this problem can be successfully addressed by the methods of the present invention in the same way as the non-specific binding of strictly polymeric support matrices can be reduced —i.e., by passivation in a process of oriented polymerization. More particularly, these composite chromatographic media (i.e., supports comprised of mineral oxide substrates that have been stabilized by the application of thin protective polymer coatings) can be passivated against excessive non-specific binding by incorporating passivating ("neutralizing") monomers capable of associating with and consequently deactivating innate non-polar hydrophobic groups exposed on the matrix surface. The passivating monomers useful in this embodiment of the present invention adsorb upon (and consequently cover) the hydrophobic groups on the surface by virtue of their containing long-chain saturated hydrocarbons, olefinic hydrocarbon groups, aromatic groups, or like hydrophobic domains that interact with and become appreciably bound to their hydrophobic counterparts on the matrix surface as a consequence of the hydrophobic-hydrophobic interaction existing between them.

Matrix dimensions

Typically, the present invention utilizes base matrices having the following characteristics: an initial average particle size ranging from about 5 to about 1000 microns; an initial porous volume ranging from about 0.2 to about 2 $cm^3$/gram; an initial surface area ranging from about 1 to about 800 $m^2$/gram; and an initial pore size ranging from about 50 to about 6000 angstroms. Preferably, the base matrix is characterized by: an initial average particle size ranging from about 10 to about 300 microns, although passivated supports having narrow particle size ranges, such as about 15–20, about 15–25, about 30–45, about 50–60, about 80–100, and about 100–300 microns, are most preferred. Preferred ranges for other characteristics include an initial porous volume ranging from about 0.8 to about 1.2 $cm^3$/gram; an initial surface area ranging from about 10 to about 400 $m^2$/gram; and an initial pore size ranging from about 1000 to about 3000 angstroms. The density of the porous solid matrix obviously varies with its chemical nature, being higher for mineral oxide (e.g., silica) substrates and lower for polymeric ones (e.g., polystyrene).

The size exclusion limit of the composite media varies somewhat but generally falls in the range of about 500 to about 2,000,000 Daltons, preferably, 50,000 to about 500,000. The sorptive capacity can also be manipulated, depending on the amount of main monomer incorporated in the polymer network, and ranges between about 1 milligram to about 300 milligrams of solute or biological molecule per unit volume (mL) of media—preferably at least about 50 mg/mL, and most preferably about 100 mg/mL.

Polymerization

In particular embodiments of the present invention, the polymerization of the passivation mixture is effected in the presence of an effective amount of a pore inducer. A number of additives are suitable as pore inducers. Also, the polymerization of the passivation mixture can be effected in the presence of an effective pore-inducing amount of a polar solvent.

According to the present invention, polymerization is effected in the presence of an effective amount of a polymerization initiator. Polymerization begins as is known in the art, e.g., with agitation, exposure to heat, or exposure to a sufficient amount of radiant energy.

The present invention provides further passivated media in which the main monomer of the polymer network comprises a vinyl monomer having at least one polar substituent. Such substituent may further be ionic, non-ionic, ionizable, or in the case of a vinyl monomer having more than one polar substituent, such substituents may be a combination of such substituents. It is preferred in affinity chromatography that the main monomer on polymerization, as part of the polymer network, have an affinity for a preselected biological molecule. However, the further modification of the polymer network to incorporate specific ligands capable of binding to biological molecules of interest is not precluded.

It should be apparent to one of ordinary skill in the art that the substituent(s) on the passivating or neutralizing monomer responsible for the "deactivation" (i.e., the reduction in the capacity of the innate groups of the non-passivated porous solid matrix to interact in a non-specific manner with biological molecules) should be tailored to the nature of the non-specific interaction to which the non-passivated porous solid matrix is susceptible. In essence, neutralizing monomers are provided which can interact with the innate groups of the matrix surfaces in the same manner as the non-specific interaction (e.g., electrostatically, via hydrogen bonding or both in the case of mineral oxide matrices—or via hydrophobic-hydrophobic interaction in the case of synthetic polymeric matrices). Hence, substituents can be polar, cationic, anionic or hydrophobic depending on the particular application at hand. For example, suitable neutralizing monomers for porous mineral oxide matrices comprise a vinyl monomer having at least one polar ionic or ionizable substituent. In one embodiment of the present invention, the substituent has the capacity to bear a positive charge. In particular, such neutralizing monomers are selected to provide near-surface passivating regions and polymer networks that are effective in deactivating polar groups on the surfaces of non-passivated matrices (e.g., in deactivating hydroxyl groups on the surfaces of porous mineral oxide matrices).

Suitable passivating monomers for use in the passivation of hydrophobic polymer surfaces will typically comprise vinyl monomers having at least one substantially non-polar or hydrophobic substituent. This is true whether the polymer is present as a protective surface coating on a mineral oxide matrix or as the bulk, structural material in the case of a porous polymeric chromatographic support matrix. In one embodiment of the present invention, this substituent comprises a hydrocarbon-rich functional group or moiety that imparts hydrophobicity to a portion of the passivating monomer.

In general, the hydrophobic character will result from the presence in the passivating monomer of a saturated (e.g., aliphatic) or unsaturated (e.g., aromatic) hydrocarbon substituent, and may further be described as straight-chain, branched, cyclic, or heterocyclic. Long-chain alkyl functional groups are particularly useful as substituents in this class of passivating monomers, which further contain one or more vinylic, acrylic, acrylamide, or allylic monomers. These passivating monomers are typically employed at concentrations in the reaction mixture of from about 0.1 to 1%.

Crosslinking agents useful in the present invention comprise vinyl monomers having at least one other polymerizable group, such as a double bond, a triple bond, an allylic group, an epoxide, an azetidine, or a strained carbocyclic ring.

Separations

The methods of the present invention are effective to isolate or separate a broad range of biological molecules, including peptides, polypeptides, and proteins (such as insulin and human or bovine serum albumin), growth factors, immunoglobulins (including IgG, IgM, and therapeutic antibodies), carbohydrates (such as heparin) and polynucleotides (such as DNA, RNA, or oligonucleotide fragments).

Eluent solutions suitable for use in the present invention are well known to those of ordinary skill in the art. For example, a change in ionic strength, pH or solvent composition may be effective in "stepwise" elution processes. Alternately, eluent solutions may comprise a salt gradient, a pH gradient or any particular solvent or solvent mixture that is specifically useful in displacing the preselected biological molecule. Such methods are generally known to those engaged in the practice of protein chromatography. Still another object of the present invention relates to a chromatographic method for the separation of biological molecules comprising passing a sample containing a mixture of biological molecules through a column packed with the composite media disclosed herein.

By virtue of their superior mass transfer characteristics and high binding capacity, it is anticipated that the composite particles of the present invention will also find use outside the field of biochromatography—both as adsorbents (in chromatographic and other types of sorption processes, e.g., for the recovery of environmental pollutants, valuable metals, etc.) and as solid-phase supports for the conduct of chemical reactions, the immobilization of reactants and catalysts, and the capture of reaction products.

The main monomer

A primary component of the passivation mixture of the present invention is the main monomer. The appropriate amount of main monomer (or other solute) for use in the present invention is expressed as a percentage equal to the number of grams of main monomer per 100 mL of monomer solution (percent weight/volume). For purposes of the present discussion, the volume of the monomer solution is effectively the volume of the solution of a passivation mixture containing main monomer, neutralizing monomer, and crosslinking agent. Appropriate concentrations of the main monomer range from about 5% to about 50% (i.e., 5–50 grams of main monomer per 100 mL of monomer solution). Preferred concentrations of the main monomer are from about 7% to about 20%.

For purposes of this application, the main monomer is defined as including any monomer known to those skilled in the art which can be utilized for the preparation of an adsorbent useful in a chromatographic separation (e.g., affinity, ion-exchange, and the like). Such monomers include, but are not limited to, non-ionic monomers, ionic monomers, hydrophilic monomers, hydrophobic monomers, and reactive monomers. Reactive monomers are monomers having special functional groups that enable them to react chemically with other molecules that are subsequently immobilized irreversibly on the polymer network. This procedure is the basis of affinity chromatography, the chemically attached molecule being referred to as the "ligand." The main monomers of the present invention can be aliphatic, aromatic or heterocyclic; however, they must possess a polymerizable double bond; for example, the main monomers can be acrylic, allylic, vinylic or the like.

More specifically, anionic polymers are used to create anionic sorbents (i.e., cation-exchange media). The functional groups (i.e., the substituents on the vinyl monomer) are preferably: carboxylic groups (e.g., acrylic acid, N-acryloyl-aminohexanoic acid, N-carboxymethylacrylamide), sulfonate groups (e.g., acrylamidomethyl-propane sulfonic acid), or phosphate groups (e.g., N-phosphoethyl-acrylamide).

Cationic polymers used to create cationic sorbents may contain the following functional groups: substituted amino groups (e.g., diethylaminoethyl methacrylamide, diethylaminoethyl acrylamide, methacrylamidopropyltrimethylammonium halide, triethylaminoethyl acrylamide, trimethylaminoethyl methacrylate, polyethyleneglycol dimethacrylate, dimethylaminoethyl methacrylate, polyethyleneglycol divinyl ether, or polyethyleneglycol methacrylate), or heterocyclic amines (e.g., 2-vinylpyridine, vinylimidazole, 4-vinyl-pyridine). Nonionic polymers may be comprised of: acrylamide, hydroxy-containing acrylamide derivatives (e.g., N-tris-hydroxymethyl-methylacrylamide, methylolacrylamide, dimethylacrylamide, 2-hydroxyethylacrylamide, N-acryloyl-morpholine), methacrylamide, hydroxycontaining methacrylamide derivatives, heterocyclic neutral monomers (e.g., vinylpyrrolidone, N-acryloylmorpholine), or hydroxy-containing acrylates and methacrylates (e.g., hydroxyethyl acrylate or hydroxyethyl methacrylate, hydroxyphenyl methacrylate, 4-vinylphenol, and 2-hydroxypropyl acrylate).

Hydrophobic monomers useful in creating sorbents for hydrophobic chromatography include octylacrylamide or -methacrylamide, phenyl-acrylamide, butyl-acrylamide, benzyl-acrylamide, and triphenylmethyl-acrylamide.

Activated monomers useful in creating preactivated sorbents (i.e., those that can be further derivatized directly with a "ligand") for affinity chromatography include glycidylacrylate or -methacrylate, acrolein, acrylamidobutyraldehyde dimethylacetal, acrylic-anhydride, acryloyl chloride, N-acryloxysuccinimide, and allyl-chloroformate.

The passivating monomer

The passivation mixture further comprises an appropriate amount of a passivating or neutralizing monomer capable of neutralizing the non-specific adsorption properties of innate sites on the surface of the porous solid support. In the case of silica, the acidic character of innate silanol groups proves problematic during separations, and it is thus desirable to neutralize these silanol groups. The amount of neutralizing monomer to be used is preferably an amount sufficient to counteract approximately up to an equivalent number of Si-OH groups present at the exterior and interior surfaces of the support. The amount of neutralizing monomer, again expressed as a percentage (weight/volume), should be about 0.5% to about 6% (w/v), preferably about 1.5% to about 3% (i.e., about 1.5–3 grams of neutralizing monomer per 100 mL of monomer solution).

Suitable neutralizing monomers for use in the present invention may be monomers bearing a positive charge at a neutral pH; examples include monomers containing a cationic amine group, such as substituted amines or pyridine and the like. The cationic neutralizing monomers must have at least one double bond, such as vinyl, acrylic, or allylic monomers.

To counteract the acidic character of silica and its tendency to form hydrogen bonds, cationic monomers or monomers which are able to engage in hydrogen bonding (dipolar interactions) are also useful as neutralizing monomers in a particular embodiment of the present invention.

Preferred neutralizing cationic monomers of the present invention include, but are not limited to, diethylaminoethyl acrylamide, diethylaminoethyl methacrylamide, diethylaminoethyl methacrylate, methacrylamidepropyltrimethyl ammonium halide, triethylaminoethylacrylamide, triethylaminoethyl methacrylate and copolymers thereof.

Polyoxyethylene-containing monomers can also be used. This latter group can interact with polar groups (via hydrogen bonding). Preferred neutralizing monomers able to induce hydrogen bonding are polyoxyethylene monomers like poly(ethylene glycol)$_n$-dimethylacrylate, where "n" is between about 50 and about 1000.

Preferred neutralizing hydrophobic monomers include, but are not limited to, N-alkylacrylamide in which the alkyl groups are branched, N-alkylacrylamide methylene chains having up to about 20 carbon atoms in the alkyl moiety, and N-arylacrylamide derivatives, like N-benzylacrylamide, N,N-(1,1-dimethyl-2-phenyl)ethyl-acrylamide, N-triphenylmethylacrylamide, or N,N-dibenzylacrylamide. Specific representative passivating monomers useful in treating polymeric or polymer-coated matrices include, but are not limited to, N-tert-octylacrylamide (TOA), N-(1-methylundecyl)acrylamide (MUA), N-(1,1,3,5-tetramethyl) octylacrylamide (TMOA), Triton-X-100-methacrylate (TWMA), and polyethyleneglycol-dimethacrylate (PEGDMA). Hydrophobic adsorption sites present on the internal surfaces of some organic (i.e., polymeric) porous matrices like polystyrene—or on protective polymer coatings deposited on porous mineral oxide matrices—are neutralized using hydrophobic passivating monomers incorporating these aromatic and aliphatic hydrophobic moieties or substituents.

The crosslinking agent

To the mixture comprising the neutralizing and main monomers, a bifunctional crosslinking agent is added. The crosslinking agent allows the three-dimensional insoluble polymeric network to form within the pore volume of the porous matrix. In the absence of the crosslinker called for in this invention, the polymer formed would be linear and thus soluble. The amount of crosslinking agent should be about 0.1% to about 10% (w/v). Alternatively, the amount of crosslinking agent can be calculated based on the total weight of main monomer and neutralizing monomer in use. Preferably, the amount of crosslinking agent is from about 3 to about 10 percent by weight of the total weight of main and neutralizing monomers.

The crosslinking agents used in the present invention are acrylic, vinylic or allylic monomers that possess at least two polymerizable functional groups. Preferred crosslinking agents have at least two double bonds and include, but are not limited to, N,N'-methylene-bis-acrylamide, N,N'-methylene-bismethacrylamide, diallyl tartardiamide, allyl methacrylate, diallyl amine, diallyl ether, diallyl carbonate, divinyl carbonate, divinyl ether, 1,4-butanediol divinylether, and 1,3-diallyloxy-2-propanol.

Optionally, but preferably, urea may also be added to the monomer solution prior to impregnation of the porous solid matrix. Urea may be incorporated into the monomer solution at a wide range of concentrations—from a few percent based on the weight of the porous support matrix (e.g., a few grams of urea per hundred grams of porous support) up to concentrations of 15–20 wt % and higher (e.g., 15 to 20 grams and more of urea per 100 grams of support). Incorporation of urea into the monomer solution results in an improvement of the properties of the polymeric gel network that is eventually obtained.

The porous solid matrix

Thereafter, the mixture is admixed with a porous solid matrix, thereby filling the pores of the matrix. As regards inorganic support materials, suitable porous mineral oxide matrices used in the present invention include but are not limited to silica, alumina, transition metal oxides (including but not limited to titanium oxide, zirconium oxide, chromium oxide, and iron oxide), any other similar ceramic materials including silicon nitride and aluminum nitride, and mixtures and combinations thereof. The preferred mineral moieties of the present invention include silica, zirconium oxide, and titanium oxide. The most preferred mineral moiety is porous silica of a particle size of about 5 $\mu$m to about 1000 $\mu$m, having a porous volume of about 0.2 to about 2 cm$^3$/g, a pore size of about 50 to about 6000 Å, and a surface area of about 1 to about 800 m$^2$/g. At this time, most all of the aqueous solution will have been absorbed by the mineral support.

After filling the pores of the porous mineral oxide matrix, (e.g., silica) with the aqueous solution of monomers (preferably, the volume of the solution expressed in mLs is approximately equal to the weight in grams of the silica matrix), the mixture is placed in a non-aqueous dispersing medium. Suitable non-aqueous media include non-polar organic solvents known to those skilled in the art. Such non-aqueous media for suspending the treated matrix may include, but are not limited to, mineral and vegetable oils, aromatic solvents, aliphatic low molecular weight solvents, or chlorinated solvents. The most preferred non-aqueous media include toluene, methylene chloride, and hexane.

Thereafter, a polymerization starter is added to the mixture, now in a non-aqueous medium, in order to initiate polymerization of the monomers within the silica pores. The concentration of initiator (expressed as percent weight per volume of initial monomer solution) is from about 0.1% to about 2%, preferably about 0.8% to about 1.2%.

It should be apparent to those of ordinary skill that certain initiators are best dissolved in aqueous media while others can be dissolved in organic media. Hence, depending on the solubility characteristics of a particular initiator or combination of initiators, the polymerization initiator can be added to the initial solution of passivation mixture prior to addition of that mixture to the porous solid matrix. In particular, an initiator combination of ammonium persulfate and tetramethylethylenediamine (TMEDA) can be introduced separately. One component (the water-soluble persulfate salt) is combined with the aqueous mixture of main monomer, neutralizing monomer, and crosslinking agent, while the other component (TMEDA) is combined with the non-aqueous dispersing medium.

It should be noted that the persulfate/TMEDA combination is particularly useful because TMEDA displays appreciable solubility in water. Hence, in the dispersion comprised of the treated support, water and non-aqueous solvent, the TMEDA is able to penetrate the pores of the treated support and thereby initiate polymerization, particularly upon heating.

Typical polymerization initiators known to those skilled in the art can be used in the present invention. For instance, these initiators may be capable of generating free radicals. Suitable polymerization starters include both thermal and photoinitiators. Suitable thermal initiators include, but are not limited to, ammonium persulfate/ tetramethylethylenediamine (TMEDA), 2,2'-azobis-(2-amidinopropane) hydrochloride, potassium persulfate/ dimethylaminopropionitrile, 2,2'-azobis(isobutyro-nitrile), 4,4'-azobis-(4-cyanovaleric acid), and benzoyl-peroxide. Preferred thermal initiators are ammonium persulfate/ tetramethyethylenediamine and 2,2'-azobis (isobutyronitrile). Photoinitiators include, but are not limited to, isopropylthioxantone, 2-(2'-hydroxy-5'-methylphenyl) benzotriazole, 2,2'-dihydroxy-4-methoxybenzophenone, and riboflavin. It is further contemplated that riboflavin be used in the presence of TMEDA. When using the combination of persulfate and tertiary amine, the persulfate is preferably added prior to the addition of the non-aqueous medium, since persulfate is much more soluble in water than in non-aqueous dispersing media.

In another embodiment, the polymerization step can take place in the presence of a pore inducer. The pore inducers of the present invention allow polymerization of the gel to take place while maximizing the accessibility of the interior volume of the composite media. Suitable pore inducers, also referred to as porogens, used in the present invention include, but are not limited to, polyethylene glycols, polyoxyethylenes, polysaccharides such as dextran, and polar solvents. Polar solvents include those commonly used in chemical synthesis or polymer chemistry and known to those skilled in the art. Suitable polar solvents include alcohols, ketones, tetrahydrofuran, dimethylformamide, and dimethysulfoxide. Preferred polar solvents are ethanol, methanol, dioxane, and dimethysulfoxide.

Porous polymeric matrices amenable to passivation by the methods of the present invention include, but are not limited to, polystyrene, polysulfone, polyethersulfone, various cellulose esters (e.g., cellulose acetate, cellulose nitrate), polyolefins (e.g., polyethylene and polypropylene), polyvinylacetate (and partially hydrolyzed versions thereof), polyacrylates, polyvinylidene fluoride, polyacrylonitrile, polyamides, polyimides, and various blends, mixtures, and copolymers thereof. Procedures for the manufacture of porous particles and other structures (e.g., microporous membranes) from such polymers are generally known in the art.

Where the polymer surface to be passivated is in the form of a thin, protective coating residing upon the pore walls of mineral oxide substrate that is thus stabilized against leaching, the polymer will generally consist of a linear, high-molecular-weight polymer capable of being dissolved in a suitable organic solvent. For example, a coating solution of linear polystyrene (e.g., with an average molecular weight 400 kilodaltons) is conveniently prepared by dissolving the polymer in a chlorinated hydrocarbon such as methylene chloride. Typical concentrations of polymer in the coating solution range from about 2% (w/v) to about 20% (w/v). The ideal concentration is determined by achieving a balance between effectiveness in preventing or minimizing leaching of the mineral oxide substrate (which argues for higher polymer concentrations) and the constriction of pores and partial loss of porous volume (and sorption capacity) that can occur at higher polymer concentrations. Where protective coatings of polystyrene are deposited on porous silica, a polystyrene concentration of about 10% (w/v) is preferred. The coating is applied by first impregnating the porous support with the solution of protective coating and then removing the solvent vehicle by evaporation.

Certain modifications to the passivation procedures employed with porous mineral oxide matrices are indicated where the exposed surface of the porous matrix to be passivated is a polymeric one—i.e., in those cases where (i) the porous support particle is fashioned entirely of polymer or (ii) a mineral oxide matrix is protected by a stabilizing polymer coating. In these situations, polymerization of the passivating mixture by the process described above, entailing the dispersion of the porous particles (impregnated with aqueous monomer solution) in a non-aqueous (i.e., "oil-phase") dispersing medium, has certain disadvantages. The problems stem from the fact that the surfaces of polystyrene-coated silica and other polymer-coated mineral oxide matrices are predominantly hydrophobic and compatible with oil-phase dispersing agents that would otherwise be used in the polymerization step. Oil-phase dispersing media are prone to penetrating the pores of matrices that present exposed polymeric surfaces, and the presence of oil inside the pores causes various manufacturing problems (e.g., partial solubilization of the coating polymer, difficulty in effecting removal of the oil from the pores, etc.).

Accordingly, a modified polymerization procedure is advantageously employed where polymeric surfaces are to be passivated, which procedure entails a so-called "dry polymerization" procedure as opposed to that described above involving an oil-phase dispersing medium. In particular, the porous matrix impregnated with aqueous passivating mixture (i.e., monomer solution) undergoes the polymerization reaction while in the form of an apparently "dry" and free-flowing powder, typically agitated (e.g., by stirring or fluidization) in a closed, inert (e.g., nitrogen) atmosphere. The dry polymerization reaction is typically conducted at a temperature from about 60 to 90° C., at a pressure of 1 to 2 bars, and for a period ranging from about 2 hours to overnight.

Suitably "dry" but monomer-solution-impregnated powders can be prepared by adding the aqueous passivating mixture in a careful, metered fashion (e.g., dropwise) to the porous matrix, so that little or no excess liquid-phase passivating mixture is present. The incorporation of organic cosolvents (e.g., ethanol, dimethylsulfoxide, and the like) in the monomer mixture assists the process of wetting the polymeric or polymer-coated mineral oxide matrix by the predominantly aqueous passivation mixture. For example, the crosslinking agent is conveniently added to the final monomer mixture in the form of an aqueous 10% ethanol solution.

Because no oil-phase is present as a dispersing medium in this embodiment of the invention, the initiators (i.e., polymerization catalysts) employed in this dry polymerization process are necessarily water-soluble and are generally thermally activated. A representative thermally-activated polymerization initiator is azo-bis-amidinopropane.

In yet another aspect of the invention, polymeric and polymer-coated mineral oxide matrices may be treated with hydrophilic polymers such as polyoxyethylene (POE) and polyvinylpyrrolidone (PVP) prior to effecting the polymerization and crosslinking of the monomer solution within the pores of the support. Treatment in this manner can be effective in reducing non-specific-binding interactions with proteins even in the absence of the oriented polymerization of hydrophobically binding passivating monomers present in the monomer solution. Without wishing to be limited as to theory, it is believed that such high-molecular-weight passivating polymers are initially adsorbed upon the surfaces of the polymeric or polymer-coated mineral oxide matrix. Upon polymerization of the monomer solution, these polymers become substantially immobilized by the formation of an interpenetrating polymer network. That is, the POE or PVP polymer becomes entrapped in a "sandwich" type of structure between the pore-wall surface and the three-dimensional polymer lattice that occupies most of the porous volume.

The composite media

In all cases, i.e., whether the porous matrix is comprised of a mineral oxide, a polymer-coated and thus stabilized mineral oxide, or a polymer, the polymerization process of the present invention creates a three-dimensional lattice or crosslinked polymer network that extends away from the pore-wall surfaces of the porous solid matrix. Again, not wishing to be limited by theory, it is believed that this polymer network is comprised of a thin passivating region or layer that ideally interacts with the surface of any non-specific adsorption sites of the solid support (e.g., silanols in the case of silica) covalently linked with a three-dimensional structural polymer lattice that can (but need not necessarily) substantially fill the porous volume. In a preferred embodiment, the three-dimensional shape of the polymer lattice is believed to be substantially identical to the shape of the pore which it fills (see FIG. 5), with any passivating layer oriented adjacent to and continuous (i.e., covalently linked) to the three-dimensional polymer lattice that extends away from the matrix surface. This configuration prevents "neutralizing" or "deactivating" pieces of the polymer network from eluting from the composite media during regular use—for example, when it is exposed to vigorous washing or cleaning conditions, such as high acidic pH, high alkaline pH, high ionic strength, and strong oxidizing conditions. This crosslinked polymer network creates a novel chromatographic sorbent which can then be used, for example, in a process for separating and purifying various biomolecules, including macromolecules.

Figure 3A:
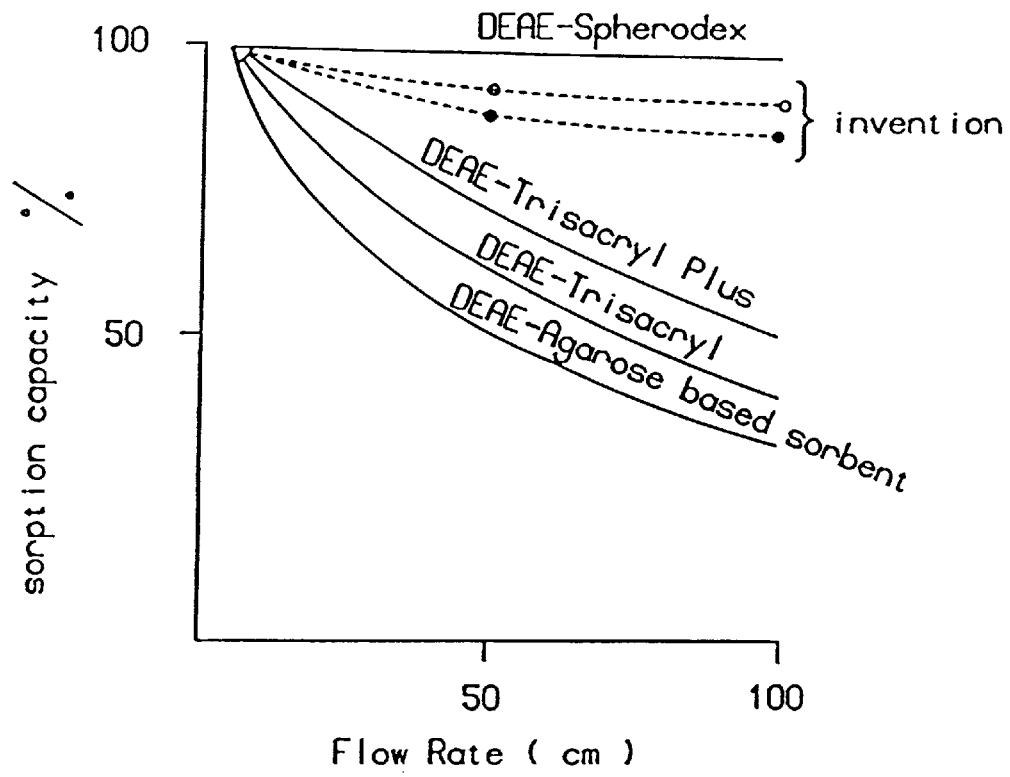
FIG. 3.A shows a graph of useful relative sorption capacity versus flow rate for various porous supports including the porous supports of the present invention passivated with a cationically charged polymer network (i.e., a passivated porous support useful as an anion-exchange resin).
Figure 3B:
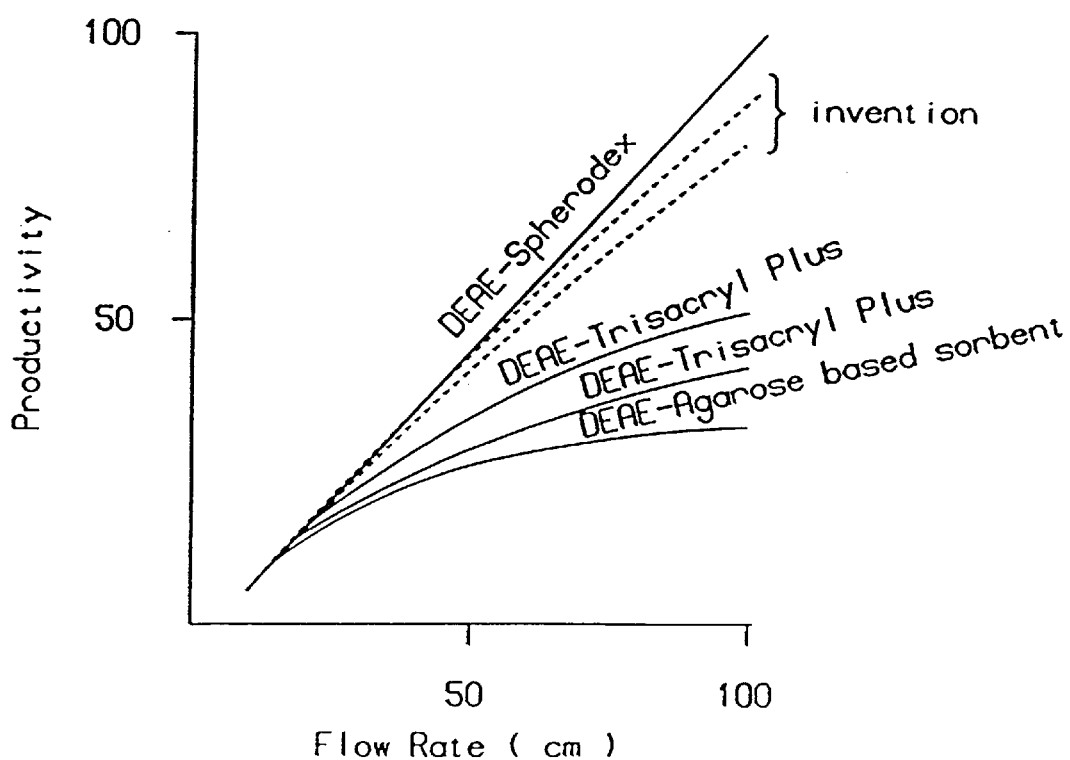

Indeed, it has been surprisingly discovered that the composite media of the present invention manifest chromatographic characteristics that are unparalleled under several criteria, particularly in terms of dynamic sorptive capacity as a function of flow rate and high intraparticle mass transfer rates. In particular, whereas the great majority of porous materials suffer a marked decrease in useful sorptive capacity as flow rates increase (e.g., at flow rates of about 50 cm/hr or greater), the passivated porous supports of the present invention show little decrease in useful sorptive capacity from a static condition up to flow rates approaching several hundred centimeters per hour. Compare, for example, the behavior of prior art "gel"-type materials with the supports of the present invention, as illustrated in the graphs of FIG. 3A, 3B, and 4 (described further in Example 16).

Figure 4:
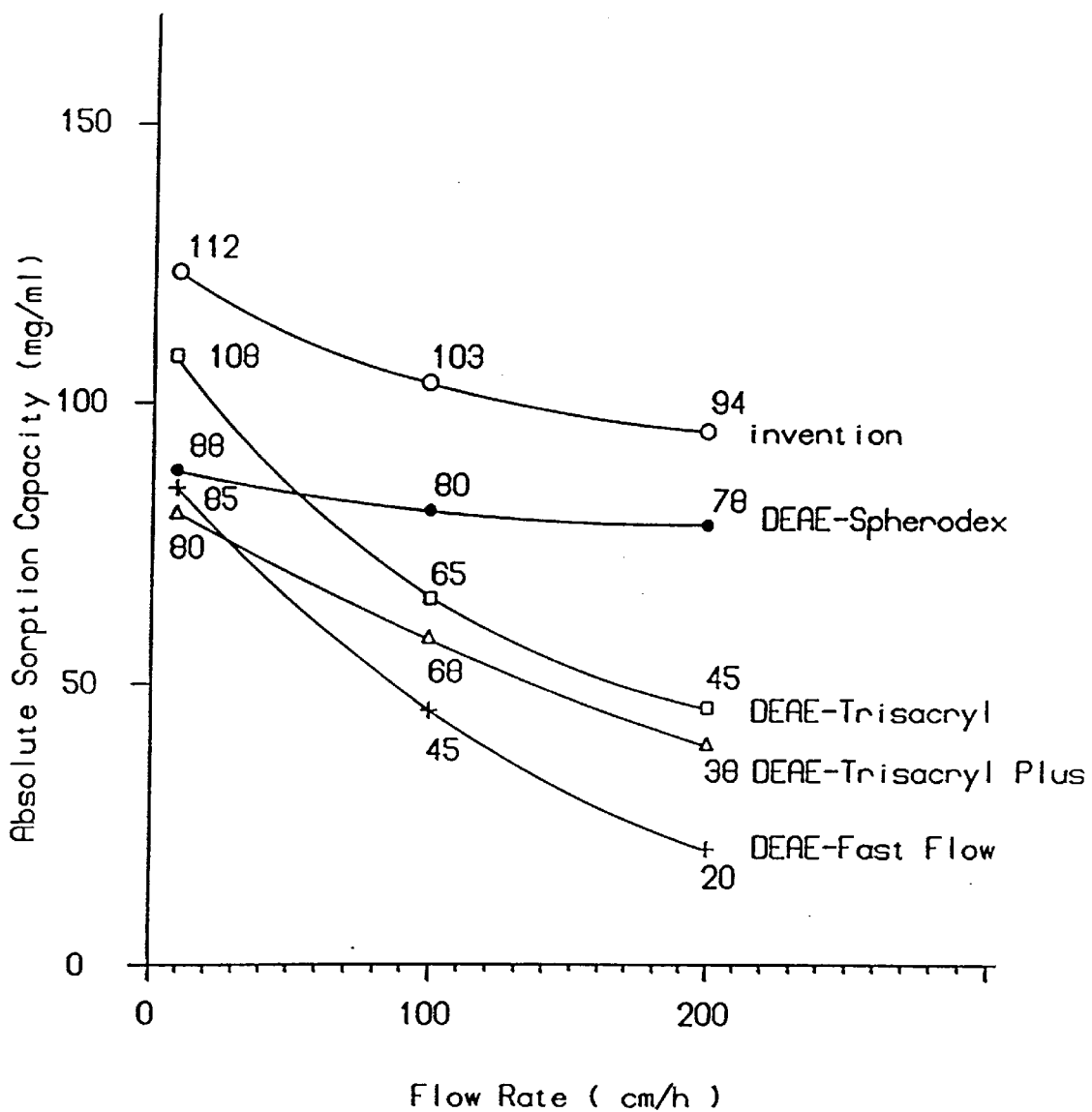
FIG. 4 shows a graph of the absolute sorptive capacity (in mg/mL) as a function of flow rate of a variety of solid supports, including a passivated porous support of the present invention.

Moreover, the absolute capacities of the composite media of the present invention are considerably greater than those attained with other types of chromatographic media (e.g., Spherodex™) Thus, as shown in FIG. 4, a plot of the absolute capacity vs. flow rate of various chromatographic media unambiguously shows that the composite media of the present invention combines a very high absolute sorption capacity (expressed as mg/mL) with a relative insensitivity to solution flow rates.

Figure 5:
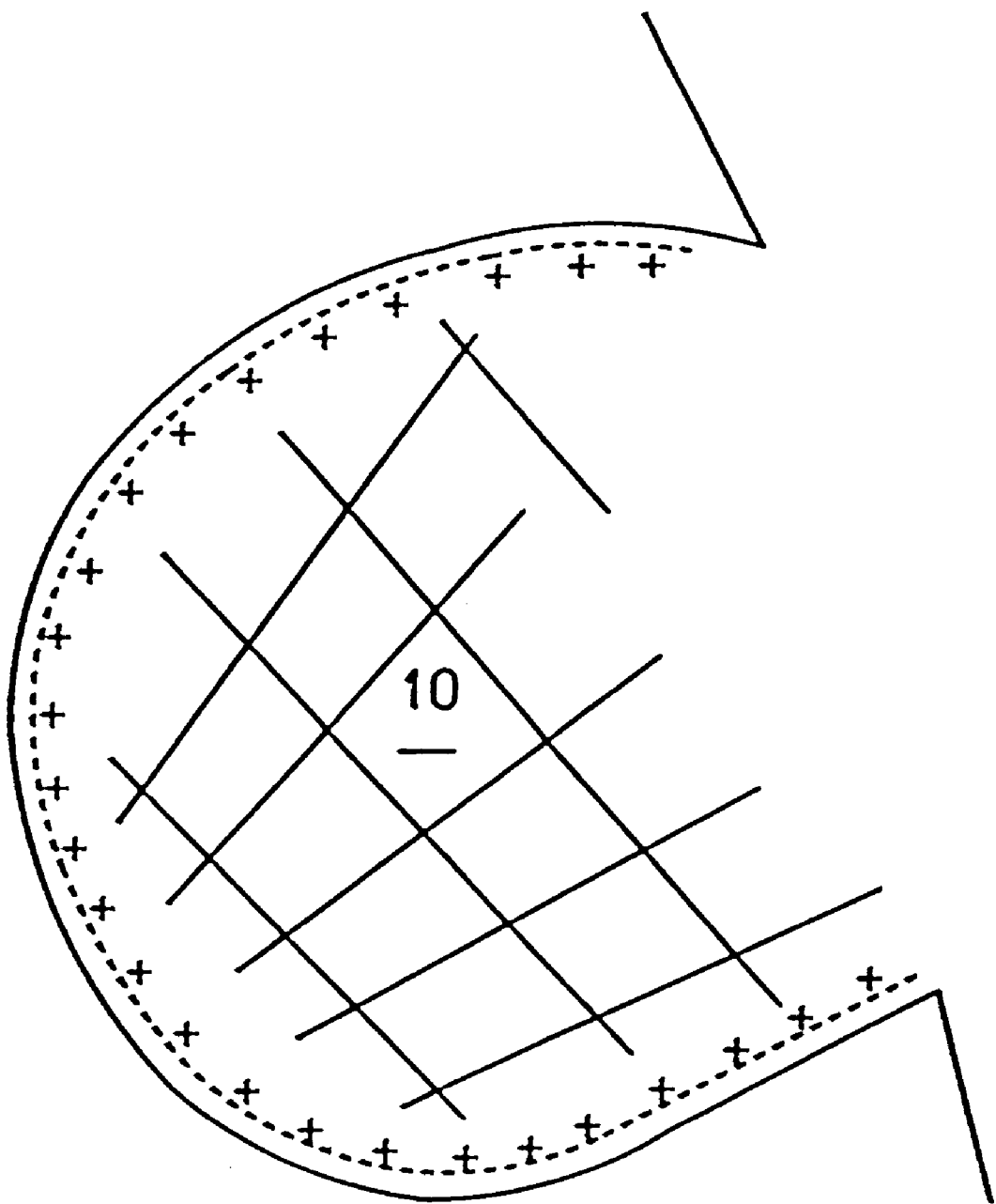
FIG. 5 is a schematic illustration of the putative architecture of the three-dimensional polymer network formed within and extending from the internal surfaces of an individual pore in a porous solid support upon polymerization of the passivation mixture of the present invention.

It is believed, without wishing to be limited by theory, that a flexible lattice structure comprised primarily of polymeric chains of repeating main monomer units is formed within the pores of the porous solid matrix. Very significantly, it is believed that the areas of the composite media available for desirable reversible interaction with biological molecules are not confined to the regions immediately adjacent to the surface of the pore as is the case when thin, substantially two-dimensional coatings are applied to porous surfaces in the manner of Steuck (U.S. Pat. No. 4,618,533) and Varady et al. (U.S. Pat. No. 5,030,352) as discussed in the Background of the Invention section above. Rather, it is believed that the gel-type polymeric network of the present invention extends outwardly into the pore volume itself in the manner of a three-dimensional preferably but not necessarily porefilling lattice, as opposed to a two-dimensional coating limited strictly to the pore wall surface area. A schematic diagram of such a structure, as it is thought to exist, is illustrated in FIG. 5, where a biological molecule of interest (depicted as a spherical object) is also shown interacting with the lattice. Furthermore, the presence of porogens (pore-inducers) in the passivation mixture is believed to promote creation of this three-dimensional polymer network.

It is further thought that such an extended polymer network contributes not only to the unusually high absolute sorptive capacity of the composite media of the invention as measured under static (i.e., no flow) conditions, but also permits rapid intraparticle mass transfer by diffusion and thereby allows the present invention to maintain high sorptive capacities largely independent of solution flow rates. It is thought that perhaps the flexible nature of the three-dimensional polymer network allows biological molecules to rapidly penetrate the polymer lattice and thereby efficiently interact with sorptive groups in the polymer network of the passivated porous support while maintaining their mobility even at high solution flow rates. The rapid and efficient mass transfer of biomolecules into and through this network avoids the decrease in useful or dynamic sorption capacity and resolution that are typical of conventional chromatographic media. With these conventional media, diffusion in the pores of the particle and/or materials coated thereupon or within them can be slow, leading to poor mass transfer rates and poor efficiency of the chromatographic process.

Separation and purification

Thus, a method of performing chromatographic separations characterized by high sustained sorptive capacity relatively independent of flow rate and rapid, efficient intraparticle mass transfer is achieved with composite media of the present invention, which media include a flexible three-dimensional network or lattice of crosslinked polymer chains extending within and throughout the pores of the support matrix.

The separation and purification process usually involves at least two steps. The first step is to charge a packed or fluidized bed column containing the preferably passivated composite adsorbent with a solution containing a mixture of biomolecules, at least one of which it is desired to separate and recover in at least partially purified form. The second step is to pass an eluent solution through the column to effect the release of the biomolecules from the column, thereby causing their separation.

"Stepwise" elution can be effected, for example, with a change in solvent content, salt content or pH of the eluent solution. Alternatively, gradient elution techniques well known in the art can be employed. For instance, proteins reversibly bound to cation exchange media can generally be eluted by increasing the pH to alkaline values (subject to limits associated with the chemical stability of the protein), and immunoglobulins bound to protein A or like adsorbents may be eluted by decreasing the pH to acidic values.

EXAMPLES

The invention is further defined by reference to the following examples that describe in detail the preparation of the passivated porous solid support and the methods of using the same. It will be apparent to those skilled in the art that many modifications, both to materials and methods, may be practiced without departing from the purpose and scope of this invention.

To better understand the procedures described in the following examples, several terms are defined for the benefit of the reader, below.

The passivation level is an estimation of the absence of non-specific adsorption of a strong cationic molecule like lysozyme, which characteristically forms very strong complexes with silanols on the silica surface.

Porosity factor is the ratio between elution volume ($V_e$) of a protein (e.g., BSA in our case) and the total volume ($V_t$)

of the packing bed determined under physicochemical conditions (e.g., high ionic strength) in which no interaction exists between the protein and the porous support.

Sorption capacity is the amount of adsorbed protein in "mg" per unit volume (mL) of passivated porous support bed determined under particular conditions:

for cationic sorbents: 50 mM Tris-HCl, pH 8.6.

for anionic sorbents: 50 mM Acetate, pH 6.5.

Ion exchange capacity is the number of ionizable groups in $\mu$eq per unit volume (mL) of passivated porous support bed determined by titration.

Example 1

Preparation of a porous cation-exchange resin 20 grams ("g") of acrylamidomethyl propane sulfonic acid (AMPS) sodium salt and 1 g of N,N'-methylene-bis-acrylamide (MBA) are dissolved in 50 mL of distilled water. 3 g of diethylaminoethyl methacrylamide, are added and then the pH of the total solution is adjusted to between 6 to 8 to make a final solution volume of the passivation mixture of 100 mL. To this solution of monomers, 500 mg of ammonium persulfate are added at room temperature.

While shaking, the solution of monomers is added dropwise to 100 g of porous silica (40 to 100 $\mu$m diameters, 1000 to 1500 Å pore diameter, 20 to 35 m$^2$/g surface area and 1 cm$^3$/g porous volume).

After 30 minutes of shaking, 250 mL of paraffin oil is added, the agitated suspension is heated at 60 to 70° C. and then 1 mL of N,N,N',N'-tetramethylethylenediamine is added.

After a few minutes, the exothermic polymerization reaction occurs. The resin is then separated by a chlorinated solvent and dried at room temperature. Lastly, the resin is washed extensively with dilute hydrochloric acid, dilute sodium hydroxide and 1M sodium chloride.

This cation-exchange resin shows the following characteristics:

A titration curve with an acidic pK due to the presence of sulfonic acid groups;

No presence of anionic groups which are oriented on the acidic silanols of the silica surface.

A number of acidic groups of 395 $\mu$eq/mL.

A sorption capacity for insulin in 70% ethanol of about 80 mg/mL.

An exclusion limit of about 30 Kd.

Example 2

Preparation of an anion-exchange resin 20 g of methacrylamidopropyltrimethyl ammonium chloride (MAPTAC) and 1 g of N,N'-methylene-bisacrylamide (MBA) are dissolved in 80 mL of distilled water and the pH of the solution is adjusted to 7.5. Separately, 1 g of ammonium persulfate is dissolved in 20 mL of distilled water. The two solutions were then mixed together at room temperature.

While shaking, the monomer solution is added dropwise to 100 g of dry porous silica (40–100 $\mu$m bead diameter, 1000–1500 Å porous volume, 20–35 m$^2$/g surface area and 1 cm$^3$/g porous volume).

After shaking for about 30 minutes, 250 mL of paraffin oil is added and the mixture heated at 60–70° C. 2 mL of N,N,N',N'-tetramethylenediamine is added to polymerize the monomer solution inside the silica pores.

The same recovery and washing steps are performed as those described in Example 1.

The obtained resin shows the following characteristics:

Ion-exchange capacity: 114 $\mu$eq of quaternary ammonium groups per mL of resin.

No visible presence of acidic (silanol) groups on titration curve.

No non-specific adsorption of cytochrome c at pH below its isoelectric point.

Sorption capacity for bovine serum albumin (BSA): 91 mg/mL resin.

Porosity factor for BSA ($V_e/V_r$): 0.52.

Example 3

Preparation of a second anion-exchange resin using different amounts of crosslinker Three 80 mL solutions each containing two monomers (MAPTAC and MBA) are prepared according to Example 2, using varying amounts of MBA: 0.5 g, 1 g and 2 g.

All other operations are identical to Example 2. The anion-exchange resins differ by the following properties:

| Amount of MBA: | 0.5 g | 1 g | 2 g |
| --- | --- | --- | --- |
| Ionic charges per mL of resin: | 36 $\mu$eq | 114 $\mu$eq | 218 $\mu$eq |
| Sorption capacity per mL (BSA): | 35 mg | 91 mg | 72 mg |

Example 4

Preparation of an anion-exchange resin using MBMA as a crosslinker 1 g of N,N'-methylene-bis-methacrylamide (MBMA) is dissolved in 50 mL of dimethylsulfoxide (DMSO). To this mixture 40 mL of an aqueous solution containing 20 g of MAPTAC is added.

While stirring, 1 g of ammonium persulfate previously dissolved in 10 mL of distilled water is added. The obtained monomer solution is then used to fill the silica pores (1 cm$^3$/g porous volume; 1200–1500 Å pore diameter) and the resin is prepared according to the previous examples except toluene is used as the non-aqueous solvent instead of paraffin oil.

The obtained anion-exchange resin shows the following characteristics:

Ion-exchange capacity: 201 $\mu$eq of quaternary amino groups per mL of resin.

Sorption capacity for BSA: 112 mg/mL.

No non-specific adsorption of cationic proteins like cytochrome c are present.

Porosity factor for BSA ($V_e/V_r$): 0.53

Example 5

Preparation of anion-exchange resins with a different amount of MBMA

Three different resins are prepared according to Example 4 with differing amounts of MBMA as a crosslinking agent.

When 100 mL of a DMSO-water solution is used, the amount of MBMA is varied as follows: 0.5 g, 1 g and 2 g. Paraffin oil is used as the non-aqueous (organic) solvent at 60° C.

The obtained resins show the following characteristics:

| Amount MAPTAC: | 20 g | 20 g | 20 g |
| --- | --- | --- | --- |
| Amount MBMA: | 0.5 g | 1 g | 2 g |
| Ionic charges per mL of resin: | 168 $\mu$eq | 212 $\mu$eq | 231 $\mu$eq |

-continued

| | | | |
|---|---|---|---|
| Sorption capacity per mL: | 114 | 106 | 76 |
| Porosity factors for BSA ($V_e/V_t$): | 0.52 | 0.52 | 0.51 |

It is demonstrated that the amount of crosslinking agent does not modify the porosity of the three dimensional polymer at least within the explored zone. The amount of ionic groups which depends on the amount of the main monomer remains also quite constant.

All of the above resins are stable to oxidizing agents, such as hypochlorites and peracetic acid.

Example 6

Preparation of strong cationic exchangers using silicas of different porosity 7 g of AMPS, 3 g of MAPTAC and 1 g of MBA are dissolved in 100 mL of distilled $H_2O$. 1 g of ammonium persulfate is then added and the solution is divided into two parts of 50 mL each. Separately, each solution is added to 50 g of dry silica having the following properties listed in the table below:

| | Particle Size | Surface Area | Porous Volume | Pore Diameter |
|---|---|---|---|---|
| Assay a | 40–100 µm | 25 m²/g | 1 cm³/g | 1250 Å |
| Assay b | 40–100 µm | 10 m²/g | 1 cm³/g | 3000 Å |

All other operations are performed according to Example 1.

The following are the final properties of the cationic exchangers:

| | Assay a | Assay b |
|---|---|---|
| Ionic charges per mL | 92 µeq | 89 µeq |
| Sorption capacity (cytochrome c) | 86 mg | 81 mg |
| Non-specific absorptions | negative | negative |

This example demonstrates that the ion-exchange and sorption capacity are independent of the nature of the silica. The choice of silica is more linked to its sensitivity to an alkaline media. For example, the alkaline sensitivity of silica having a surface area of 5 m²/g is 50% lower than when using a sample having a surface area of 25 m²/g.

Example 7

Preparation of cation-exchangers using different amounts of anionic monomer

The aqueous solutions of monomers (100 mL) are composed of:
 MAPTAC: 3 g (monomer to neutralize the silanol groups of silica)
 AMPS: 7 g and 10 g (varying amounts of anionic monomer)
 MBA: 1 g (crosslinker)

All other operations (mixing with silica, polymerization and recovery) are identical to those described on Example 1.

The final properties of the final cation-exchangers obtained are as follows:

| | | |
|---|---|---|
| Quantity of AMPS: | 7 g | 10 g |
| Ion-exchange groups per mL: | 92 eq | 147 µeq |
| Sorption capacity per mL (cytochrome c): | 86 mg | 120 mg |

This example confirms that when the amount of functionalized monomer in the initial solution is increased, the number of ion-exchange groups is proportionately higher. The sorption capacity for cytochrome c increases as well.

Example 8

Preparation of a strong cation-exchange resin with MBMA as crosslinker 0.5 g of MBMA are dissolved in 50 mL of DMSO while stirring. To this solution 30 mL of aqueous solution containing 10 g of AMPS is added as well as 6 mL of a 50% aqueous solution of MAPTAC.

The final volume is adjusted to 100 mL prior the addition of 1 g of ammonium persulfate at room temperature.

This solution of monomers is added dropwise to 100 g of dry porous silica to fill completely the available porous volume (1 cm³/g for a pore size of 1250 Å). The remaining operations are identical to the method described in Example 1. The final cation-exchange resin shows the following characteristics:

| | |
|---|---|
| Ion-exchange groups per mL of resin | 123 µeq |
| Sorption capacity for cytochrome c | 128 mg |
| Porosity factor for lysozyme | 0.82 |
| Resistance to oxidizing agents (NaOCl) | Excellent even at a concentrated form (1/10 dilution of commercial concentrated product.) |

Example 9

Preparation of a weak cation-exchange resin

In 60 mL of distilled water, 6 mL of a 50% aqueous solution of MAPTAC, 1 g of MBA and 10 mL of acrylic acid are dissolved.

The volume of the solution is then adjusted to 100 mL, the pH adjusted to about 4.5, and 1 g of ammonium persulfate is added at room temperature.

As described for other examples the solution of monomers is added to 100 g of porous silica and then polymerized in a non-aqueous water-immiscible solvent (e.g., paraffin oil, toluene, or methylene chloride).

The final characteristics of the resin are as follows:

Ion-exchange groups (carboxylates) per mL: 337 µeq

Sorption capacity for cytochrome c: 118 mg

Non-specific absorption: Excellent (chromatographic test)

Example 10

Preparation of non-ionic hydroxyl-containing resins for immobilization of biologicals The monomers comprising the initial solution are the following:

| | |
|---|---|
| Tris-hydroxymethyl-methyl-methacrylamide (THMMA) | Non ionic monomer |
| MAPTAC or DEAE methacrylamide | Cationic monomer to neutralize the silanol groups. |
| MBA | Crosslinking agent |

The composition of the solutions are:

|  | Assay a | Assay b | Assay c |
|---|---|---|---|
| THMMA | 10 g | 10 g | 20 g |
| MAPTAC | 1.5 g | — | 2.5 g |
| DEAE-methacrylamide | — | 2 g | — |
| MBA | 2 g | 3 g | 2 g |

All other operations (mixture with dry silica, polymerization and recovery) are identical to those described in previous examples.

The final characteristics of the resins are:

Good passivation of the silica surface. No significant amount of cationic proteins adsorbed in normal conditions of gel filtration.

$V_e/V_t$ for bovine albumin is respectively 0.71, 0.74 and 0.61.

After chemical modification the resin is utilized to immobilize either a dye (Cibacron Blue F3GA) or heparin.

Each affinity sorbent is very effective to purify human albumin and antithrombin III, respectively, in a single pass.

Example 11

Preparation of a cationic resin in the presence of polyethylene glycol as a pore inducer Two monomer solutions are prepared as described in Example 8. A solution of 10 g of polyethylene glycol 6000 is added to one.

Final volumes are adjusted to 100 mL, pH adjusted to about 7 and then 1 g of ammonium persulfate is added to both solutions.

The monomer mixture is added to porous silica (1200 Å pore diameter, 40–100 μm particle diameter, 25 m²/g surface area), polymerization and recovery are effected as described in previous examples. The obtained resins show the following characteristics:

|  | +PEG-6000 (10%) | PEG-6000 |
|---|---|---|
| MAPTAC | 20 g | 20 g |
| MBMA | 1 g | 1 g |
| CATIONIC GROUPS (μeq/mL) | 200 | 193 |
| SORPTION CAPACITY BSA | 112 | 127 |
| $V_e/V_t$ β-lactoglobulin | 0.578 | 0.511 |
| $V_e/V_t$ BSA | 0.548 | 0.513 |
| $V_e/V_t$ Immunoglobulins G | 0.495 | 0.481 |

This example demonstrates that, in spite of the same amount of initial material (similar number of ionic groups), the molecular scale porosity of the gel is influenced by the presence of PEG-6000.

The exclusion limit is actually larger when PEG is added.

Example 12

Further separations of protein mixtures by ionic resins

Two resins are used to show their ability to separate protein mixtures rapidly and efficiently:

a cationic resin (quaternary ammonium resin from Example 5).

an anionic sulfonated resin (see Example 8).

The cationic resin (201 μeq quaternary amino groups/mL) is packed in a column of 1 cm in diameter and 8 cm in length and then equilibrated with a 0.05M Tris-HCl buffer, pH 8.5. A sample containing 1 mg of cytochrome c, hemoglobin, beta-lactoglobulin and ovalbumin is injected and separated under a salt gradient.

The results of the separation of the four components is given below (FIG. 1A). Separation is achieved under a flow rate of 120 mL/hour.

The anionic resin (138 μeq $SO_3$ groups/mL) is packed in a column of 1 cm in diameter and 7 cm in length and then equilibrated with a 0.05M acetate buffer, pH 4.5. A sample containing ovalbumin, beta-lactoglobulin, cytochrome c, and lysozyme is injected and separated under a salt gradient.

Figure 1B:
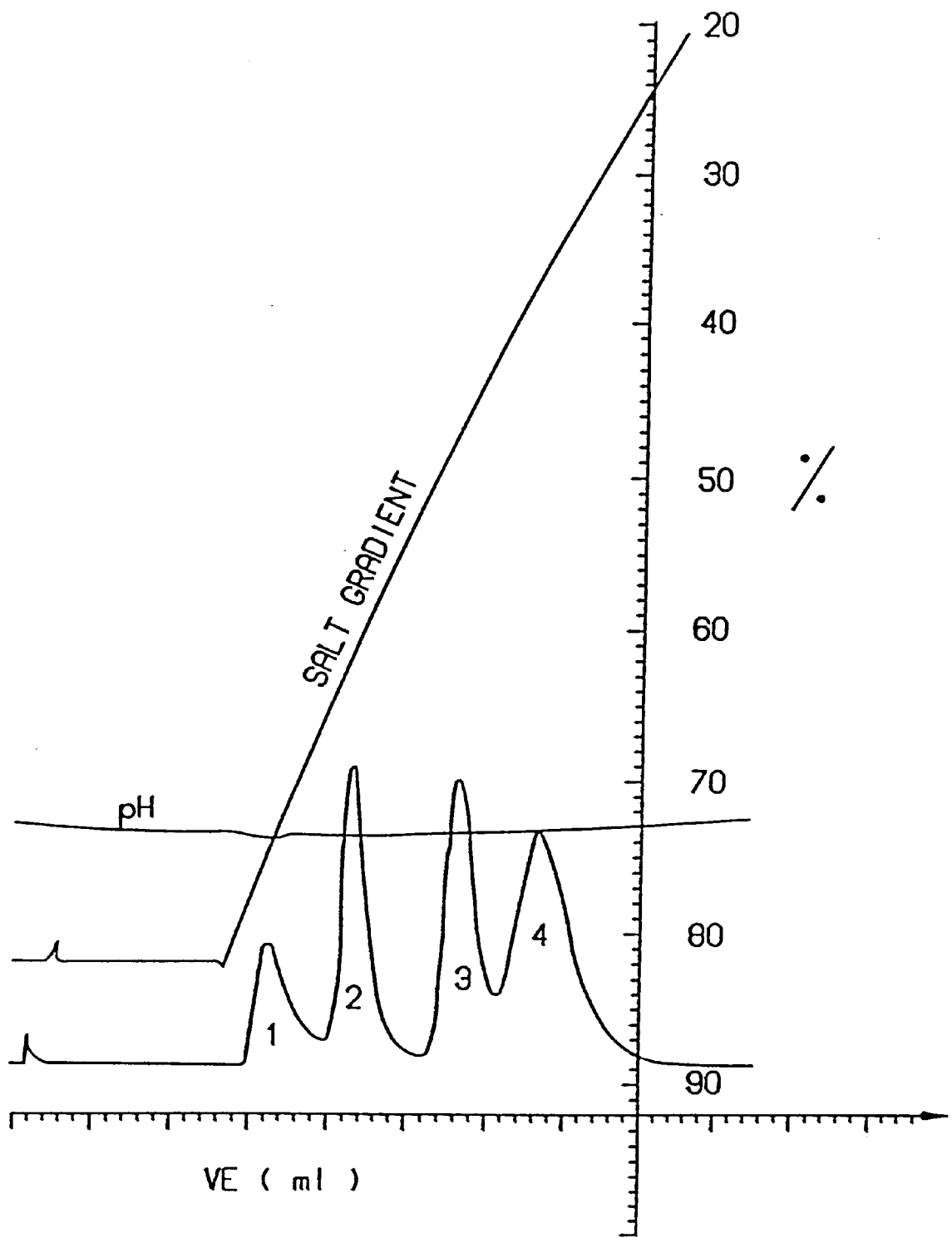

The result of the separation of four components is given below (FIG. 1B). Separation is achieved under a flow rate of 140 mL/hour.

Example 13

Demonstration of the need to neutralize the silanol group when preparing a cation-exchange resin Two aqueous solutions of monomer (100 mL each) are prepared according to Example 1 differing essentially by the presence of the cationic monomer MAPTAC.

Final composition of monomer solutions is as follows:

|  | Assay a | Assay b |
|---|---|---|
| AMPS | 10 g | 10 g |
| MBMA | 0.5 g | 0.5 g |
| MAPTAC | 3 g | 0 |

All the operations (mixing with silica, polymerization and recovery) are identical to those described in the above-mentioned examples.

The final properties of the obtained cation exchangers are as follows:

|  | Assay a | Assay b |
|---|---|---|
| Ion-exchanger groups per mL | 123 μeq | 118 μeq |
| Sorption capacity per mL (cyt. c) | 128 mg | 77 mg |
| Separation efficiency | excellent | no separation |

Figure 2A:
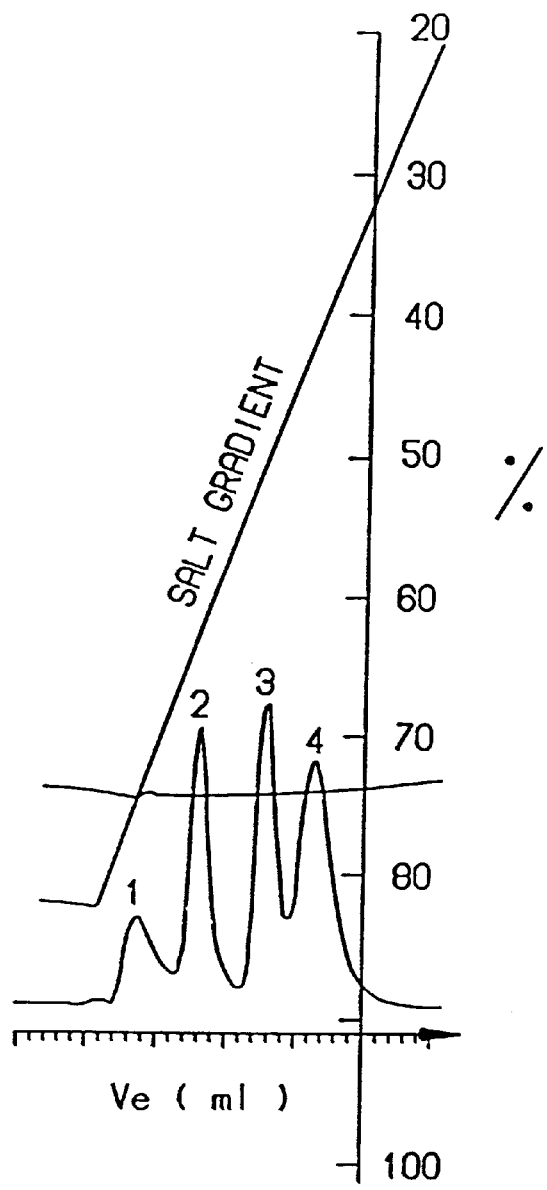
FIG. 2.A represents a comparison between the chromatographic separations of a protein mixture consisting of (1) ovalbumin, (2) beta-lactoglobulin, (3) cytochrome c, and (4) lysozyme using an anionic passivated porous support.
Figure 2B:
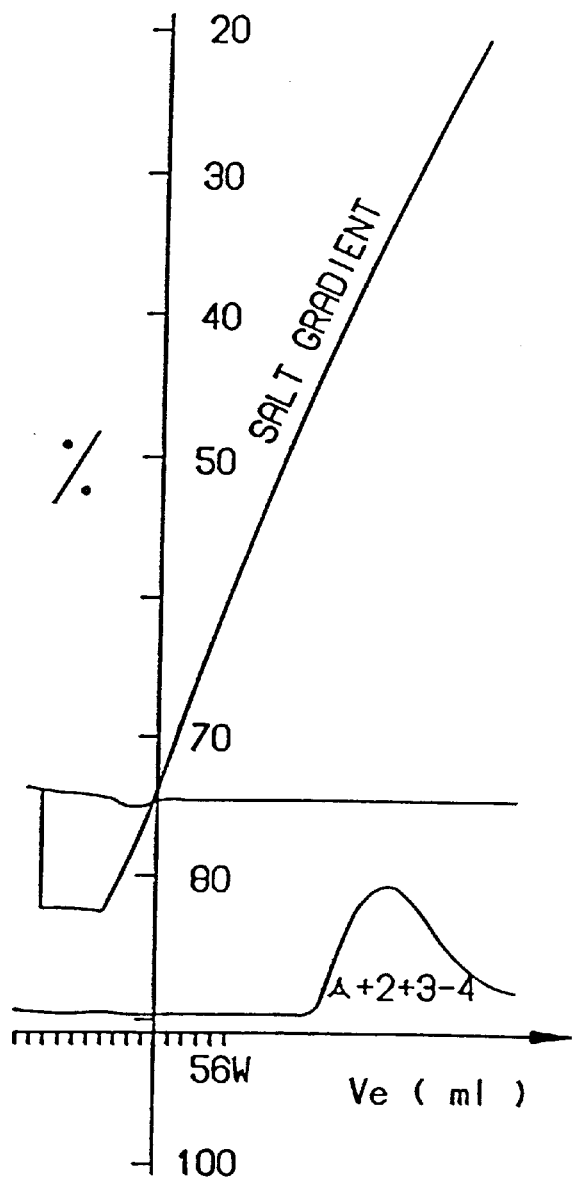

These results, which are graphically depicted in FIGS. 2a and 2b, demonstrate the necessity to neutralize acidic silanols that disturb the separation mechanism.

Example 14

Influence of the amount of cationic monomer on the passivation of silica surface To demonstrate that the amount of cationic monomer necessary to neutralize silanol groups (passivation is proportional to the surface area) a series of trials are effected with porous silicas with different surface area.

Silicas chosen are the following:

|  | Silica X 015 | Silica X 075 |
|---|---|---|
| Surface area per g | 25 m² | 100 m² |
| Porous volume per g | 1cm³ | 1cm³ |
| Bead size | 40–100 microns | 40–100 microns |

Trials are performed using different amounts of MAPTAC (cationic monomer) copolymerized with a non-ionic acrylic monomer (THMMA).

After polymerization, the degree of passivation is estimated by the measurement of non-specific adsorption of lysozyme.

TABLE IV

COMPOSITION OF POLYMERS AND RELATED ANALYTICAL RESULTS

| Type of silica | X 075 | X 075 | X 075 | X 075 | X 075 |
|---|---|---|---|---|---|
| Surface area/g | 100 m² | 100 m² | 100 m² | 100 m² | 100 m² |
| Amount MAPTAC | 0% | 1.5% | 3% | 6% | 12% |
| Crosslinking ratio | 0% | 10% | 10% | 10% | 10% |
| Non-specific ads. (Lysozyme) | 55 mg | 13 mg | 13 mg | 0 mg | 0 mg |
| Passivation level | – | ± | + | + | ++ |

TABLE V

COMPOSITION OF POLYMERS AND RELATED ANALYTICAL RESULTS

| Type of silica | X 015 | X 015 | X 015 |
|---|---|---|---|
| Surface area/g | 25 m² | 25 m² | 23 m² |
| Amount MAPTAC | 0% | 1.5% | 3% |
| Crosslinking ratio | 0% | 10% | 10% |
| Non-specific ads. (Lysozyme) | 15 mg | 0 mg | 0 mg |
| Passivation level | – | + | ++ |

In both of Tables IV and V, the symbols ++, +, ±, and – have the following meanings:

++ Indicates that the number of non-specific absorptions is close to zero, indicating an excellent passivation level.

+ At a non-specific adsorption of less than 10 mg, passivation is also quite good.

± Indicates that the passivation level is less than 15 mg, which in most instances is not acceptable for use in chromatographic separation.

– Indicates that the passivation level is greater than 15 mg and thus the material is not performing the separation function correctly and thus cannot be used for chromatographic separation.

It is thus demonstrated that the level of non-specific adsorption for lysozyme (a strong cationic protein) is high when the MAPTAC is absent. The non-specific adsorption for silica with large surface are (X 075, 100 m²/g) is higher (55 mg/mL of resin) than the non-specific adsorption for silica X 015 (25 m²/g; 15 mg/mL of resin). A certain proportionality exists between the surface area and the original level of non-specific absorptions. The amount of MAPTAC to decrease the level of non-specific adsorption down to zero is also proportional to the surface area available: 1.5% of MAPTAC is necessary with silica X 015 (25 m²/g) whereas at least 6% is necessary to passivate silica X 075 (100 m²/g).

Example 15
Preparation of an Anion Exchange Resin Based on Polystyrene 10 g of methacrylamidopropyltrimethyl-ammonium chloride, 2 g of N-(1,1-dimethyl-2-phenyl)ethylacrylamide and 2 g of N,N,-methylene-bis-methacrylamide are dissolved in 30 mL of dimethyl sulfoxide. The volume of the solution is then increased to 50 mL by adding 20 mL of water. Under stirring, 0.3 g of 2,2,-azobis-(2-amidinopropane)hydrochloride is added at room temperature.

While shaking, the monomer solution is added dropwise to 50 g of porous polystyrene (50–150 μm beads diameter, 300–400 Å pore diameter). The excess of monomer solution is thus eliminated by filtration under vacuum. The impregnated polystyrene beads are introduced into a closed container and heated at 80–90° C. for five hours to polymerize the monomer solution within the pores of the polystyrene matrix.

Finally the obtained material is washed extensively with ethanol to eliminate the excess monomers and, subsequently, with water.

The resulting resin showed the following characteristics:

Very hydrophilic material (in opposition to the totally hydrophobic nature and unwettability, of the polystyrene Ion exchange capacity: 100 μeq/mL of resin Sorption capacity for BSA: 70 mg/mL.

Example 16
Performance Characteristics of the Passivated Porous Support of the Present Invention at High Flow Rates The performance characteristics of the passivated porous support are compared with those of other support materials under high solution flow rates (e.g., approaching 100 cm/hr). In particular, the relative sorption capacity and productivity characteristics of DEAE-Spherodex™, DEAE-Trisacryl Plus™, DEAE-Trisacryl™, DEAE-Agarose-based sorbent, and passivated porous supports of the present invention are illustrated in FIGS. 3A and 3B. The absolute sorption capacities at flow rates approaching 200 cm/hr are compared for these supports in FIG. 4. The data of FIG. 4 are generated for a 50 mM Tris buffer (pH 8.6) solution of BSA (5 mg/mL).

It can be seen from FIG. 3A, that the useful sorption capacity decreases by half or more at flow rates between about 50 cm/hr to about 100 cm/hr for Trisacryl, Trisacryl Plus and the Agarose-based sorbent. By contrast, the degree to which the useful sorption capacity of the passivated porous supports of the present invention (e.g., the passivated support of Example 2 or 4) is retained as flow rate increases compares favorably with DEAE-Spherodex™ even at flow rates approaching 100 cm/hr (i.e., the useful sorption capacity remains substantially unchanged as a function of flow rate).

Moreover, the productivity, a measure of the amount of material processed in the separation procedure per unit time, of the respective supports are compared in FIG. 3B. Again, the performance of the passivated porous supports of the present invention compares favorably with the DEAE-Spherodex™ sorbent. The passivated porous supports of the present invention are clearly superior to DEAE-Spherodex™, however, when their sorption capacities are compared on an absolute basis, as shown in FIG. 4.

Example 17
Preparation of an Anion-Exchange Resin Using a Surface-Protected (i.e., Pre-coated) Silica Passivated Porous Support Polystyrene pellets (10 g, average molecular weight about 400,000 Daltons) are dissolved in 100 mL of methylene chloride and then added dropwise to 100 g of porous silica (40–100 μm diameter, 2000–3000 Å pore diameter, 10 m²/g surface area and about 1 cm³/g porous volume). After about 30 minutes shaking the mixture is dried under an air stream at room temperature until total evaporation of the chlorinated solvent (i.e., until a constant weight is observed). The obtained dry powder is then heated at 190° C. overnight to permit the polystyrene to form a homogeneous thin layer on the surfaces (internal and external) of the silica.

Next, 20 g of methacrylamidopropyltrimethyl ammonium chloride (MAPTAC) and 1 g of N,N'-methylene-bismethacrylamide are dissolved in 80 mL of distilled water and the pH of the solution is adjusted to 7.5. Separately, 1 g of ammonium persulfate is dissolved in 20 mL of distilled water. The two solutions are then mixed together at room temperature and added dropwise to 100 g of polystyrene-coated silica, obtained as described above. After shaking for about 30 minutes, paraffin oil (250 mL) is added to the mixture, along with 2 mL of N,N,N',N'-tetramethylethylenediamine to polymerize the monomer solution inside the silica pores. The resulting suspension is then heated at 60–70° C. to induce polymerization.

The passivated resin is then recovered by filtration. The oil is eliminated with an extensive washing with water containing 0.1–0.5% of a non-ionic detergent and then stored in a saline buffer at neutral pH. The product resin shows very similar ion-exchange characteristics as those described in Example 2. Additionally, its sensitivity in strong alkaline media is much improved as measured by its weight loss after one night of contact with 0.5M sodium hydroxide. The passivated resin of this example lost only about half as much weight as an anionic resin prepared from silica having an unprotected surface area.

Alternatively, the polystyrene can be coated on the surfaces of the matrix by polymerizing the vinyl monomer in situ, thus assuring that the internal surfaces of even the smallest pores of the matrix are coated with protective polymer. The conditions for the polymerization of the vinyl monomer are well known to those of ordinary skill (e.g., see, *Kirk-Othmer Concise Encyclopedia of Chemical Technology*, Wiley-Interscience Publication, New York, pp. 1115–1117). After such an in situ polymerization, it is preferred that the coated support be heated overnight at 190° C., as described above, to provide a homogeneous thin-film layer over the matrix.

In addition, the polystyrene may also contain substituents, particularly at the 4-position of the phenyl ring, which can be non-ionic or ionizable. For example, carboxylic acids, carboxylic acid esters or amides, sulfates, phosphates, N,N-dialkylcarboxamides, lower alkylamines, N,N-dialkylamines, quaternary ammonium groups, and the like can be present on the polymer. Indeed, a 4-iodo substituent on all or a portion of the phenyl groups of polystyrene would allow a large host of other functional group to be introduced by known methods (e.g., formation of aryllithium, Grignard, or copper reagents followed by quenching with carbon dioxide or alkylation).

Moreover, passivation of the porous solid matrix having a thin-film coating of a synthetic organic polymer can also be achieved by other variations in the procedure disclosed in the present invention, such as the method of Example 15.

Example 18
Determination of Ion-Exchange and Protein Sorption Capacity of Preparation of Anion-Exchange Resins Based on Passivated Porous Silica Support of Different Surface Areas This example provides evidence that polymerization of the passivation mixture within porous silica matrices forms a three-dimensional polymer network or "lattice", as opposed to a thin, substantially two-dimensional surface coating. Three anion-exchange sorbents were prepared using the methods of the present invention, the differences between the sorbents relating primarily to the pore sizes and hence internal surface areas of the silica matrices. These silica substrate characteristics are summarized in the following table:

|  | X-005 | X-015 | X-075 |
| --- | --- | --- | --- |
| Particle size (microns) | 40–100 | 40–100 | 40–100 |
| Porous volume (cm³/g) | 1 | 1 | 1 |
| Pore size (Angstroms) | 3000 | 1250 | 300 |
| Surface area (m²/g) | 10 | 25 | 100 |

Surface area is seen to increase as the pore size decreases, while porous volume remains essentially constant.

The characteristics of the passivated ("Q-CPI") anion-exchange support prepared from these silica base materials are summarized in the following table:

| Silica Matrix | X-005 | X-015 | X-075 |
| --- | --- | --- | --- |
| Particle size (microns) | 40–100 | 40–100 | 40–100 |
| Ionic groups (microeq/mL) | 111 | 133 | 183 |
| BSA capacity (mg/mL) | 130 | 125 | 82 |
| Sorption efficiency | 1.17 | 0.94 | 0.45 |

The ion-exchange capacity (i.e., number of ionic groups) and BSA sorption capacity do not vary by nearly the factor that surface area varies. In particular, BSA sorption capacities decrease as the surface area of the silica increases (i.e., from left to right in the table). This is consistent with the fact that the polymeric lattice formed upon polymerization of the passivating solution forms a three-dimensional, substantially pore-filling network, as opposed to a thin pore-wall surface coating.

Example 19
Preparation of an Anion-Exchange Resin Based on a Surface-Protected (i.e., Polystyrene-Precoated) Passivated Porous Silica Support Polystyrene pellets (10 g, average molecular weight approximately 400 kD) were dissolved in 10 mL of methylene chloride and then added dropwise to 100 g of porous silica. The silica was characterized by a particle diameter of 40 to 100 microns, a pore diameter of 2000 to 3000 Angstroms, a surface area of 10 m²/g surface area, and a porous volume of about 1 cm³/g. After about 30 minutes of shaking, the mixture was dried under an air stream at room temperature until total evaporation of the chlorinated solvent had occurred, as evidenced by the attainment of a constant particle weight. The dry powder was then heated overnight at 180° C. to permit the polystyrene to form a thin, homogeneous surface layer or coating on both the internal and external exposed surface regions of the silica. This polystyrene-coated silica so obtained exhibited only a fraction of the sensitivity to alkaline media that was exhibited by unprotected silica matrices. In particular, deposition of the protective polystyrene coat in this manner was observed to reduce the extent of silica leaching by a factor of at least 2 to 3.

Next, 0.5 g of N-1-methylundecyl-acrylamide (MUA) were dissolved in 100 mL of pure ethanol, and the solution was added dropwise to 100 g of the polystyrene-coated silica obtained as described above. After shaking for about 30 minutes, the material was placed in a nitrogen stream under conditions that resulted in complete evaporation of the ethanol (again, as observed by attainment of constant solids weight).

Next, 1 g of N,N'-methylene-bis-methacrylamide was dissolved in 20 mL of dimethylsulfoxide. To this solution, 20 g of methacrylamidopropyltrimethylammonium chloride (MAPTAC) were added, and the total volume of the solution was adjusted to 80 mL by the addition of distilled water. Separately, 0.5 g of azo-bis-amidino-propane (as initiator) was dissolved in 10 mL of distilled water and then added to the solution of monomers. The volume of the latter was then adjusted to 100 mL with water; 90 mL of this solution were then added dropwise to the polystyrene-precoated silica.

This material (i.e., monomer-solution impregnated polystyrene-precoated silica) was then placed under nitrogen and in a closed vessel at 80° C. for over two hours. The product so obtained was then washed extensively with water and water-compatible solvents to remove any unpolymerized material and other reaction byproducts.

The cationic (i.e., anion-exchange) resin so prepared exhibited a fixed-charge density (i.e., ion-exchange capacity) of 150 microequivalents/mL of quaternary amino groups. Its capacity for reversibly absorbing BSA was 125 mg/mL. Non-specific binding (expected to be extensive and excessive for unpassivated, polystyrene-coated silica) was minimal for the material produced by the method of the present invention.

Example 20
Preparation of a Cationic Resin Based on a Porous Polystyrene Matrix Porous polystyrene beads, characterized by a particle diameter of 50 to 70 microns, a pore diameter of 1000 Angstroms, and a porous volume of 1.6 $cm^3/g$, were obtained as a commercially available product from Polymer Laboratories, Inc. (Amherst, Mass.). Five grams of these porous crosslinked polystyrene beads were washed extensively with ethanol and then dried under vacuum.

Separately, 61 mg of methylene-bis-methacrylamide were dissolved in 3.76 mL of dimethyl sulfoxide. To this was added 2.44 mL of an aqueous solution containing 1.3 g of methacrylamidopropyltrimethylammonium chloride (MAPTAC) and 25 mg of azo-bis-amidino-propane. To this solution, which was stirred gently under a nitrogen atmosphere at 4° C., was added 1.5 mL of pure ethanol. This solution was then added dropwise to the dry polystyrene beads until it was totally absorbed within the porous volume of the beads. After 30 minutes of shaking, the mixture was stirred in a closed vessel under a nitrogen pressure at 85° C. for at least 2 hours. After this period, the product beads were removed and washed extensively with acidic, alkaline, and aqueous alcohol solutions to remove reaction byproducts and uncopolymerized materials.

The anion-exchange resin product obtained in this manner was very hydrophilic and contained cationic groups at a density of 124 microequivalents/mL of settled resin volume. Protein sorption capacity as measured by uptake of bovine serum albumin (BSA) was between 30 and 50 mg/mL of settled resin, depending on operating conditions.

Example 21
Preparation of a Passivated Cationic Resin Based on a Porous Polystyrene Matrix Example 21 differs from the preceding Example 20 in its incorporation of the passivating monomer MUA into the mixture polymerized within the pores of the polystyrene support. As before, porous polystyrene beads, characterized by a particle diameter of 50 to 70 microns, a pore diameter of 1000 Angstroms, and a porous volume of 1.6 $cm^3/g$, are obtained as a commercially available product from Polymer Laboratories, Inc. (Amherst, Mass.). Five grams of these porous crosslinked polystyrene beads are washed extensively with ethanol and dried under vacuum.

Separately, 61 mg of methylene-bis-methacrylamide are dissolved in 3.76 mL of dimethyl sulfoxide. To this are added 2.44 mL of an aqueous solution containing 1.3 g of methacrylamidopropyltrimethylammonium chloride (MAPTAC) and 25 mg of azo-bis-amidino-propane. To this solution, which is stirred gently under a nitrogen atmosphere at 4° C. are added 1.5 mL of pure ethanol containing 50 mg of N-1-methyl-undecyl-acrylamide (MUA) as a passivating ("neutralizing")monomer. This solution is then added dropwise to the dry polystyrene beads until it is totally absorbed within the porous volume of the beads. After 30 minutes of shaking, the mixture is stirred in a closed vessel under a nitrogen pressure at 85° C. for 2 hours or more. After this period, the product beads are removed and washed extensively with acidic, alkaline, and aqueous alcohol solutions to remove reaction byproducts and uncopolymerized materials.

The anion-exchange resin product obtained in this manner contains cationic groups at a density of about 115 microequivalents/mL of settled resin volume. Protein sorption capacity as measured by uptake of bovine serum albumin (BSA) is about 80 mg/mL of settled resin. The resin is stable over a wide range of pH values (from 1 to 14) and can be used advantageously in the chromatographic separation of various protein mixtures.

Example 22
Preparation of a Passivated Anionic Resin Based on Porous Polystyrene Matrix Example 22 differs from the preceding Example 21 in two respects: (i) its replacement (on a 1-for-1 basis by weight) of an anionic monomer (acrylamidomethyl-propane sulfonic acid sodium salt) for the cationic monomer (MAPTAC) used in the passivating mixture polymerized within the pores of the porous polystyrene support, and (ii) its use of N-(1,1,3,5-tetramethyloctyl)-acrylamide as opposed to N-1-methylundecyl-acrylamide (MUA) as the passivating or neutralizing monomer.

As before, porous polystyrene beads, with a particle diameter of 50 to 70 microns, a pore diameter of 1000 Angstroms, and a porous volume of 1.6 $cm^3/g$, are obtained from Polymer Laboratories, Inc. Five grams of these porous crosslinked polystyrene beads are washed extensively with ethanol and dried under vacuum.

Separately, 61 mg of methylene-bis-methacrylamide are dissolved in 3.76 mL of dimethyl sulfoxide. To this are added 2.44 mL of an aqueous solution containing 1.3 g of acrylamido-methyl-propane sulfonic acid sodium salt and 25 mg of azo-bis-amidino-propane. To this solution, which is stirred gently under a nitrogen atmosphere at 4° C., are added 1.5 mL of pure ethanol containing 50 mg of N-(1,1,3,5-tetramethyloctyl)-acrylamide as a passivating ("neutralizing") monomer. This solution is then added dropwise to the dry polystyrene beads until it is totally absorbed within the porous volume of the beads. After 30 minutes of shaking, the mixture is stirred in a closed vessel under a nitrogen pressure at 85° C. for 2 hours or more. After this period, the product beads are removed and washed extensively with acidic, alkaline, and aqueous alcohol solutions to remove reaction byproducts and uncopolymerized materials.

The cation-exchange resin product obtained in this manner is very hydrophilic and contains anionic (sulfonate) groups at a density of about 100 microequivalents/mL of settled resin volume. Protein sorption capacity as measured by uptake of lysozyme is about 95 mg/mL of settled resin. The anionic resin is stable over a wide range of pH values (from 1 to 14) and can be used advantageously in the chromatographic separation of various protein mixtures.

Example 23
Preparation of an Anion-Exchange Resin using a Surface-Protected (i.e., Pre-coated) and POE-Passivated Porous Silica Support Polystyrene pellets (10 g, average molecular weight approximately 400 kD) were dissolved in 10 mL of methylene chloride and then added dropwise to 100 g of porous silica. The silica was characterized by a particle diameter of 40 to 100 microns, a pore diameter of 2000 to 3000 Angstroms, a surface area of 10 $m^2/g$ surface area, and a porous volume of about 1 $cm^3/g$. After about 30 minutes of shaking, the mixture was dried under an air stream at room temperature until total evaporation of the chlorinated solvent had occurred, as evidenced by attainment of a constant particle weight. The dry powder was then heated overnight at 190–200° C.

This polystyrene-coated silica was then suspended in 200 mL of an aqueous solution of 5% polyoxyethylene (POE) with an average molecular weight of about 600 kD. The mixture was stirred gently for about 5 hours at 85° C. and then the excess solution was removed by filtration. The silica beads were then washed extensively with water to remove the excess POE; the beads were finally rinsed twice with pure ethanol and dried.

Separately, 1 g of N,N'-methylene-bis-methacrylamide was dissolved in 20 mL of dimethylsulfoxide under stirring. To this solution, 20 g of methacrylamidopropyl-trimethylammonium chloride was added, and the total volume of the solution was adjusted to 80 mL by the addition of distilled water. Next, 0.5 g of azo-bis-amidino-propane was dissolved in 10 mL of water and then added to the solution of monomers. The latter was then adjusted to a total volume of 100 mL with water. Ninety milliliters of this solution were then added dropwise to the precoated POE-treated dry silica. The silica, impregnated with monomer solution, was then placed in a closed vessel at 80° C. and the polymerization was effected under nitrogen for two hours. The product so obtained was washed extensively with water and water-compatible solvents at acidic and alkaline pH values to eliminate any unpolymerized materials and reaction by products.

The cationic (i.e., anion-exchange) resin so obtained exhibited an ion-exchange capacity of 170 microequivalents/mL of quaternary ammonium groups and displayed a reversible BSA sorption capacity of 115 mg/mL. No non-specific binding was evident during a chromatographic separation conducted with the material.

Example 24
Preparation of an Anion-Exchange Resin Using a Surface-Protected (i.e., Pre-coated) and PVP-Passivated Porous Silica Support Polystyrene pellets (10 g, average molecular weight approximately 400 kD) are dissolved in 10 mL of methylene chloride and then added dropwise to 100 g of porous silica with characteristics described in the previous example. After about 30 minutes of shaking, the mixture is dried under an air stream at room temperature until total evaporation of the chlorinated solvent has occurred, as evidenced by attainment of a constant particle weight. The dry powder is then heated overnight at 190–200° C.

This polystyrene-coated silica is then suspended in 200 mL of an aqueous solution of 5% polyvinylpyrrolidone (PVP) with an average molecular weight of about 400 kD. The mixture is stirred gently for about 5 hours at 85° C. and then the excess solution is removed by filtration. The silica beads are then washed extensively with water to remove the excess POE; the beads are finally rinsed twice with pure ethanol and dried.

Separately, 1 g of N,N'-methylene-bis-methacrylamide are dissolved in 20 mL of dimethylsulfoxide under stirring. To this solution, 20 g of methacrylamidopropyl-trimethylammonium chloride are added, and the total volume of the solution is adjusted to 80 mL by the addition of distilled water. Next, 0.5 g of azo-bid-amidinopropane are dissolved in 10 mL of water and then added to the solution of monomers. The latter is then adjusted to a total volume of 100 mL with water. Ninety milliliters of this solution are then added dropwise to the precoated POE-treated dry silica. The silica, impregnated with monomer solution, is then placed in a closed vessel at 80° C. and the polymerization is effected under nitrogen for two hours. The product so obtained is washed extensively with water and water-compatible solvents at acidic and alkaline pH values to eliminate any unpolymerized materials and reaction by products.

The cationic (i.e., anion-exchange) resin so obtained exhibits an ion-exchange capacity of about 160 microequivalents/mL of quaternary ammonium groups and displays a reversible BSA sorption capacity of about 120 mg/mL. Little or no non-specific binding is evident during a chromatographic separation conducted with the material.

Example 25
Preparation of a Cation-Exchange Resin Using a Surface-Protected (i.e., Pre-coated) and POE-Passivated Porous Silica Support Polystyrene pellets (10 g, average molecular weight approximately 400 kD) are dissolved in 10 mL of methylene chloride and then added dropwise to 100 g of porous silica with the following characteristics: a particle diameter of 25 to 60 microns, a pore diameter of 3000 Angstroms, a surface area of 15 $m^2/g$ surface area, and a porous volume of about 1 $cm^3/g$. After about 30 minutes of shaking, the mixture is dried under an air stream at room temperature until total evaporation of the chlorinated solvent has occurred, as evidenced by attainment of a constant particle weight. The dry powder is then heated overnight at 190–200° C.

This polystyrene-coated silica is then suspended in 200 mL of an aqueous solution of 5% polyoxyethylene and stirred gently for about 5 hours at 85° C. The excess solution is removed by filtration. The silica beads are then washed extensively with water to remove the excess POE; the beads are finally rinsed twice with pure ethanol and dried.

Next, 1 g of N,N'-methylene-bis-methacrylamide, 1 g of methacrylamidopropyl-trimethylammonium chloride, and 18 g of acrylamido-methyl-propane sulfonic acid sodium salt are dissolved in 90 mL of a solvent mixture comprised of 20 mL of dimethylsulfoxide, 60 mL of water, and 10 mL of ethanol. To this solution 10 mL of water containing 0.5 g of azo-bis-amidinopropane are added. The final mixture so obtained is then added dropwise to the "dry", polystyrene-protected silica. This silica, impregnated with monomer solution, is then placed in a closed vessel at 80° C. and the polymerization is effected under nitrogen for a period of at least 3 hours. The polyanionic product so obtained is then washed extensively as described in the immediately preceding examples.

The resin so obtained exhibits an ion-exchange capacity of about 100 microequivalents/mL of sulfonate groups and displays a reversible lysozyme sorption capacity of about 130 mg/mL.

HyperD media

Various polyacrylamide/silica composites prepared as described hereinabove (and according to U.S. Pat. No. 5,268,097) are used as supports in accordance with the present invention in the Examples which follows. These materials are referred to hereinafter as S-HyperD F, S-HyperD M, Q-HyperD F, and Q-HyperD M. The S-HyperD media is a series of cation exchange chromatography media of various particle sizes. The Q-HyperD series is a series of anion exchange chromatography media of various particle sizes. The "F" and "M" suffixes refer to HyperD media particle sizes, with F indicating nominal media particle diameters of 35 micrometers and M indicating nominal media particle diameters of 60 micrometers.

Example 26

Determination of adsorption capacity (BSA on polyacrylamide/silica composites)

Two different polyacrylamide/silica composites were prepared as described above and are referred to hereinafter as Q-HyperD F and Q-HyperD M. The water contents of the Q-HyperD F and M media samples were determined. The particle density of hydrated Q-HyperD media was measured to be 1.424 g/cm. The particle sizes and particle size distributions were measured optically.

The static uptake capacity of Q-HyperD F and Q-HyperD M were determined from batch experiments. Known volumes of solutions of known concentration of bovine serum albumin (obtained from Sigma Chemical, St. Louis, Mo.) were prepared in well characterized buffers and added to known amounts of Q-HyperD media in sealed test tubes. These samples were allowed to equilibrate, and the supernatant was sampled to determine the amount of protein uptake. The maximum capacity (i.e., "saturation" capacity) of bovine serum albumin on both Q-HyperD F media and Q-HyperD M media in 50 mM Tris-HCl buffer at pH 8.6 was 215 mg protein per milliliter of particle.

In this manner, by varying the initial solute concentration and the relative volumes of solution and media, the equilibrium relationship between solution-phase solute concentration $C_0$ the intraparticle (sorbed) solute concentration $q_o$ can also be determined.

Example 27

Determination of adsorption capacity (ovalbumin on polyacrylamide/silica composite)

A polyacrylamide/silica composite was prepared as described above and is referred to hereinafter as Q-HyperD M. The water content of the Q-HyperD M media samples was determined. The particle density of hydrated Q-HyperD M media was calculated to be 1.424 g/cm$^3$. The particle size and particle size distribution were measured optically.

The static uptake capacity of Q-HyperD M was determined from batch experiments. Known volumes of solutions of known concentration of ovalbumin (Sigma Chemical, St. Louis, MO) were prepared in well characterized buffers and added to known amounts of Q-HyperD M media in sealed test tubes. These samples were allowed to equilibrate, and the supernatant was sampled to determine the amount of protein uptake. The capacity of ovalbumin on Q-HyperD M media in 50 mM Tris-HCl buffer at pH 8.6 was 220 mg protein per milliliter of particle.

Example 28

Determination of adsorption capacity (α-lactalbumin on polyacrylamide/silica composite)

A polyacrylamide/silica composite was prepared as described above and is referred to hereinafter as Q-HyperD M. The water content of the Q-HyperD M media samples was determined. The particle density of hydrated Q-HyperD M media was calculated to be 1.424 g/cm$^3$. The particle size and particle size distribution were measured optically.

The static uptake capacity of Q-HyperD M was determined from batch experiments. Known volumes of solutions of known concentration of α-lactalbumin (Sigma Chemical, St. Louis, Mo.) were prepared in well characterized buffers and added to a known amount of Q-HyperD M media in sealed test tubes. These samples were allowed to equilibrate, and the supernatant was sampled to determine the amount of protein uptake. The capacity of α-lactalbumin on Q-HyperD M media in 50 mM Tris-HCl buffer at pH 8.6 was 220 mg protein per milliliter of particle.

Example 29a

Determination of intraparticle diffusivity $D_s$ (high concentration in agitated contactor)

Polyacrylamide/silica composites were prepared as described above and are referred to hereinafter as Q-HyperD F and as Q-HyperD M.

An agitated contactor arranged to avoid destruction of media by grinding was filled with a known volume of a well-characterized test buffer solution of known pH. A known amount of Q-HyperD F media was suspended in the contactor, and a known volume of a known concentration of bovine serum albumin was added. The amount of protein taken up as a function of time by the Q-HyperD F media was monitored by recirculating a small stream of solution through a fast response-time spectrophotometer system. Solutions containing different initial protein concentrations were contacted with the samples of Q-HyperD F media.

In the limiting case where δ is significantly greater than 1, i.e., where $$\delta = \frac{1}{5} \frac{k_f R_p}{D_s} \frac{C_0}{q_0} \gg 1,$$

extraparticle mass transfer resistance is insignificant, and the effective diffusivity $D_s$ can be found by matching the experimentally determined solute uptake rate with the rate calculated from a least square regression of the following equation from Helfferich and Plesset (J. Chem. Phys. 28, (1958) 418.):

$$\frac{\bar{q}}{q_0} = \{1 - \exp[\pi^2(-\tau + 0.960\tau^2 - 2.92\tau^3)]\}^{1/2}.$$

where the characteristic time $\tau = D_s t/R_p^2$, the variable $D_s$ is the diffusivity of the protein in the media based on the gradient in the total intraparticle biological macromolecule concentration as the concentration driving force for diffusion, $q_0$ is the concentration of protein in the particle at equilibrium with a solution-phase solute concentration $C_0$, and $\bar{q}$ is the instantaneous concentration of protein in the particle averaged over the particle volume. This equation assumes that all of the protein in the particle is mobile, i.e. that the adsorbed or interacting macromolecule of interest is still capable of diffusing within the media.

In order to evaluate the parameter δ and confirm that the above equation is applicable in a given situation, it is first necessary to estimate the extraparticle mass transfer coefficient $k_f$. This boundary layer mass transfer coefficient $k_f$ can be obtained from well-known correlations in the literature for agitated contactors, such as that of Armenante and Kirwan, Chem. Engr. Sci., 44 (1989), 2781. Alternatively, the boundary layer mass transfer term $k_f$ can be obtained by performing an agitated contactor experiment as described above at a low initial solution-phase solute concentration $C_0$, such that δ is thereby made much smaller than unity. The solution-phase concentration $C_f$ as a function of time can then be fit in a least-squares fashion according to the following relationship:

$$\frac{C_f}{C_0} = \exp\left(-\frac{3k_f}{R_p}\frac{V_m}{V}t\right),$$

thus providing an estimate of the mass transfer coefficient. (Solute uptake curves obtained at other initial concentrations—in particular, at higher $C_0$ values—can be matched to more general expressions for solute uptake by determining the unique set of mass transfer parameters $D_s$ and $k_f$ that minimize the deviation between the actual and predicted solute uptake curves, as discussed further below.)

Figure 6A:
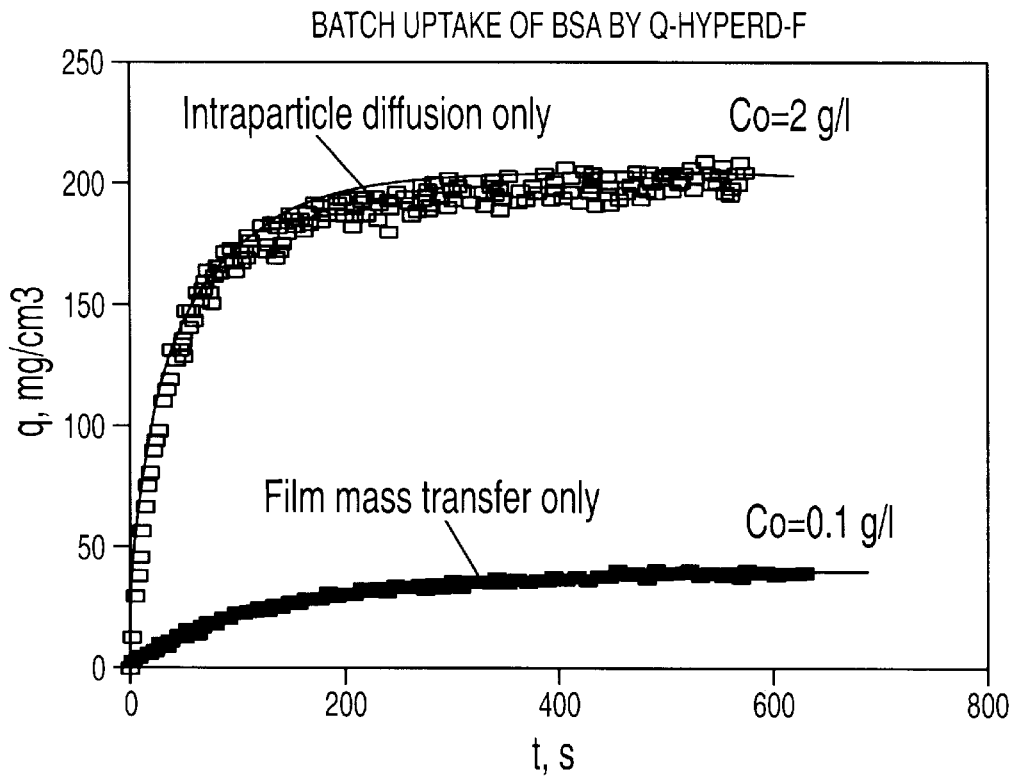
FIG. 6.A shows graphs of the BSA concentration within a medium of the present invention (Q HyperD F) as a function of time during batch uptake experiments for two initial BSA concentrations. Shown also are the results of fitting the data with analytical concentration-vs.-time solutions.
Figure 6B:
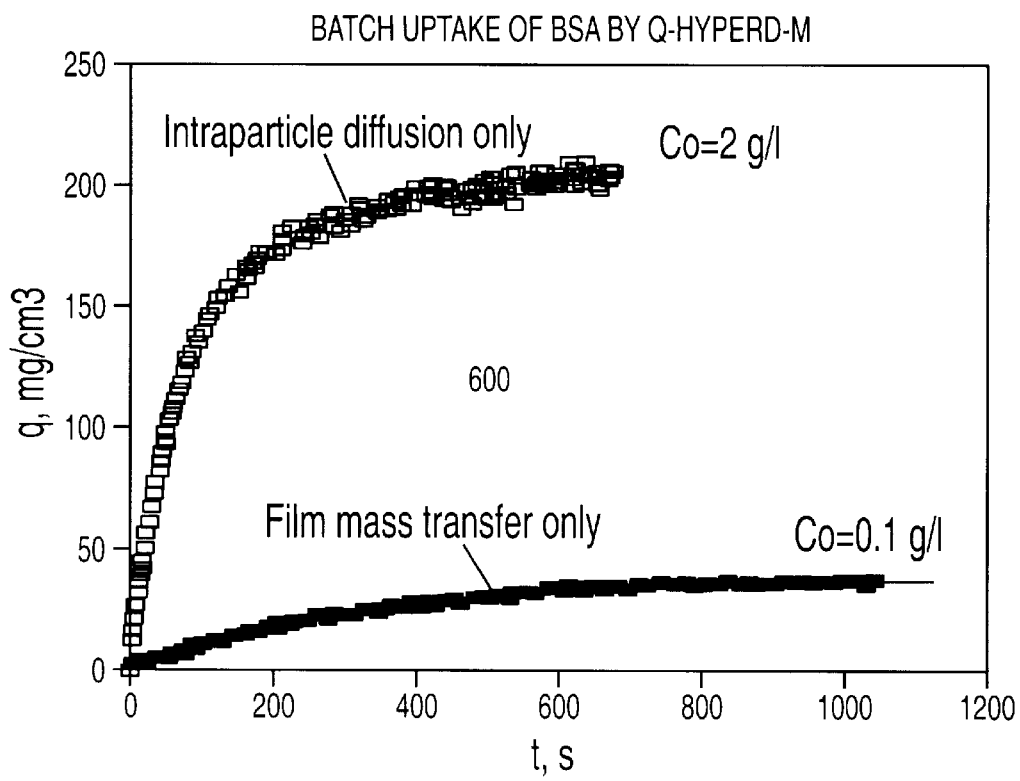

In agitated contactor experiments performed with an initial solution-phase bovine serum albumin concentration $C_0$ of 2 mg/mL, the effective diffusivity $D_s$ of BSA in Q-HyperD F was determined to be $9.2 \times 10^{-9}$ cm$^2$/s. This corresponds to an E value of 5 and an E* value of 380. Although the solute concentration of protein in the bath may decrease with time during the experiment (depending on the experimental design), using the initial solute concentration $C_0$ for the calculation of E and E* is preferred, since such a procedure results in conservative estimates of E and E* (i.e., the calculated E and E* values are smaller than they would otherwise be if calculated for some solute concentration measured later in the uptake experiment). In experiments performed using an initial bovine serum albumin concentration of $C_0$=0.1 mg/mL of solution, the mass transfer coefficient $k_f$ was determined to be $2.5 \times 10^{-3}$ cm/s. In the above example, the BSA sorption capacity for these conditions was determined to be $q_0$=215 mg/mL, and the particle radius $R_p$ was 49 μm for this HyperD F media. Thus, at an initial solute concentration $C_0$ of 2 mg/mL, the calculated δ value is 2.5—and at an initial solute concentration of 0.1 mg/mL, the calculated δ value is 0.12. These δ calculations confirm that the conditions required for calculating $D_s$ and $k_f$ according to the two equations presented are met. Shown in FIGS. 6.A is the result of fitting these analytical models for intraparticle diffusion control and film diffusion control to the experimental BSA uptake data.

Similar calculations of E and E* for HyperD media exposed to initial protein concentrations of 2 mg/mL are summarized in Table VI.

TABLE VI

| Protein | Protein conc. (mg/mL) | Media | $D_s$ | E | E* |
|---|---|---|---|---|---|
| BSA | 2.0 | Q-HyperD F | $9.2 \times 10^{-9}$ cm$^2$/s | 5 | 380 |
| BSA | 2.0 | Q-HyperD M | $9.2 \times 10^{-9}$ cm$^2$/s | 5 | 380 |
| ovalbumin | 2.0 | Q-HyperD M | $15 \times 10^{-9}$ cm$^2$/s | 8 | 260 |
| α-lactalbumin | 2.0 | Q-HyperD M | $16 \times 10^{-9}$ cm$^2$/s | 7 | 50 |

Example 29b

Determination of intraparticle diffusivity $D_s$ (agitated contactor)

Further analysis of the above experiments and additional experiments performed at other initial concentrations were carried out to more fully illustrate the particular features of the invention.

Polyacrylamide/silica composites were prepared as described above and are referred to hereinafter as Q-HyperD F and as Q-HyperD M.

An agitated contactor arranged to avoid destruction of media by grinding was filled with a known volume of a well-characterized test buffer solution of known pH. A known amount of Q-HyperD F media was suspended in the contactor, and a known volume of a BSA solution of known concentration was added. The amount of protein taken up as a function of time by the Q-HyperD F media was monitored by recirculating a small stream of solution through a fast-response-time spectrophotometer system. Solutions containing various initial protein concentrations were contacted with the samples of Q-HyperD F media in this series of experiments.

Instead of determining media characteristics (in particular, $D_s$) by the application of an analytical model of the mass transport processes involved in protein uptake, in this case we applied numerical methods to deduce the mass transfer properties of the media. This approach has the advantage that numerical solutions to the diffusion equations are more generally applicable than analytical solutions—i.e., numerical solutions are not as restricted. As pointed out above, certain limiting conditions (e.g., restrictions as to 'high' or 'low' initial solute concentration) must often be met in order for the simpler analytical solutions to be valid.

In particular, the effective diffusivity $D_s$ can be found by matching the experimental uptake rate with the rate calculated from the simultaneous numerical solution of the following equations or relationships—namely, 1) the adsorption isotherm:

$q = fn(C_0)$ i.e., the equilibrium relationship between q and $C_0$ (or, more accurately, between q and $C_i$, in instances where boundary layer mass transfer resistance is significant); 2) the numerical solution to the differential mass balance on the particle, wherein the expression for diffusive intraparticle mass transfer is based on the gradient in the total intraparticle biological macromolecule concentration as the driving force:

$$\frac{\partial q}{\partial t} = \frac{D_s}{r^2}\frac{\partial}{\partial r}\left(r^2\frac{\partial q}{\partial r}\right)$$

$$\left.\frac{\partial q}{\partial r}\right|_{r=0} = 0; \quad q = 0 @ t = 0,$$

3) the equation describing diffusion across the particle's attendant external boundary layer, as expressed in the following boundary condition:

$$\left.D_s\frac{\partial q}{\partial r}\right|_{r=R_p} = k_f(C_f - C_i)$$

and 4) the concomitant mass balance of solute in the extraparticle fluid.

The variable $D_s$ is the intraparticle diffusivity of the protein based on the gradient in total protein concentration (i.e. "bound" plus "unbound") within the particles—that is, $\partial q/\partial r$—as the driving force for diffusion, where r is the radial coordinate measured from the center of the particle. The total intraparticle biological macromolecule concentration q includes both the solute in the media that is physiochemically interacting with, or adsorbed onto, the media—as well as any "free" solute in the media that is not interacting with the polymeric gel network. The parameter $k_f$ is the extraparticle boundary layer mass transfer coefficient, which can be obtained from well-known correlations in the literature for agitated contactors, such as that of Armenante and Kirwan (Chem. Engr. Sci., 44 (1989), 2781), or from experiments wherein the parameter δ is arranged to be much less than unity. The variable $C_f$ is the solute (protein) concentration in free or bulk solution, while the variable $C_i$ is the protein concentration at the interface between the particle and the solution.

The set of coupled partial differential equations presented above are solved by discretizing the particle mass balance by orthogonal collocation in the radial direction using Jacobi polynomials (B. A. Finlayson, *Method of Weighted Residuals and Variational Principles*, Academic Press, NY 1972; J. V. Villadsen and M. L. Michelsen, *Solution of Differential Equations Models by Polynomial Approximation*. Prentice-Hall, Englewood Cliffs, N.J. 1978). This results in a system of coupled ordinary differential equations, which in turn are solved using the IMSL routine DVIPAG. (IMSL denotes the International Mathematical and Statistical Library, Visual Numerics Inc, 990 Richmond Ave, Suite 400, Houston, Tex. 77042.)

Curve matching of the numerical solution of the above equations with the experimental data provides a unique set of mass transfer parameters $D_s$ and $k_f$ consistent with the experimentally derived uptake curves (i.e. plots of $C_f$ versus time)—regardless of the initial solute concentration $C_0$. That is, the numerical solution procedure can be applied to the interpretation of data obtained over a wide range of initial solute concentrations. This is in contrast to the procedure described in the previous Example 29a, where the analytical solutions were strictly applicable only for certain initial solute concentrations (as deduced according to the parameter $\delta$).

Figure 7A:
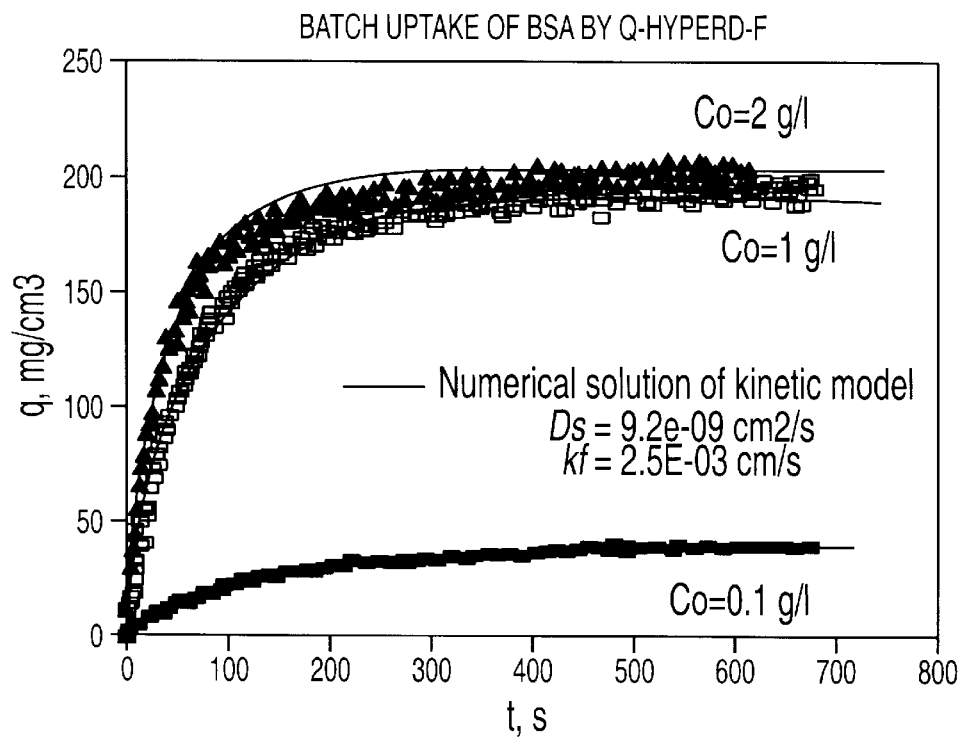
FIG. 7.A shows graphs of the BSA concentration within a medium of the present invention (Q HyperD F) as a function of time during batch uptake experiments for several initial BSA concentrations. Shown also are the results of fitting the data with a numerical concentration-vs.-time solution.
Figure 7B:
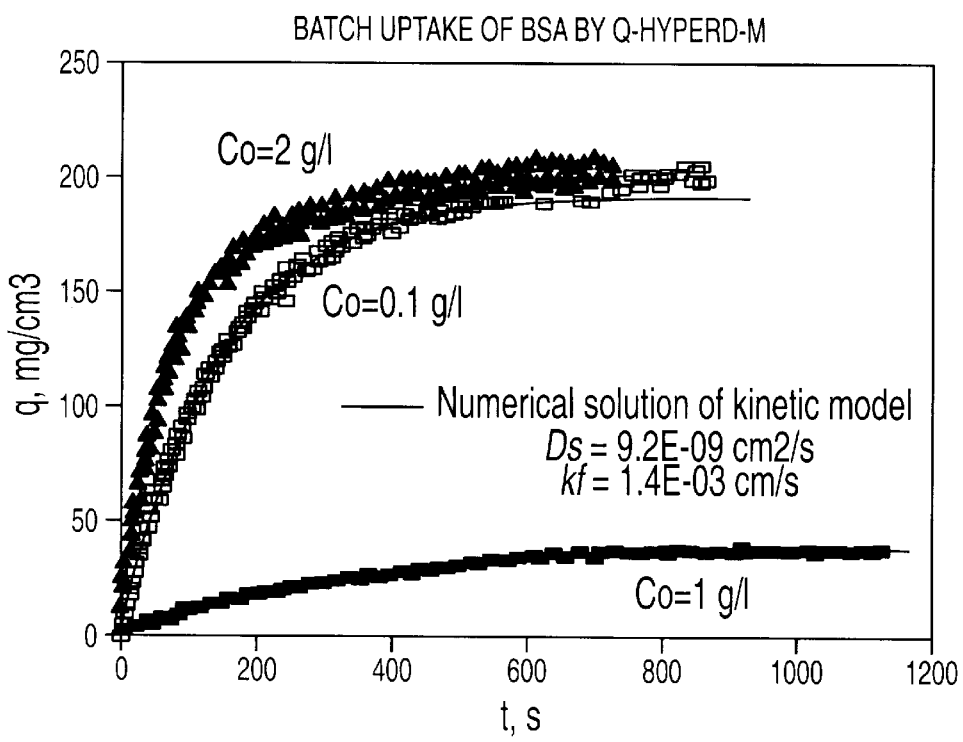

In experiments conducted with an initial bovine serum albumin concentration of 2 mg/mL of solution, the effective diffusivity $D_s$ for BSA in Q-HyperD F media was determined to be $9.2 \times 10^{-9}$ cm$^2$/s. Comparison of the experimental data with the numerical solution based on these parameters is shown in FIG. 7.A. This $D_s$ value corresponds to a calculated flux enhancement factor E of 5 and to an E* value of 380.

Table VII summarizes the E and E* calculations performed on the basis of similar experiments using various HyperD media operated at various conditions.

TABLE VII

| Protein | Protein conc'n. (mg/mL) | Media | $D_s$ | E | E* |
|---|---|---|---|---|---|
| BSA | 0.1 | Q-HyperD F | $9.2 \times 10^{-9}$ cm$^2$/s | 101 | 7600 |
| BSA | 1.0 | Q-HyperD F | $9.2 \times 10^{-9}$ cm$^2$/s | 10 | 760 |
| BSA | 2.0 | Q-HyperD F | $9.2 \times 10^{-9}$ cm$^2$/s | 5 | 380 |
| BSA | 0.1 | Q-HyperD M | $9.2 \times 10^{-9}$ cm$^2$/s | 101 | 7600 |
| BSA | 1.0 | Q-HyperD M | $9.2 \times 10^{-9}$ cm$^2$/s | 10 | 760 |
| BSA | 2.0 | Q-HyperD M | $9.2 \times 10^{-9}$ cm$^2$/s | 5 | 380 |
| ovalbumin | 0.2 | Q-HyperD M | $15 \times 10^{-9}$ cm$^2$/s | 76 | 2600 |
| ovalbumin | 0.5 | Q-HyperD M | $15 \times 10^{-9}$ cm$^2$/s | 30 | 1000 |
| ovalbumin | 2.0 | Q-HyperD M | $15 \times 10^{-9}$ cm$^2$/s | 8 | 260 |
| α-lactalbumin | 2.0 | Q-HyperD M | $16 \times 10^{-9}$ cm$^2$/s | 7 | 50 |
| α-lactalbumin | 0.5 | Q-HyperD M | $16 \times 10^{-9}$ cm$^2$/s | 28 | 180 |
| α-lactalbumin | 0.1 | Q-HyperD M | $16 \times 10^{-9}$ cm$^2$/s | 140 | 920 |

As shown in Table VII, it may be noted that the experimentally measured diffusion coefficient $D_s$ is substantially independent of solute concentration. Also as shown in Table VII, the flux enhancement factors E and E* are greater than 5 and 50, respectively, for all initial solute concentrations studied, with E and E* values increasing with decreasing initial solute concentration. As a result, the HyperD particles of the present invention provide a chromatography media that is especially useful in the capture of biological macromolecules and other solutes from dilute solutions.

Example 30

Determination of intraparticle diffusivity $D_s$ (shallow-bed assembly)

Polyacrylamide/silica composites were prepared as described above and are referred to hereinafter as Q-HyperD F and as Q-HyperD M.

A shallow-bed assembly of known dimensions was constructed by packing a small known amount of Q-HyperD F or Q-HyperD M media between two layers of inert (i.e., non-adsorbing) particles of the same size grade as the active Q-HyperD particles present in the adsorbing layer; these non-adsorbing layers provided mechanical support for the active shallow bed. This "differential" shallow-bed assembly permitted the uptake kinetics of bovine serum albumin (Sigma Chemical, St. Louis, Mo.) by Q-HyperD particles to be determined at the same hydrodynamic conditions as would exist in a much longer packed bed—without introducing complications associated with the development of solute concentration along the column length.

A solution of a known concentration of bovine serum albumin in a well-characterized buffer at known pH was then introduced to and recirculated through the column at a known flow rate. After the Q-HyperD media had been exposed to the aforesaid flowing BSA solution for varying but known amounts of time, the column was flushed briefly with a wash buffer containing no BSA. The amount of BSA sorbed in the Q-HyperD layer was then determined spectrophotometrically by eluting the BSA from the Q-HyperD media using an elution buffer solution containing 500 mM NaCl.

Figure 8:
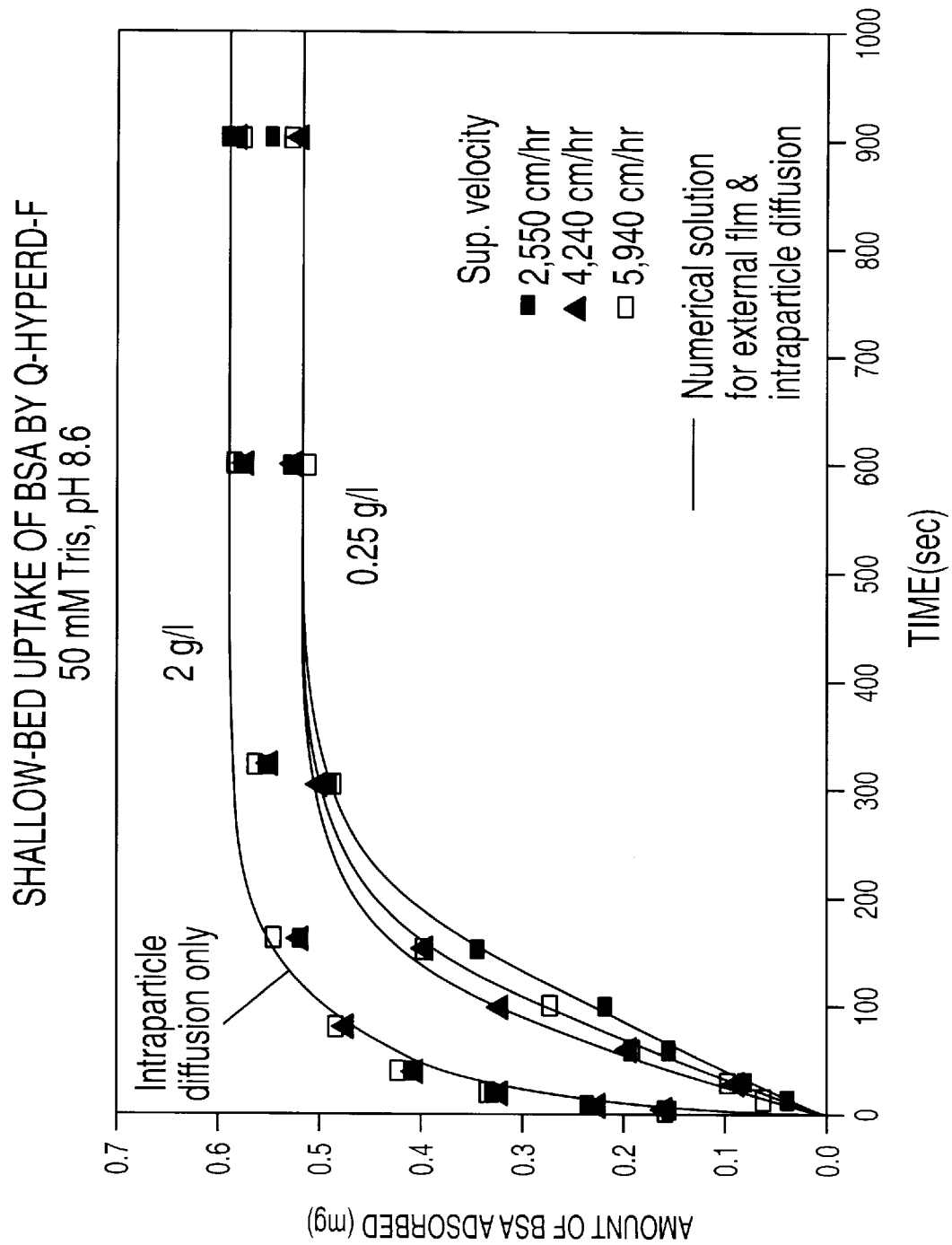
FIG. 8 shows graphs of the protein concentration within a medium of the present invention(Q HyperD F) as a function of time, with varying column velocity and BSA concentration during shallow bed experiments. Also shown are the results of using a numerical solution to describe the experimental data.
Figure 9:
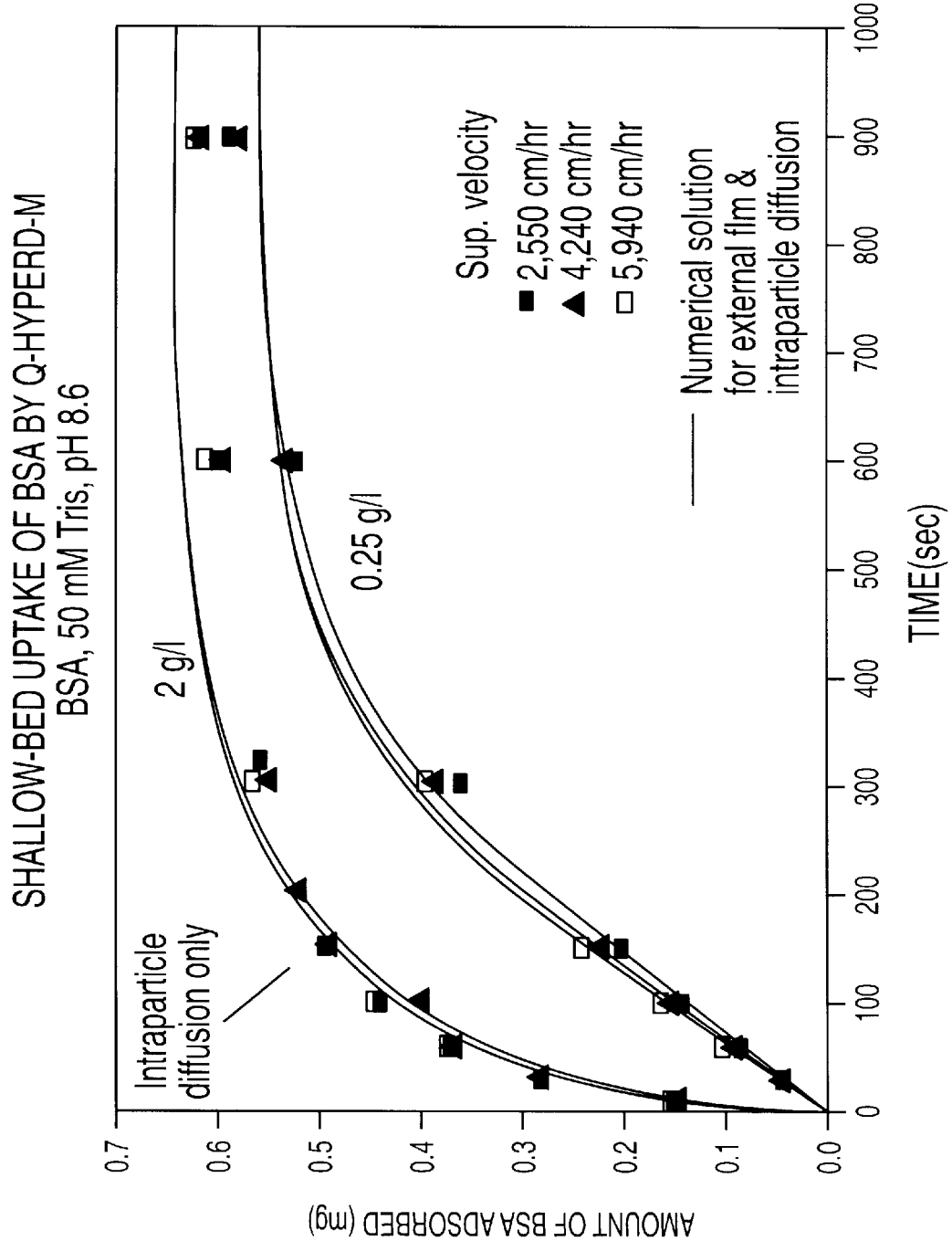
FIG. 9 shows graphs of the protein concentration within a medium of the present invention(Q HyperD M) as a function of time, with varying column velocity and BSA concentration during shallow bed experiments. Also shown are the results of using a numerical solution to describe the experimental data.

The effective diffusivity $D_s$ characteristic of the HyperD media was then found by matching the experimental uptake data to the prediction of the mathematical model of the transport process as described above. The experimental uptake curves at various initial solute concentrations can be matched to the numerical solution with minimal error for one unique set of mass transfer parameters $D_s$ and $k_f$ as shown in FIGS. 8 and 9.

In experiments conducted at a superficial column flow rate of 2550 cm/hr and with an initial solution-phase BSA concentration of 2.0 mg/mL, the effective diffusivity $D_s$ of BSA in Q-HyperD F was determined to be $9.2 \times 10^{-9}$ cm$^2$/s. This $D_s$ value corresponds to flux enhancement factors E and E* of 5 and 380, respectively.

Similar experiments and calculations performed for this and other HyperD media—as well as E and E* values obtained therefrom—are summarized in Table VIII.

It should be noted that the value of the external solute concentration $C_0$ remained essentially constant during the course of these experiments, in contrast to the situation in Examples 29a and 29b wherein the external concentration of solute decreased as the experiment progressed. There is good agreement between the E and E* values obtained in the shallow-bed experiments and the corresponding values obtained in the batch uptake experiments.

TABLE VIII

| Protein | Protein conc'n. (mg/mL) | Media | $D_s$ | E | E* |
|---|---|---|---|---|---|
| Superficial column velocity = 2550 cm/hr | | | | | |
| BSA | 0.25 | Q-HyperD F | $9.2 \times 10^{-9}$ cm²/s | 41 | 3000 |
| BSA | 2.0 | Q-HyperD M | $9.2 \times 10^{-9}$ cm²/s | 5 | 380 |
| BSA | 0.25 | Q-HyperD M | $9.2 \times 10^{-9}$ cm²/s | 41 | 3000 |
| Superficial column velocity = 5940 cm/hr | | | | | |
| BSA | 2.0 | Q-HyperD F | $9.2 \times 10^{-9}$ cm²/s | 5 | 380 |
| BSA | 0.25 | Q-HyperD F | $9.2 \times 10^{-9}$ cm²/s | 41 | 3000 |
| BSA | 2.0 | Q-HyperD M | $9.2 \times 10^{-9}$ cm²/s | 5 | 380 |
| BSA | 0.25 | Q-HyperD M | $9.2 \times 10^{-9}$ cm²/s | 41 | 3000 |

Table VIII further shows that the intraparticle diffusivity is independent of the flow rate outside the particle. Furthermore, comparison of the results in Table VIII for the shallow-bed experiments with those summarized in Table VII for the batch uptake experiments indicates that the same intraparticle diffusivity is determined by both experimental methods and for both F-grade and M-grade HyperD media.

Example 32a
Determination of column or bed void volume $\epsilon_b$

The void volume of the column $\epsilon_b$ expressed as a fraction of the total column volume was calculated from (i) the weight of a water-saturated packed bed of HyperD particles ($M_c$) and (ii) the total column volume ($V_c$). With this information, as well as the apparent density of the hydrated media ($\rho_p$) and the density of the aqueous buffer (approximately equal to the density of water, $\rho_{water}$), the column void volume $\epsilon_b$ was calculated using the following equation:

$$\varepsilon_b = \frac{\rho_p - M_c / V_c}{\rho_p - \rho_{water}}$$

$\rho_p$ is found from the volumetric average of the water density $\rho_{water}$ and the skeletal density $\rho_{skeleton}$ as shown below:

$$\rho_p = \epsilon_p \rho_{water} + (1 - \epsilon_p) \rho_{skeleton}$$

Mercury intrusion experiments give a value of 0.65 for the porosity $\epsilon_p$ of the silica support used in the manufacture of the HyperD media. The density of the silica skeleton is reported as 2.21 g/cm³. This results in a calculated value for $\rho_p$ of 1.424 g/cm³.

Substitution of these and other parameters in the above expression yields bed void volumes $\epsilon_b$ of 0.5, 0.48, 0.49, and 0.5 for four columns packed with the HyperD composite media of the present invention.

Example 32b
Determination of species-dependent intraparticle void volume fraction $\epsilon_p^*$ A polyacrylamide/silica composite was prepared as described above and is referred to hereinafter as Q-HyperD F.

A chromatographic column of known volume was packed with a known and salt-invariant volume of Q-HyperD F media. The column was attached to a chromatographic pumping system with known dead volumes. The column was equilibrated with a well characterized buffer, and a pulse of solute or protein was injected into the column, followed by buffer. The flow rate of the buffer was chosen to minimize the effects of axial dispersion. The ionic strength of the buffer system was chosen to eliminate any ionic interactions between the solute and the HyperD media. The elution volume of the solute pulse $V_e$ is defined as the first moment of the elution peak. The volume of the particle accessible to the solute is obtained by subtracting from the elution volume both the dead volume of the extra column equipment, $V_{deadvolume}$, and the interstitial volume of the column, $\epsilon_b V_c$. The species dependent void volume fraction $\epsilon_p^*$ is obtained by dividing the species-dependent void volume by the total volume of particles in the bed. Thus, $\epsilon_p^*$ is given by the following expression:

$$\varepsilon_p^* = \frac{V_e - V_{deadvolume} - \varepsilon_b V_c}{(1 - \varepsilon_b) V_c}$$

The void volume of the bed $\epsilon_b$ of Q-HyperD F packed in the aforesaid column was obtained by (i) determining the weight of the water-saturated packed bed in the column and the total column volume and (ii) performing the calculations set forth in Example 32a above.

Using these techniques, the following species-dependent void volumes fractions $\epsilon_p^*$ were obtained.

TABLE IX

| Protein | Buffer | Media/NaCl (millimolar) | pH/buffer (millimolar) | $\epsilon_p^*$ |
|---|---|---|---|---|
| cytochrome-C | sodium phosphate | S-HyperD F/(1000) | 6.5/(10) | 0.095 |
| cytochrome-C | sodium phosphate | S-HyperD M/(1000) | 6.5/(10) | 0.15 |
| BSA | Tris-HCl | Q-HyperD F/(1000) | 8.5/(50) | <0.01 |
| BSA | Tris-HCl | Q-HyperD M/(1000) | 8.5/(50) | <0.01 |
| Dextran T-40 | Tris-HCl | Q-HyperD F/(175) | 8.5/(50) | 0.01 |
| Dextran T-40 | Tris-HCl | Q-HyperD M/(185) | 8.5/(50) | <0.01 |
| Dextran T-40 | sodium phosphate | S-HyperD F/(150) | 6.5/(10) | <0.01 |
| Dextran T-40 | sodium phosphate | S-HyperD M/(150) | 6.5/(10) | <0.01 |
| blue dextran | sodium phosphate | S-HyperD F/(150) | 6.5/(10) | <0.01 |
| blue dextran | sodium phosphate | S-HyperD M/(150) | 6.5/(10) | <0.01 |

From the agreement between $\epsilon_p^*$ values for Dextran T-40 and BSA, it can be seen that $\epsilon_p^*$ is independent of salt concentration between salt concentrations up to at least 1000 millimolar salt. It can also be seen from $\epsilon_p^*$ values for blue dextran (a very large solute, having a molecular weight of approximately 2,000,000) and BSA that molecules as large or larger than BSA have $\epsilon_p^*$ values less than about 0.01. The fact that these $\epsilon_p^*$ values are generally much smaller than unity illustrates that, under nonbinding/noninteractive conditions, the degree of steric exclusion of solute by the supported polymeric gel network of the present invention is indeed appreciable. Given this steric effect, it is thus particularly unexpected that the rates of intraparticle diffusive mass transfer can be as large as observed—as exemplified by the large values of the flux enhancement factor E* calculated for composite media of the present invention.

Example 33
Prediction of species-dependent void volume fraction $\epsilon_p^*$

The species-dependent void volume of the media in the present invention can be adequately predicted by applying the Ogston equation to describe exclusion by the polymer network of the composite media—modifying the Ogston equation to take into account the volume taken up by the skeleton or porous support particle that forms the base matrix for the composite media of this invention. The Ogston equation so modified is shown below:

$$\frac{\varepsilon_p^*}{\varepsilon_p} = \exp\left[-\phi\left(1 + \frac{a}{a_f}\right)^2\right]$$

where a is the Stokes radius of the biological molecule of interest, $a_f$ is the effective radius of a strand of polymer forming the gel network, and $\phi$ is the volume fraction of the polymer forming the network. For the HyperD embodiment of present invention based on a silica-supported polyacrylamide gel, the polymer volume fraction $\phi$ is equal to 0.105, and the effective radius of a strand of polyacrylamide is 6.5 Å. The Stokes radius for globular proteins can be obtained from the correlation $$a_f = 0.875(MW)^{1/3}$$

where MW is the molecular weight of the globular protein of interest (Tyn and Guseck, *Biotech. Bioeng.*,

| Molecular Weight | $\epsilon_p^*$ |
|---|---|
| 10,000 | 0.132 |
| 13,000 | 0.105 |
| 15,000 | 0.092 |
| 20,000 | 0.067 |
| 30,000 | 0.039 |
| 40,000 | 0.024 |
| 45,000 | 0.019 |
| 50,000 | 0.016 |
| 55,000 | 0.013 |
| 60,000 | 0.010 |
| 65,000 | 0.009 |
| 80,000 | 0.005 |
| 100,000 | 0.003 |
| 150,000 | 0.001 |
| 200,000 | 0.000 |

35, pp. 327–338 (1990)). This equation gives values for $\epsilon_p^*$ shown in the following table:

The protein BSA, which has a molecular weight of 65,000 Daltons, is thus predicted to exhibit an $\epsilon_p^*$ value of 0.009, which is in good agreement with the experimentally determined values in Table IX. Cytochrome C, which has a molecular weight of about 13,000, is predicted to exhibit an $\epsilon_p^*$ value of 0.105—again, in good agreement with the measured values in Table IX.

Example 34

Estimation of E and E* values for prior-art media

As described above, the experimentally determined diffusion coefficient $D_s$ is the proportionality constant between the gradient in the total intraparticle solute concentration and the intraparticle solute flux. However, another diffusion coefficient (defined somewhat differently) has often been reported in the literature, which for the purposes of this discussion will be referred to as the effective diffusivity $D_e$. The experimentally determined diffusion coefficient $D_e$ is the proportionality constant between the gradient in the unbound or nonadsorbed intraparticle solute concentration and the intraparticle solute flux. That is, the difference between the two intraparticle diffusion coefficients $D_s$ and $D_e$ lies in the different concentration driving force definitions upon which they are based.

The calculation of flux enhancement factors E and E* from reports in the published literature on prior-art media can be performed precisely as described in the preceding examples in instances where the literature references provide the original or unreduced adsorption data (e.g., on solute uptake as a function of time in batch uptake experiments). By the same token, E and E* may be evaluated from the published literature on prior-art media in instances where the rate-of-adsorption data has been properly reduced and then reported in terms of a effective diffusivity $D_s$ that has been derived in a manner consistent with the way in which this coefficient has been defined above. However, in still other instances, the published literature will not provide unreduced data, nor will it report an effective diffusivity consistent with the definition of $D_s$ used herein.

In such cases, it may be possible to estimate E and E* from published reports on prior-art media by "converting" the reduced data to a more suitable form or by using it in an appropriate (i.e., equivalent) manner. In particular, in comparing the present invention with prior-art media, it is useful to be able to calculate E and E* from values of the effective diffusivity $D_e$ published for prior-art media. Moreover, it is also useful to be able to calculate E and E* values from data—whether reduced or not—obtained in other types of chromatographic experiments (e.g., from analysis of column breakthrough behavior).

The effective diffusivity $D_e$ is commonly obtained as a result of analyzing data on solute (protein) adsorption in terms of the well-known "shrinking core" model of the kinetics of solute uptake. Although the calculations of the type described herein may be conducted for more complicated situations, the discussion here will be limited to the case where the adsorption isotherm is "rectangular" (i.e., the adsorption equilibrium is highly favorable) for the sake of simplicity of exposition. We also specify that extraparticle boundary layer mass transfer resistance is insignificant, i.e., that $\delta$ is significantly greater than 1, where $$\delta = \frac{1}{5}\frac{k_f R_p}{D_s}\frac{C_0}{q_0}$$

Under these conditions, the shrinking core model of protein adsorption kinetics is described by the following equations:

$$\frac{6D_e C_0}{R_p^2 q_0}t = \frac{1}{\Lambda a}\left\{2\sqrt{3}\left[\tan^{-1}\frac{2-a}{a\sqrt{3}} - \tan^{-1}\frac{2\xi-a}{a\sqrt{3}}\right] + \ln\left[\frac{(\xi+a)^2(1-a+a^2)}{(1+a)^2(\xi^2-\xi a+a^2)}\right] + 2a\ln\left[\frac{\xi^3+a^3}{1+a^3}\right]\right\}$$

where $\xi = \left(1-\frac{\bar{q}}{q_0}\right)^{1/3}$, $\Lambda = \frac{V_m q_0}{V C_0}$, and $a = \left(\frac{1-\Lambda}{\Lambda}\right)^{1/3}$ and where V is the solution volume, $V_m$ is the media volume, $C_o$ is the initial solute concentration, and $q_o$ is the equilibrium or "saturation" capacity of the media.

In contrast, a preferred model for the kinetics of adsorption in HyperD and other media that are within the scope of the present invention treats the media as a pseudo-homogeneous particle. It is this model, variously referred to by different investigators as a "homogeneous diffusion" or "solid diffusion" model, that was developed and discussed in the preceding examples in the context of describing the mass transfer performance of HyperD media and in calculating E and E* values for these sorbents. In the case where extra-particle boundary layer resistance is small and where the sorption isotherm is rectangular, the uptake of protein from an infinite reservoir into the sorbent may be described by the following equation:

$$\frac{\bar{q}}{q_0} = 1 - \frac{6}{\pi} \sum_{k=1}^{\infty} \frac{1}{k} \exp\left[-\frac{k^2 \pi^2 D_s t}{R_p^2}\right]$$

$$\approx \{1 - \exp[\pi^2(-\tau + 0.960\tau^2 - 2.92\tau^3)]\}^{1/2}$$

where $\tau = D_s t / R_p^2$.

Equating the predictions of these two models at the condition of 50% solute uptake (i.e., $\bar{q}/q_o = 0.5$) results in the following relationship between $D_e$ and $D_s$: $0.6117 D_s q_0 = D_e C_0$ Solution of this equation for $D_s$—and then substitution into the defining equations for E and E* as given above—ultimately yields the following expressions for the flux enhancement factors E and E* in terms of the reduced effective diffusivity $D_e$:

$$E = \frac{D_e}{0.6117 \frac{D_f \varepsilon_p}{\tau}} \quad \text{and} \quad E^* = \frac{D_e}{0.6117 \frac{D_f \varepsilon_p^*}{\tau}}.$$

These $D_e$-based expressions for the flux enhancement factors can be expected to yield E and E* values that represent overestimates of the values that would be derived from analysis of the raw or unreduced data; that is, E and E* values for prior-art media that are derived from reported $D_e$ values will tend to be larger than those calculated by the preferred methods using unreduced data or $D_s$ values as taught herein.

Tables X.A and X.B summarize flux enhancement factors E and E* for a number of prior-art media. In each instance, these tables show the particular type of diffusion coefficient—that is, $D_e$ or $D_s$—upon which the calculations of E and E* were based. A complete summary of the parameters entering into these calculations is provided in Table XI.

TABLE X

| PROTEIN/MEDIUM | METHOD | REFERENCE | TYPE OF DATA | E |
|---|---|---|---|---|
| Ova/Sephacel | Breakthrough | [1]Shiosaki | $D_e$ | 9 |
| Myo/Sephacel | Breakthrough | [1]Shiosaki | $D_e$ | 8 |
| BSA/Sephadex A-50 | Uptake | [2]Tsou | $D_s$ | 7 |

TABLE X-continued

| BSA/Sephadex A-50 | Breakthrough | [3]Pinto | $D_e$ | 2 |
| BSA/Chitosan | Uptake | [4]Yoshida | $D_e$ | 2 |
| BSA/Q-Spherosil | Uptake | [5]vanderWiel | $D_e$ | 0.1 |
| BSA/Q-Spherosil | Breakthrough | [6]Schanen | $D_s$ | 0.3 |
| Hb/Q-Spherosil | Breakthrough | [6]Schanen | $D_s$ | 0.2 |
| BSA/Cellulose | Uptake | [7]Graham | $D_s$ | <0.1 |

| PROTEIN/MEDIUM | METHOD | REFERENCE | Data Source | E* |
|---|---|---|---|---|
| Ova/Sephacel | Breakthrough | [1]Shiosaki | $D_e$ | 35 |
| Myo/Sephacel | Breakthrough | [1]Shiosaki | $D_e$ | 33 |
| BSA/Sephadex A-50 | Uptake | [2]Tsou | $D_s$ | 208 |
| BSA/Sephadex A-50 | Breakthrough | [3]Pinto | $D_e$ | 67 |
| BSA/Chitosan | Uptake | [4]Yoshida | $D_e$ | 2 |
| BSA/Q-Spherosil | Uptake | [5]vanderWiel | $D_e$ | 0.1 |
| BSA/Q-Spherosil | Breakthrough | [6]Schanen | $D_s$ | 0.3 |
| Hb/Q-Spherosil | Breakthrough | [6]Schanen | $D_s$ | 0.2 |
| BSA/Cellulose | Uptake | [7]Graham | $D_s$ | <0.1 |

[1]A. Shiosaki, M. Goto, T. Hirose, J. Chromatography, 679, p1–9, 1994.
[2]H. S. Tsou, E. E. Graham, AIChE J. 35, p1959, 1985.
[3]N. G. Pinto, E. E. Graham, Reactive Polymers, 5, p49–53, 1987.
[4]H. Yoshida, M. Yoshikawa, T. Kataoka, AIChE J. 40, p2034–2944, 1994.
[5]J. P. van der Weil, Ph. D. Thesis, Academish Boekin, Centrum Delft, Nederlands, 1989.
[6]V. Schanen, K. T. Chue, G. Grevillot, Proceedings of the 9th International Symposium on Preparative and Industrial Chromatography, Chair: M. Perrut, Societe Francaise de CHimie, 1992.
[7]E. E. Graham, C. F. Fook, AIChE J., 28, p245, 1982.

TABLE X.B

| PROTEIN/MEDIUM | METHOD | REFERENCE | Data Source | E* |
|---|---|---|---|---|
| Ova/Sephacel | Breakthrough | [1]Shiosaki | $D_e$ | 35 |
| Myo/Sephacel | Breakthrough | [1]Shiosaki | $D_e$ | 33 |
| BSA/Sephadex A-50 | Uptake | [2]Tsou | $D_s$ | 208 |
| BSA/Sephadex A-50 | Breakthrough | [3]Pinto | $D_e$ | 67 |
| BSA/Chitosan | Uptake | [4]Yoshida | $D_e$ | 2 |
| BSA/Q-Spherosil | Uptake | [5]vanderWiel | $D_e$ | 0.1 |
| BSA/Q-Spherosil | Breakthrough | [6]Schanen | $D_s$ | 0.3 |
| Hb/Q-Spherosil | Breakthrough | [6]Schanen | $D_s$ | 0.2 |
| BSA/Cellulose | Uptake | [7]Graham | $D_s$ | <0.1 |

[1]A. Shiosaki, M. Goto, T. Hirose, J. Chromatography, 679, p1–9, 1994.
[2]H. S. Tsou, E. E. Graham, AIChE J. 35, p1959, 1985.
[3]N. G. Pinto, E. E. Graham, Reactive Polymers, 5, p49–53, 1987.
[4]H. Yoshida, M. Yoshikawa, T. Kataoka, AIChE J. 40, p2034–2944, 1994.

TABLE XI

| $D_f$ | $D_e$ | $C_o$ | $Q_o$ | $q_o/C_o$ | $D_s$ | $\epsilon_p$ | $\epsilon_p^*$ | $\tau$ | E | E* | Protein/Resin | Reference |
|---|---|---|---|---|---|---|---|---|---|---|---|---|
| 6.7E-07 | 2.9E-06 | N/A | N/A | N/A | N/A | 0.80 | 0.20 | 2 | 9 | 35 | Ova/Sephacel | 1 |
| 1.1E-06 | 4.5E-06 | N/A | N/A | N/A | N/A | 0.80 | 0.20 | 2 | 8 | 33 | Myo/Sephacel | 1 |
| 6.0E-07 | N/A | N/A | N/A | 150 | 2.5E-08 | 0.90 | 0.03 | 2 | 7 | 208 | BSA/Sephadex A-50 | 2 |
| 6.0E-07 | 7.3E-07 | N/A | N/A | N/A | N/A | 0.90 | 0.03 | 2 | 2 | 67 | BSA/Sephadex A-50 | 3 |
| 6.0E-07 | 8.0E-07 | N/A | N/A | N/A | N/A | 0.89 | 0.89 | 2 | 2 | 2 | BSA/Chitosan | 4 |
| 6.0E-07 | 3.0E-08 | N/A | N/A | N/A | N/A | 0.65 | 0.65 | 2 | 0.1 | 0.1 | BSA/Q-Spherosil | 5 |
| 6.0E-07 | N/A | N/A | N/A | 9 | 6.0E-09 | 0.65 | 0.65 | 2 | 0.3 | 0.3 | BSA/Q-Spherosil | 6 |
| 6.9E-07 | N/A | N/A | N/A | 10 | 4.0E-09 | 0.65 | 0.65 | 2 | 0.2 | 0.2 | Hb/Q-Spherosil | 6 |
| 6.0E-07 | N/A | 80 | 1.86 | 0 | 9.0E-09 | 0.72 | 0.35 | 2 | <0.1 | <0.1 | BSA/Cellulose | 7 |

[1] A. Shiosaki, M. Goto, T. Hirose, J. Chromatography, 679, p 1–9, 1994.
[2] H. S. Tsou, E. E. Graham, AIChE J. 35, p 1959, 1985.
[3] N. G. Pinto, E. E. Graham, Reactive Polymers, 5, p 49–53, 1987.
[4] H. Yoshida, M. Yoshikawa, T. Kataoka, AIChE J. 40, p 2034–2944, 1994.
[5] J. P. van der Weil, Ph. D. Thesis, Academish Boekin, Centrum Delft, Nederlands, 1989.
[6] V. Schanen, K. T. Chue, G. Grevillot, Proceedings of the 9th International Symposium on Preparative and Industrial Chromatography, Chair: M. Perrut, Societe Francaise de Chimie, 1992.
[7] E. E. Graham, C. F. Fook, AIChE J., 28, p 245, 1982.

It should be noted that the parameters $C_o$ and $q_o$ are not required in the De-based calculations of E and E*—hence, the "N/A" or "not applicable" entries in Table XI above. It may further be noted that some of the prior-art references that reported $D_s$ values did not report $C_o$ and $q_o$ values; instead, these references either reported parameters descriptive of the adsorption isotherm or published the isotherm itself in the form of a graphical plot. In these instances, the maximum (i.e., highest) value of the ratio of $q_o/C_o$ was determined and used in the calculation of E and E*, thereby resulting in estimates of the flux enhancement factors for these prior-art media that are correspondingly high.

Example 35
Increase in dynamic capacity with decreasing applied BSA concentration A column of Q HyperD F (approximately 50 μm particle size) was prepared with dimensions of 3.45 cm by 0.5 cm. The protein BSA was prepared at two concentrations (1 mg/mL and 10 mg/mL) in 50 mM Tris buffer adjusted to pH 8.5. The column was loaded with these BSA solutions at varying column velocities, and the amount of BSA retained in the column at 10% breakthrough was determined. The dynamic capacity was calculated from the amount of BSA retained in the column and the volume of the media. For a velocity of 1528 cm/hr, the 10 mg/mL BSA experiments resulted in a measured dynamic capacity of 65 mg/mL— while at the same velocity of 1528 cm/hr, the 1 mg/mL BSA experiments resulted in a measured dynamic capacity of 86 mg/mL, representing a significant increase over that measured with the 10 mg/mL feed solution.

Figure 10:
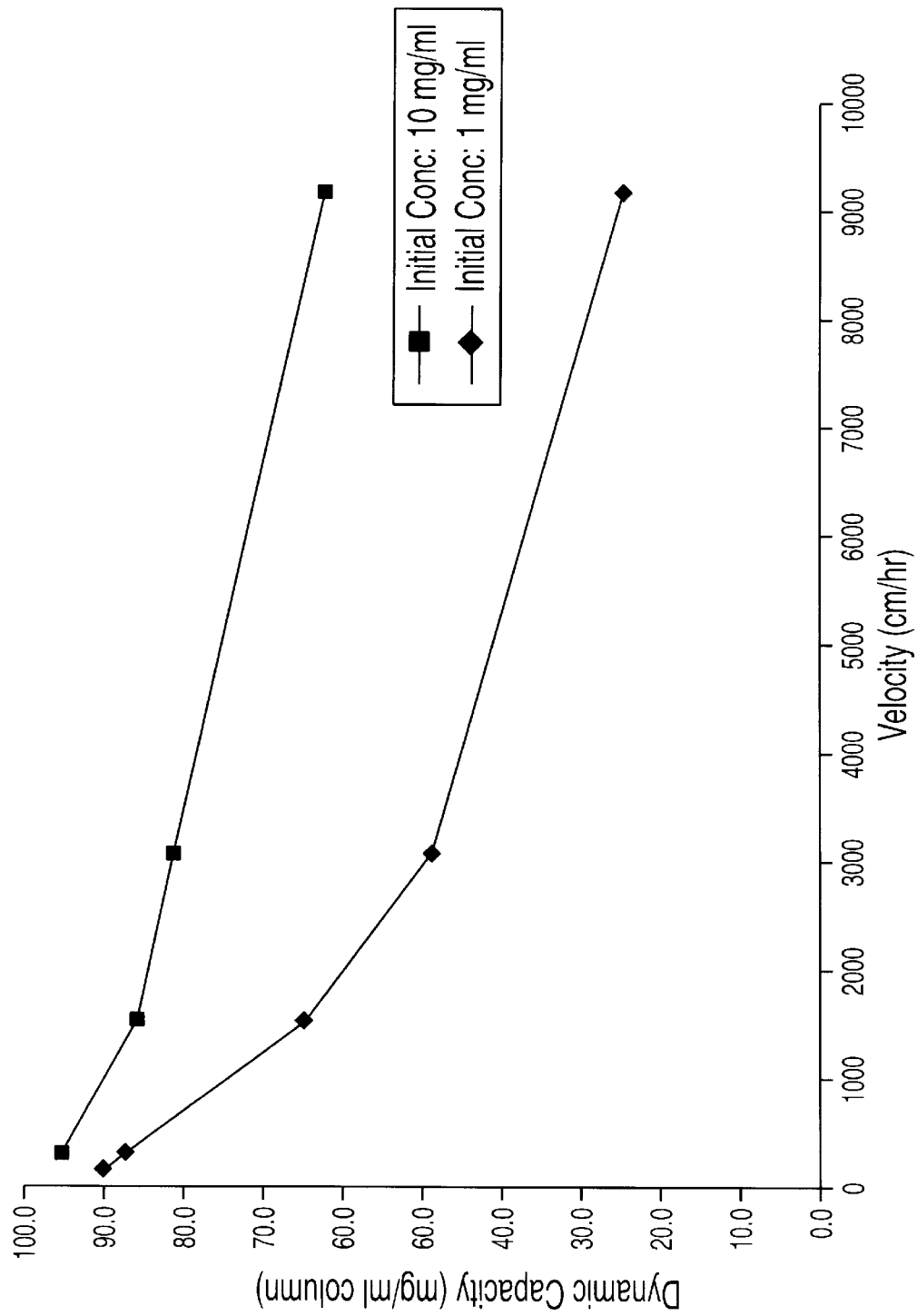
FIG. 10 shows graphs of the dynamic capacity of BSA on a medium of the present invention (Q HyperD F) having a 50 μm particle size, plotted as a function of velocity at two different solute concentrations.

Further testing was done at additional column velocities; FIG. 10 shows dynamic capacity measurements made as function of BSA concentration.

Example 36
Increase in dynamic capacity with decreasing applied IgG concentration A column of S HyperD M (approximately 75 μm particle size) was prepared with dimensions of 15 cm by 0.2 cm. The protein IgG was prepared at two concentrations (1 mg/mL and 10 mg/mL) in a 50 mM acetate buffer adjusted to pH 4.5. The column was loaded with the IgG solutions at varying column velocities, and the amount of IgG retained in the column at 10% breakthrough was determined. The dynamic capacity was calculated from the amount of IgG retained in the column and the volume of the media. In experiments conducted at a bed velocity of 1000 cm/hr with the 10 mg/mL IgG feed solution, the media exhibited a dynamic capacity of 37 mg/mL, while operation at the same velocity of 1000 cm/hr but with the 1 mg/mL IgG feed solution produced a measured dynamic capacity of 60 mg/mL, a significant increase over that measured for the 10 mg/mL feed solution.

Figure 11:
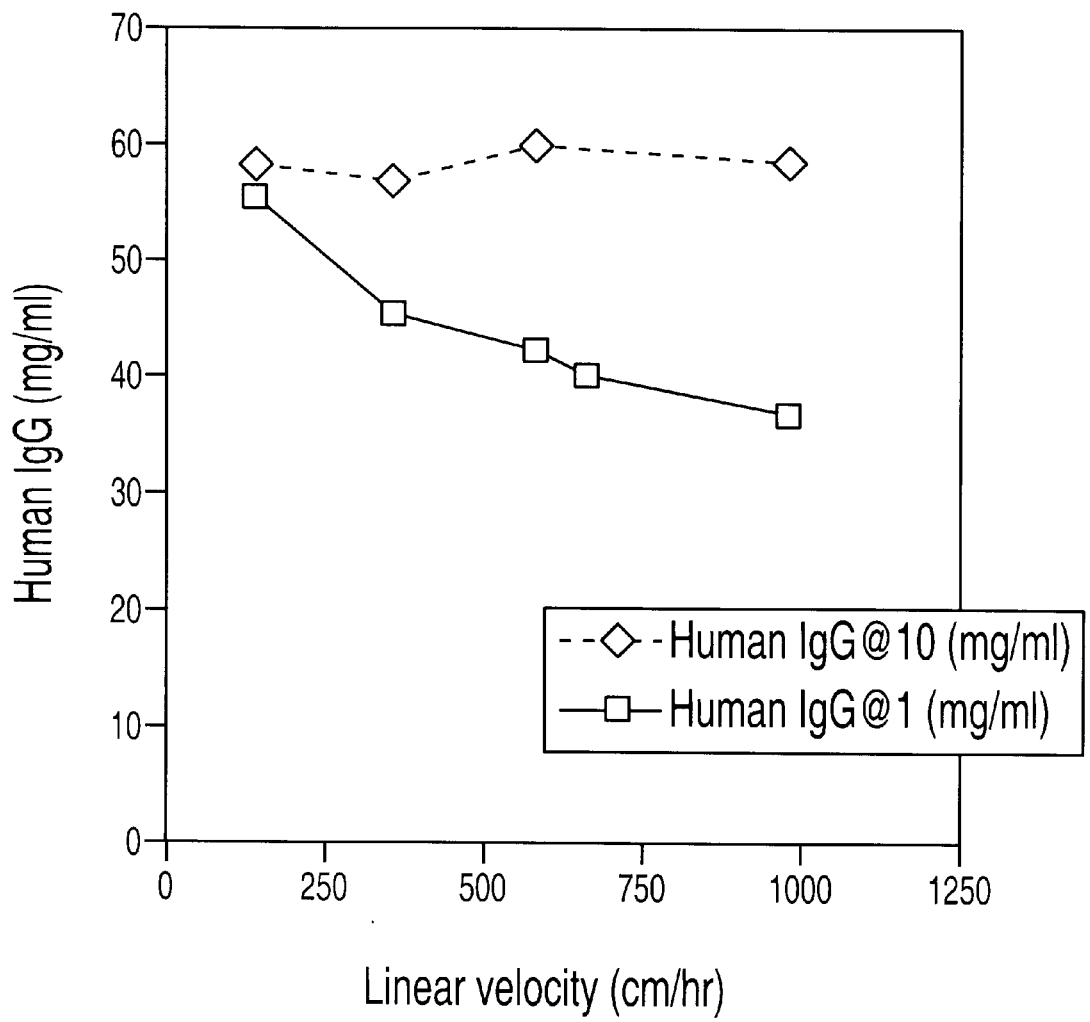
FIG. 11 shows graphs of the dynamic capacity of human IgG on a medium of the present invention (S HyperD M) having a 75 μm particle size, plotted as a function of velocity at two different solute concentrations.

Further testing at other bed velocities produced the dynamic IgG capacity results summarized FIG. 11.

Example 37
Increase in dynamic capacity with decreasing applied lysozyme concentration A column of S HyperD M (approximately 75 μm particle size) was prepared with dimensions of 15 cm by 0.2 cm. The protein lysozyme was prepared at two concentrations (0.25 mg/mL and 10 mg/mL) in a 50 mM acetate buffer adjusted to pH 4.5. The column was loaded with these lysozyme solutions at varying bed velocities, and the amount of lysozyme retained in the column at 10% breakthrough was determined. The dynamic capacity was calculated from the amount of lysozyme retained in the column and the volume of the media. In experiments conducted at a bed velocity of about 1000 cm/hr with the 10 mg/mL lysozyme feed solution, a dynamic capacity of 68 mg/mL was measured, while operation at the same velocity of about 1000 cm/hr with the more dilute (0.25 mg/mL) lysozyme feed solution produced a measured dynamic capacity of 118 mg/mL, a significant increase over that measured for the more dilute solution.

Figure 12:
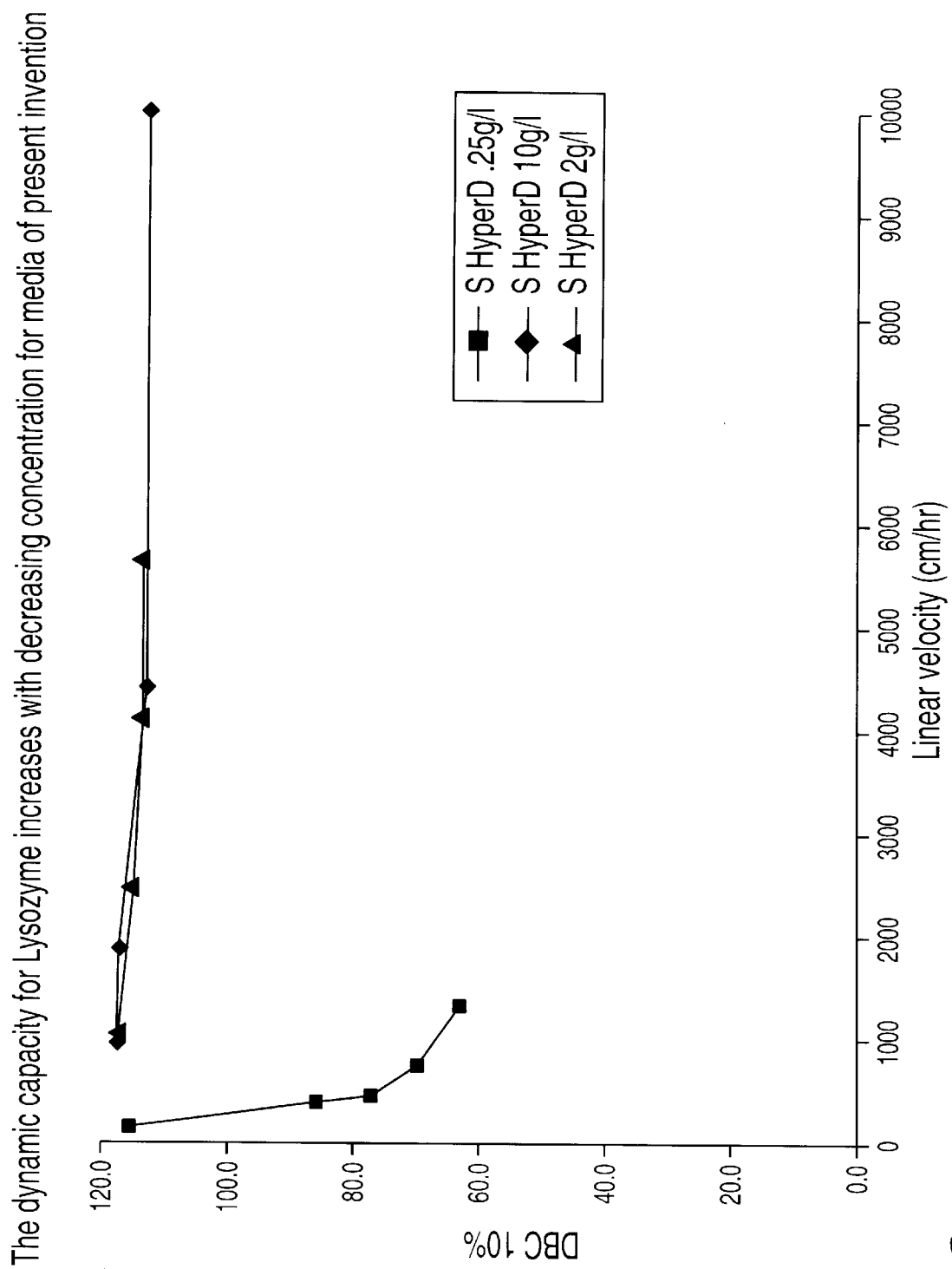
FIG. 12 shows graphs of the dynamic capacity of lysozyme on a present invention (S HyperD M) having a 75 μm particle size, plotted as a function of velocity at two different solute concentrations.

Additional testing at various bed velocities yielded the dynamic capacity measurements for lysozyme shown in FIG. 12 for three lysozyme feed concentrations. The dynamic capacity of the media when exposed to lysozyme at 0.25 mg/mL was nearly constant out to bed velocities of nearly 10,000 cm/hr.

Example 38
Decrease in dynamic capacity with decreasing applied lysozyme concentration for prior-art material A 15 cm by 0.2 cm column was packed with S Source 30, a cation-exchange media characterized with an approximately 30 µm particle size (Pharmacia, Uppsala, Sweden). The protein lysozyme was prepared at two concentrations (0.25 mg/mL and 10 mg/mL) in a 50 mM acetate buffer adjusted to pH 4.5. The column was then loaded with these lysozyme feed solutions at varying velocities, and the amount of lysozyme retained in the column at 10% breakthrough was determined. The dynamic capacity was calculated from the amount of lysozyme retained in the column and the volume of the media. In experiments conducted at a bed velocity of about 1000 cm/hr with the 0.25 mg/mL lysozyme feed solution, the media was determined to exhibit a dynamic capacity of 73 mg/mL, while operation at the same velocity of about 1000 cm/hr but with the more concentrated 10 mg/mL lysozyme solution yielded a measured dynamic capacity of 95 mg/mL, a significant increase over that measured in experiments conducted with the 0.25 mg/mL feed solution.

Figure 13:
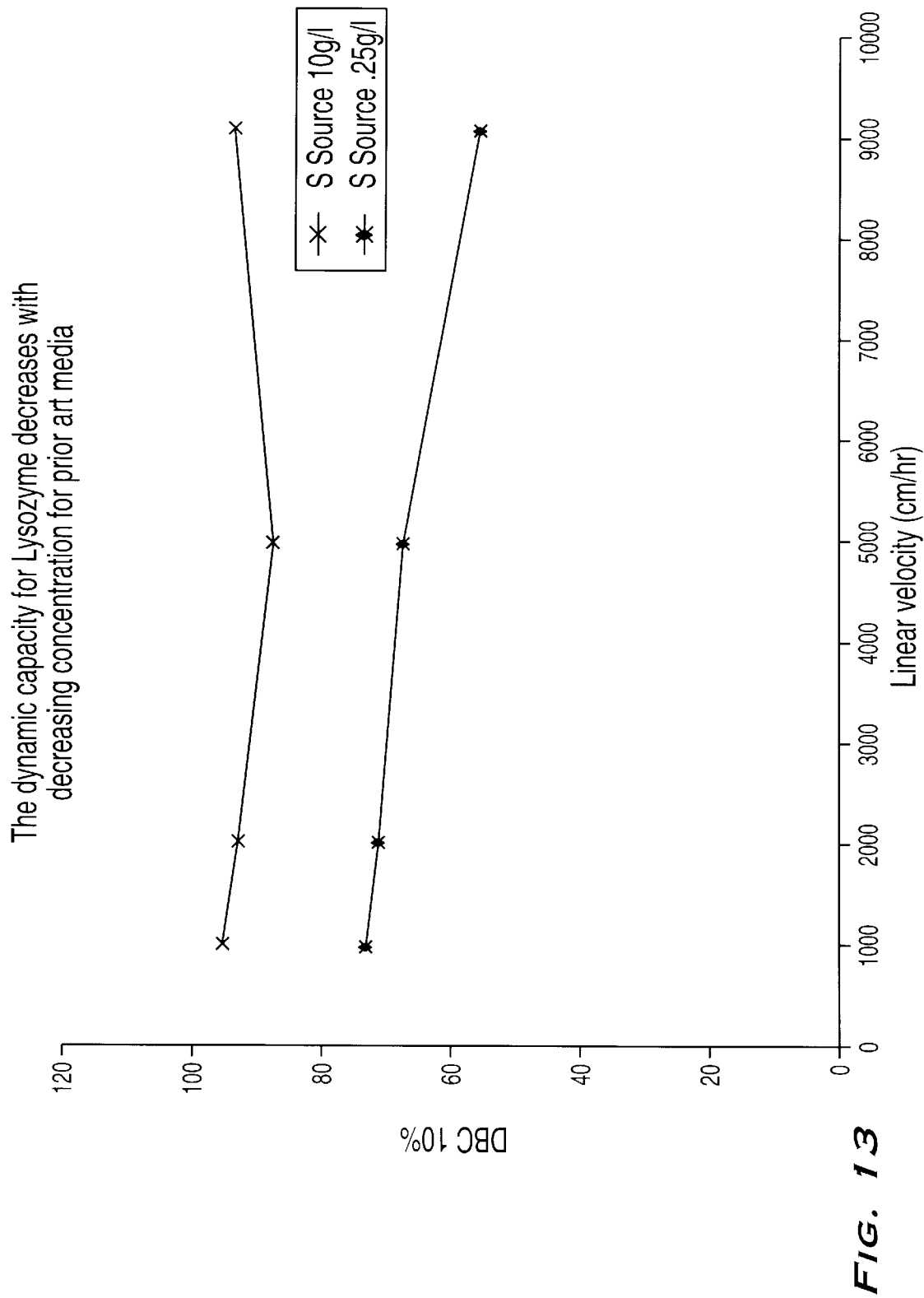
FIG. 13 shows graphs of the dynamic capacity of lysozyme on a prior-art media, Source 30, plotted as a function of velocity at two different solute concentrations.

Further testing performed at a number of different bed velocities produced FIG. 13, which shows dynamic capacity of the Source 30 media as function of linear velocity and lysozyme concentration in the feed. It may be noted that, because the Source media has such a small particle size (about 30 µm), its dynamic capacity changes little with increasing superficial column velocity. While this is a desirable feature of the Source 30 media, it is attributable to the small particle size (and not to efficient intraparticle mass transfer). A significant drawback associated with the use of small-particle-size media is the fact that pressure drops across columns packed with such conventional media can be excessive when such columns are operated at high bed velocities.

The consequences of the present invention's provision of media characterized by exhibiting higher dynamic capacities at low solute concentrations than at high solute concentrations are significant. In particular, the media of the present invention are particularly well suited for capturing various solutes from especially dilute feed streams. This novel and unexpected performance is especially important in biotechnology, where therapeutic proteins and other biological solutes must frequently be recovered from exquisitely dilute solutions.

It should be apparent to those skilled in the art that other compositions and methods not specifically disclosed in the instant specification are, nevertheless, contemplated thereby. Such other compositions and methods are considered to be within the scope and spirit of the present invention. Hence, the invention should not be limited by the description of the specific embodiments disclosed herein but only by the following claims.

What is claimed is:

1. A method for the separation of biological molecules from dilute solutions by chromatography which comprises the steps of:

selecting a composite media comprising a porous support comprising voids containing a polymeric network, wherein the composite media has a size exclusion limit of about 500 Daltons to about 2,000,000 Daltons and provides a value of a flux enhancement factor E greater than about 3, as determined by the equation $$E = \frac{D_s q_0}{\frac{D_f \varepsilon_p}{\tau} C_0}$$

in which $D_s$ is the experimentally measured effective intraparticle diffusivity of a biological molecule of interest, $q_0$ is the equilibrium concentration of the molecule within the media particles at equilibrium with $C_0$, $D_f$ is the diffusivity in free solution of said molecule, $\varepsilon_p$ is the fractional void volume of the porous support of the composite media, $\tau$ is the tortuosity of the porous support of the composite media, and $C_0$ is the concentration of said molecule in the feed solution to separate at least one of the molecules from the mixture;

passing, at a flow rate of at least about 50 cm/hr, a sample containing a mixture of biological macromolecules including a biological macromolecule of interest, wherein initial $C_0$ is less than about 2 milligrams per milliliter, through a column packed with the composite media which provides a larger dynamic capacity for said biological macromolecule of interest at a low concentration than the dynamic capacity provided by the same media for the same macromolecule at a higher concentration; and recovering the biological macromolecule of interest from the sample.

2. The method of claim 1, wherein said composite media provides a larger dynamic capacity for said macromolecule at initial feed concentrations of less than about 2 milligrams per milliliter than the dynamic capacity provided by the same media for the same macromolecule at initial feed concentrations of greater than about 2 milligrams per milliliter.

3. The method of claim 2, wherein said media provides a larger dynamic capacity for said macromolecule at initial feed concentrations in the range of about 10 micrograms per milliliter to about 2 milligrams per milliliter than the dynamic capacity provided by the same media for the same macromolecule at initial feed concentrations in the range of about 2 milligrams per milliliter to about 100 milligrams per milliliter.

4. The method of claim 1, wherein the initial feed concentration of said biological macromolecule of interest is about 10 micrograms per milliliter to less than about 2 milligrams per milliliter for passage through the column.

5. The method of claim 1, wherein $C_0$ is at least about 10 micrograms per milliliter and E is at least about 20.

6. The method of claim 1, which further comprises selecting the composite media to be a chromatographic media so that said biological macromolecules can be separated by chromatography.

7. The method of claim 6, wherein said chromatography is ion-exchange chromatography.

8. The method of claim 7, which further comprises selecting the ion-exchange chromatography media to be one that provides an intraparticle diffusional flux that is faster than the diffusional flux of the biological macromolecules in solution, to separate at least one of said biological macromolecules from said sample.

9. The method of claim 8, wherein the intraparticle diffusional transport rate is at least 30% higher than the diffusional transport rate of said biological macromolecules in solution.

10. The method of claim 9, wherein the recovery step comprises passing an eluent solution through the packed column to effect the separation of a preselected biological macromolecule from the mixture.

11. The method of claim 10, which further comprises selecting said biological macromolecule to be a protein, an oligopeptide, a carbohydrate, or a polynucleotide.

12. The method of claim 1, wherein the recovery step comprises passing an eluent solution through said packed column to effect the separation of a preselected biological macromolecule from said mixture.

13. The method of claim 12, which further comprises selecting said biological macromolecule to be a protein, an oligopeptide, a carbohydrate, or a polynucleotide.

14. The method of claim 1, wherein said flow rate is at least about 500 cm/hr.

15. The method of claim 14, wherein said flow rate is at least about 1000 cm/hr.

* * * * *